US010943162B2

(12) United States Patent
Herranen et al.

(10) Patent No.: US 10,943,162 B2
(45) Date of Patent: Mar. 9, 2021

(54) SEALING LABEL

(71) Applicant: UPM Raflatac Oy, Tampere (FI)

(72) Inventors: Jari Herranen, Tampere (FI); Pasi Lehtonen, Nokia (FI); Markku Pietarinen, Tampere (FI)

(73) Assignee: UPM RAFLATAC OY, Tampere (FI)

( * ) Notice: Subject to any disclaimer, the term of this patent is extended or adjusted under 35 U.S.C. 154(b) by 0 days.

(21) Appl. No.: 16/456,049

(22) Filed: Jun. 28, 2019

(65) Prior Publication Data
US 2020/0005105 A1 Jan. 2, 2020

(30) Foreign Application Priority Data
Jul. 2, 2018 (FI) ...................................... 20185610

(51) Int. Cl.
| G06K 19/06 | (2006.01) |
| B42D 25/378 | (2014.01) |
| G09F 3/00 | (2006.01) |
| G09F 3/10 | (2006.01) |
| C12Q 1/6874 | (2018.01) |
| G01N 21/64 | (2006.01) |
| G09F 3/02 | (2006.01) |

(52) U.S. Cl.
CPC ..... *G06K 19/06037* (2013.01); *B42D 25/378* (2014.10); *C12Q 1/6874* (2013.01); *G01N 21/6428* (2013.01); *G09F 3/0297* (2013.01); *G09F 3/10* (2013.01); *G09F 2003/0277* (2013.01)

(58) Field of Classification Search
CPC ............ G06K 19/00; G06K 19/06046; G06Q 10/0875; C12Q 1/6874; C12Q 1/6869; G01N 21/6428; G01N 21/648
USPC ......................................... 235/494, 454, 385
See application file for complete search history.

(56) References Cited

U.S. PATENT DOCUMENTS

| 5,366,087 A * | 11/1994 | Bane ..................... G09F 3/0288 |
| | | 206/459.5 |
| 2010/0108874 A1 | 5/2010 | Zahedi |
| 2014/0103373 A1* | 4/2014 | Li .............................. F21V 7/26 |
| | | 257/88 |
| 2016/0180747 A1* | 6/2016 | Pietarinen ................ C09J 7/243 |
| | | 206/438 |
| 2016/0275326 A1* | 9/2016 | Falkenstern .......... G06T 1/0021 |
| 2017/0248809 A1* | 8/2017 | Oba ...................... G02F 1/1336 |

FOREIGN PATENT DOCUMENTS

| EP | 1850308 A2 | 10/2007 |
| JP | H04119387 A | 4/1992 |

* cited by examiner

*Primary Examiner* — Daniel St Cyr
(74) *Attorney, Agent, or Firm* — Cantor Colburn LLP

(57) ABSTRACT

A method, comprising:
providing a combination of a package and a label attached to the package, wherein the label comprises a fluorescent substance,
illuminating the label with excitation light so as to cause the label to emit fluorescence light,
capturing an image of the label by using an imaging unit, and
detecting the position of the label by analyzing the captured image and/or detecting a degree of adhesion of the label by analyzing the captured image.

19 Claims, 27 Drawing Sheets

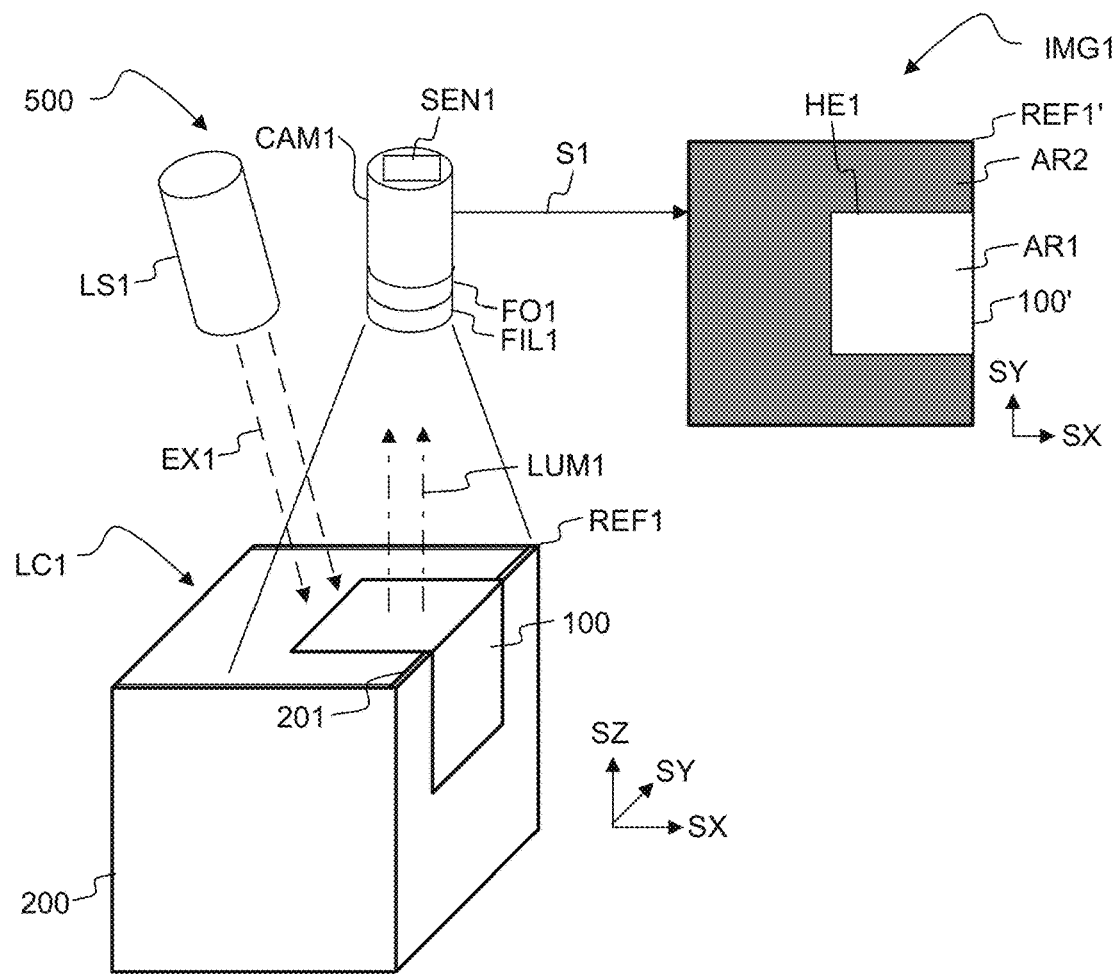
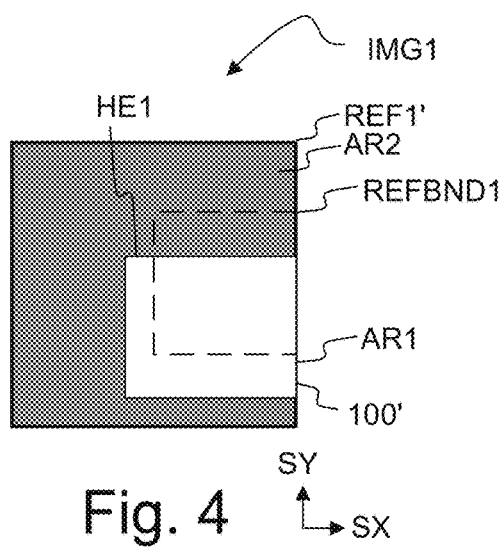
Fig. 4
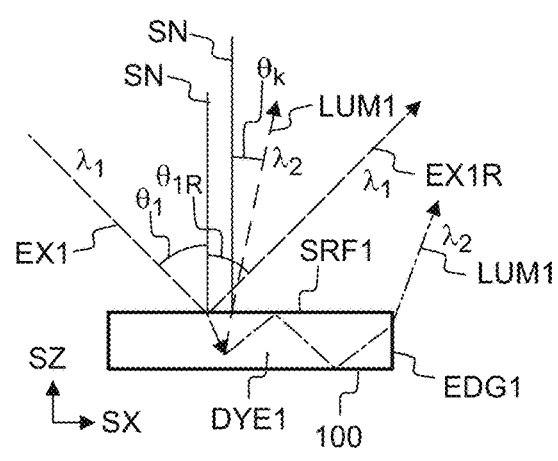
Fig. 5

SEALING LABEL

CROSS REFERENCE TO RELATED APPLICATIONS

This application claims the benefit of Finnish Application No. 20185610, filed Jul. 2, 2018, which is incorporated by reference herein in its entirety.

FIELD

Some embodiments relate to adhesive labels.

BACKGROUND

A sealed package may comprise a package and a sealing label attached to the package. An intact properly sealed package may be interpreted to be an indication that the product contained in the package is genuine. The sealing label may be an adhesive label.

SUMMARY

An object of the invention may be to provide a sealing label. An object may be to provide a method for producing a sealing label. An object may be a combination of a package and a sealing label attached to the package. An object may be an apparatus for monitoring position of a label attached to a package. An object may be an apparatus for applying sealing labels. An object may be a system for gathering data related to sealed packages.

According to an aspect, there is provided a label comprising:
a carrier layer and
an adhesive layer,
wherein the label comprises a wavelength conversion layer, which comprises a fluorescent substance.

According to an aspect, there is provided a label comprising:
a carrier layer and
an adhesive layer,
wherein the label comprises a waveguiding wavelength conversion layer, which comprises a fluorescent substance.

According to an aspect, there is provided a sealed package, which comprises a package and a label attached to the package, wherein the label comprises a carrier layer and an adhesive layer, wherein the label comprises a wavelength conversion layer, which comprises a fluorescent substance.

According to an aspect, there is provided a method comprising providing a combination of a package and a label attached to the package, wherein the label comprises a carrier layer and an adhesive layer, wherein the label comprises a wavelength conversion layer, which comprises a fluorescent substance,
the method further comprising:
illuminating the label with excitation light so as to cause the label to emit fluorescence light,
capturing an image of the label by using an imaging unit, and analyzing the captured image.

According to an aspect, the method comprises checking whether the adhesive layer of the label is properly in contact with the package, by comparing the captured image with reference data.

According to an aspect, there is provided an apparatus for detecting position of a label with respect to package, the apparatus comprising:
a light source to provide excitation light,
an imaging unit for capturing an image of a labeled package,
one or more data processors to determine the position of the label by analyzing the captured image.

The sealing label may comprise a wavelength conversion layer to facilitate detection of the position of the label. The wavelength conversion layer may, in turn, comprise a fluorescent substance to facilitate detection of the position of the label.

The sealing label may comprise a modulating structure to spatially modulate radiance of fluorescence light emitted from the label. The modulating structure may provide a predetermined pattern when the label is illuminated with excitation light. The pattern may be e.g. target pattern and/or a code. The pattern may be machine-detectable.

The modulating structure may be implemented e.g. by using optically filtering regions, by using non-fluorescing regions, by varying concentration of the fluorescent substance at different transverse positions, and/or by varying thickness of a fluorescent material layer.

In an embodiment, the fluorescent substance may be distributed to a relatively thick material layer to optimize fluorescence quantum yield and/or to optimize consumption of the fluorescent substance.

The label may further comprise a waveguiding layer, which comprises the fluorescent substance. The label may comprise a waveguiding layer, which comprises a fluorescent sub-layer. The label may comprise a waveguiding fluorescent layer. Illuminating the fluorescent substance with excitation light may cause emission of fluorescence light. A part of the fluorescence light may be confined to the waveguiding layer by total internal reflection. The fluorescence light may be coupled out of the waveguiding layer by out-coupling elements and/or by out-coupling features. The fluorescence light may be coupled out of the waveguiding layer e.g. by grooves, and/or perforations.

Each sealing label may be arranged to display a unique code, when illuminated with the excitation light. Using the code may allow authentication and/or tracking of the sealing labels. This may make stealing and/or falsification of the labels more difficult.

A sealed package may comprise a package and the sealing label attached to the package. An intact properly sealed package may be interpreted to be an indication that the product contained in the package is genuine. The sealing label may be applied e.g. in order to seal a packaging of a medicinal product. The package may contain a medicament. Checking and/or verifying proper sealing of the package may be important e.g. when the package contains a medicament.

The proper sealing of a package may be checked e.g. after the package has been closed and/or after the sealing label has been attached to the package. The proper sealing of a package may be checked e.g. before the package is forwarded to a next party involved in transportation and/or storage of the packaged product.

The proper sealing of a package may be checked by using a monitoring apparatus, which illuminates the sealing label with excitation light, captures an image of the sealing label, and determines the position of the label by analyzing the captured image. The monitoring apparatus may e.g. provide an alarm signal if a label is determined to be missing or if a label is determined to be at a wrong position.

The sealing label may be substantially transparent. The transparent label may bring benefit in use. Clear film labels may enable staying with the current packaging design, i.e. there is no need to change existing artwork. A change of the visual appearance of the package may require approval from an authority of state. Consequently, a change of the visual appearance of the package may be time consuming. The transparent label may provide a substantially no-label look, wherein it is not necessary to change or adapt the visual appearance of the package according to the sealing label.

Using a transparent label may make it difficult to detect the presence and/or position of a label attached to a package. For example, the package may have a substantially white color, and it may be difficult to reliably detect the presence and/or position of the transparent label attached on the surface of the package. The label may comprise a wavelength conversion layer to facilitate reliable detection of the label, in a situation where the label is illuminated with excitation light. In particular, a substantially transparent label may comprise a wavelength conversion layer to facilitate reliable detection of the label.

The combination of the package and the sealing label may comprise e.g.
a tamper evident feature,
an overt or covert authentication feature, and
a track and trace feature.

These features may allow authentication of the individual packaging through the entire supply chain. These features may together allow authentication of the individual packaging through the entire supply chain.

The sealing label may be used as an anti-tampering device. The sealing label may also be called e.g. as tamper evident label. By tampering or opening or tearing off the sealing label the sealing label may become irreversibly broken and/or deformed to indicate that the sealing label is no more intact.

The consumer should be the first person who opens the sealed package in a legal supply chain. The combination of the sealing label and the package may visually indicate to the consumer whether he is the first person who opens the sealed package. The sealing label may be arranged to operate such that it is clearly evident to the customer whether tampering has occurred prior to authorized use or not.

The materials and the dimensions of the sealing label may be selected such that it is difficult or impossible to remove the sealing label from a package without causing irreversible alteration of the label and/or the package.

As an additional tamper evident feature, the sealing label may be arranged to cause visible cardboard tear in a situation where the sealing label is pulled away from the package. In particular, the dimensions and the materials of the sealing label may be selected such that pulling the sealing label from a varnished cardboard causes irreversible tearing of the varnished cardboard. In particular, the materials and the dimensions of the sealing label may be selected such that it is difficult or impossible to remove the sealing label from varnished cardboard without causing irreversible alteration of the label and the varnished cardboard. Pulling of the label may cause irreversible elongation and/or delamination of the label, wherein pulling of the label may also cause that the surface of the packaging may be torn or ripped off.

An individual sealed package may comprise a unique identifier (UI) and/or an anti-tampering device (ATD). The unique identifier may enable identification and authentication of the individual sealed package, from among a high number of other substantially similar sealed packages. Each package may comprise a different identifier. The identifier may be e.g. an alphanumerical code, a (one-dimensional) barcode, or a two-dimensional barcode (e.g. QR code). The anti-tampering device may allow detecting whether the individual sealed package has been opened and/or tampered.

A database may contain information about a plurality of packages. The database may contain data, which indicates e.g. the contents of a package, manufacturer of the contents of the package, manufacturing date of the contents of the package, packing date of the package, delivery route of the package, delivery dates of the package, and/or distributors of the package. The database may contain information about where, when and who has read the identifier of a package. The data associated with an individual package may be retrieved from the database e.g. based on the identifier of said individual package. Using the identifier together with data stored in the database may allow tracing the delivery route and delivery times of the package. A distributor and/or a person may use the identifier e.g. to check the authenticity of a product contained in the package.

The identifier of a package may be read and used together with the database to perform an authenticity check. The identifier of a package may be read e.g. at a storage or at a point of sale. The authenticity check may fail e.g. if:
a package associated with the identifier has not been produced,
a package associated with the identifier should contain a different product,
a package associated with the identifier has not been transported to said storage or to said point of sale,
the same identifier has recently been read at a different location which is not a part of the authorized supply chain, and/or
a package associated with the identifier has already been handed over to a consumer.

The labels may comprise a wavelength conversion layer, which comprises a fluorescent substance. Thanks to using the wavelength conversion layer, the same monitoring apparatus may be used to detect the position of a first label attached to a first package, and the position of a second label attached to a second package. Thanks to using the wavelength conversion layer, the same monitoring apparatus may be used to reliably detect the positions of substantially transparent labels also in a situation where the color of the first package is different from the color of the second package. The first package may have e.g. a substantially white color, and the second package may have a dark color. The average reflectance of the first package in the wavelength range 400 nm to 700 nm may be e.g. higher than 80%, wherein the average reflectance of the second package in the wavelength range 400 nm to 700 nm may be e.g. lower than 40%.

The label may be arranged to provide a predetermined pattern, which may be detected by using an imaging unit when the label is illuminated with excitation light. The monitoring apparatus may be arranged to read and/or detect the pattern. The pattern may be e.g. a QR code.

In an embodiment, the monitoring apparatus may comprise one or more optical filters to increase contrast between the transparent label and the surface of the package.

BRIEF DESCRIPTION OF THE DRAWINGS

In the following examples, several variations will be described in more detail with reference to the appended drawings, in which FIG. 3 shows, by way of example, detecting the position of a label by using a monitoring apparatus, FIG. 4 shows, by way of example, an image of a package, wherein the label is in a wrong position, FIG. 5 shows, by way of example, in a cross-sectional view, a sealing label which comprises fluorescent substance, FIG. 14a shows, by way of example, in a top view, the label of FIG. 14b.

DETAILED DESCRIPTION

Figure 1:
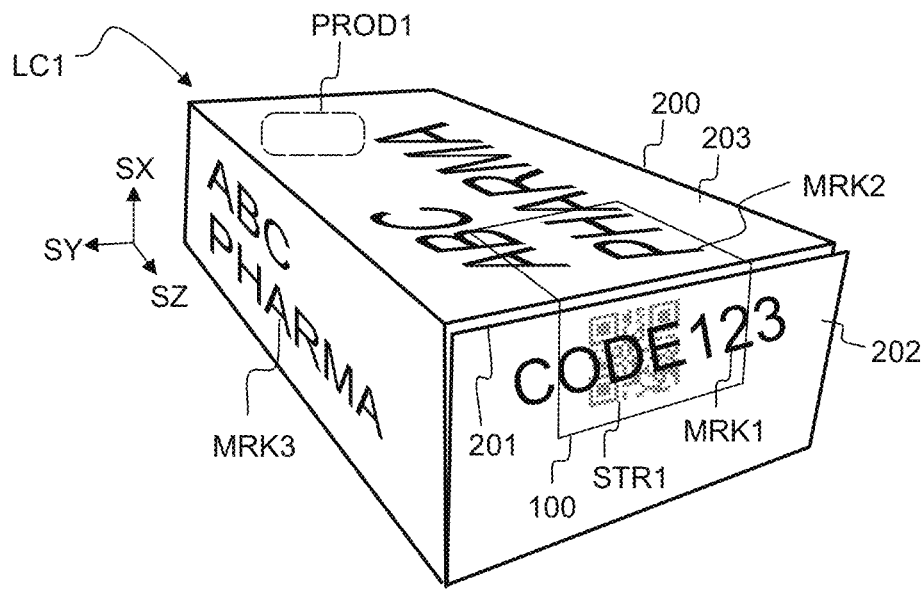
FIG. 1 shows, by way of example, in a three-dimensional view, a package sealed with a sealing label.

Referring to FIG. 1, a package 200 may be sealed with a label 100. The package 200 and the label 100 may form a combination LC1 when the label 100 is attached to the package 200. The combination LC1 may also be called as a sealed package.

The package 200 may contain a product PROD1. The package 200 may contain e.g. a substance PROD1 selected from the group consisting of medicine, cosmetic product, and foodstuff. In particular, the package 200 may contain a medicament.

The package 200 may be e.g. a varnished cardboard box. The package may comprise one or more substantially rectangular faces 202, 203. The package may comprise a lid 202, which may be joined to a side of the package e.g. by a flexible hinge. The package 200 may comprise an opening joint 201. The sealing label 100 may be attached to the package e.g. on both sides of the opening joint 20 (e.g. on the face 202 and on the face 203). A consumer may access the product e.g. by breaking the sealing label 100 and by opening the joint 201.

In an embodiment, an opening joint 201 of the package 200 may be opened by breaking the label 100 without causing visually detectable damage to the package 200. In an embodiment, the opening joint 201 cannot be opened without causing visually detectable damage to the package 200. In an embodiment, the package may comprise a further opening portion, which is arranged to be opened by breaking the package.

The package 200 may comprise one or more visually detectable markings MRK1, MRK2, MRK3. The markings MRK1, MRK2, MRK3 may be e.g. printed markings formed on the surface of the package 200. The sealing label 100 may be substantially transparent so that a marking MRK1 located beneath the label 100 may be seen through the label 100, in a situation where the sealed package is illuminated with white light. The label 100 may be substantially transparent such that one or more markings MRK1, MRK2, MRK3 located beneath the label 100 may be detected with the naked eye when illuminated with normal white light, which does not comprise ultraviolet light.

For example, optical transmittance of the label 100 at the wavelength of 650 nm may be higher than 80% in at least 90% of the area of the label 100.

For example, at least 90% of the (one sided) area of the label 100 may be substantially colorless when illuminated with normal white light, which does not comprise ultraviolet light.

The label 100 may comprise a fluorescent substance DYE1 to emit fluorescence light LUM1 in a situation where the label 100 is illuminated with excitation light EX1.

The label 100 may comprise a substantially transparent modulating structure STR1 to spatially modulate radiance of the fluorescence light, in a situation where the label 100 is illuminated with excitation light EX1. The modulating structure STR1 may provide a machine-detectable pattern, which may be used for detecting the position of the label with respect to the package.

The modulating structure STR1 may provide a target pattern UMRK1 (see e.g. FIG. 7c), which may be easily recognized by an image recognition algorithm. The pattern may comprise e.g. a checkerboard pattern and/or a stripe pattern.

The modulating structure STR1 may provide a pattern, which carriers information. The pattern may comprise e.g. a one-dimensional barcode, a two-dimensional barcode, an alphanumerical code and/or a character string.

The modulating structure STR1 may make falsification of the sealing label more difficult. The modulating structure STR1 may operate as an anti-tamper feature. In an embodiment, each sealing label of a manufacturing batch may carry common identification code. In an embodiment, each sealing label may carry a different unique code, so as to allow identification and/or tracking of the sealing label. The code of the label may make it more difficult to steal sealing labels and/or to make unauthorized copies of the sealing labels. The code of a sealing label of a package may also be read with a reader device in order to perform an authenticity check.

Figure 2:
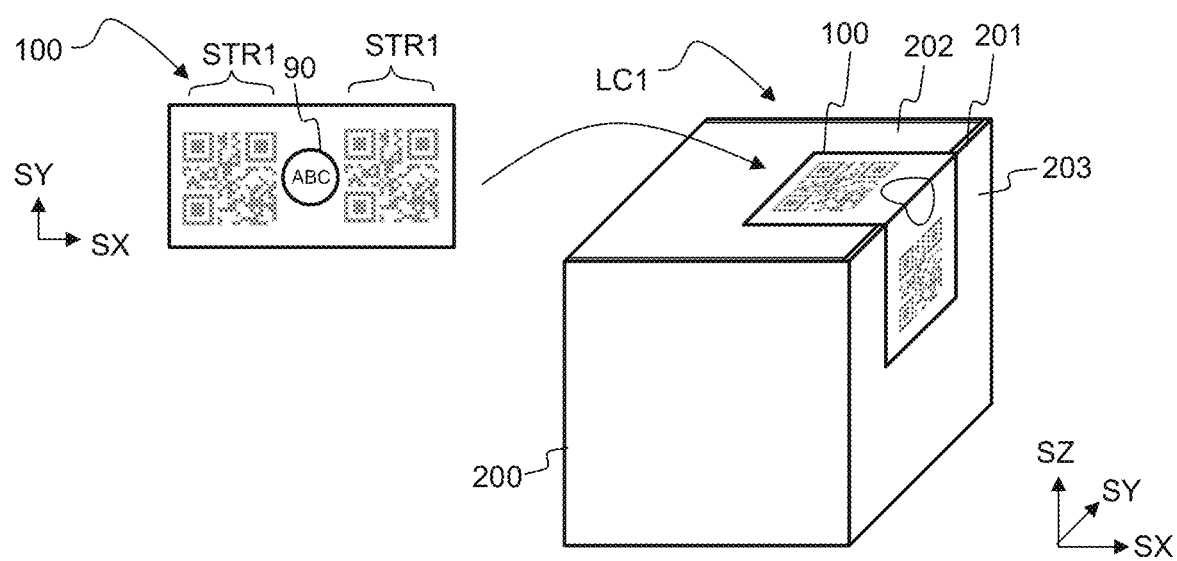
FIG. 2 shows, by way of example, applying a sealing label to a package.

The label 100 may further comprise one or more visually detectable markings 90 to indicate authenticity and/or to indicate that the label has not been tampered (see e.g. FIG. 2). The marking 90 may be detected with the naked eye when illuminated with normal white light, which does not comprise ultraviolet light.

The marking 90 may be produced e.g. by printing with ink. The label 100 may comprise a machine-readable pattern. The marking 90 may be formed e.g. on the carrier layer 10. The marking 90 may also be located e.g. below the fluorescent layer of the label 100 such that the printed marking (90) does not prevent detection of the fluorescence light LUM1 of a machine-readable pattern.

Figure 15A:
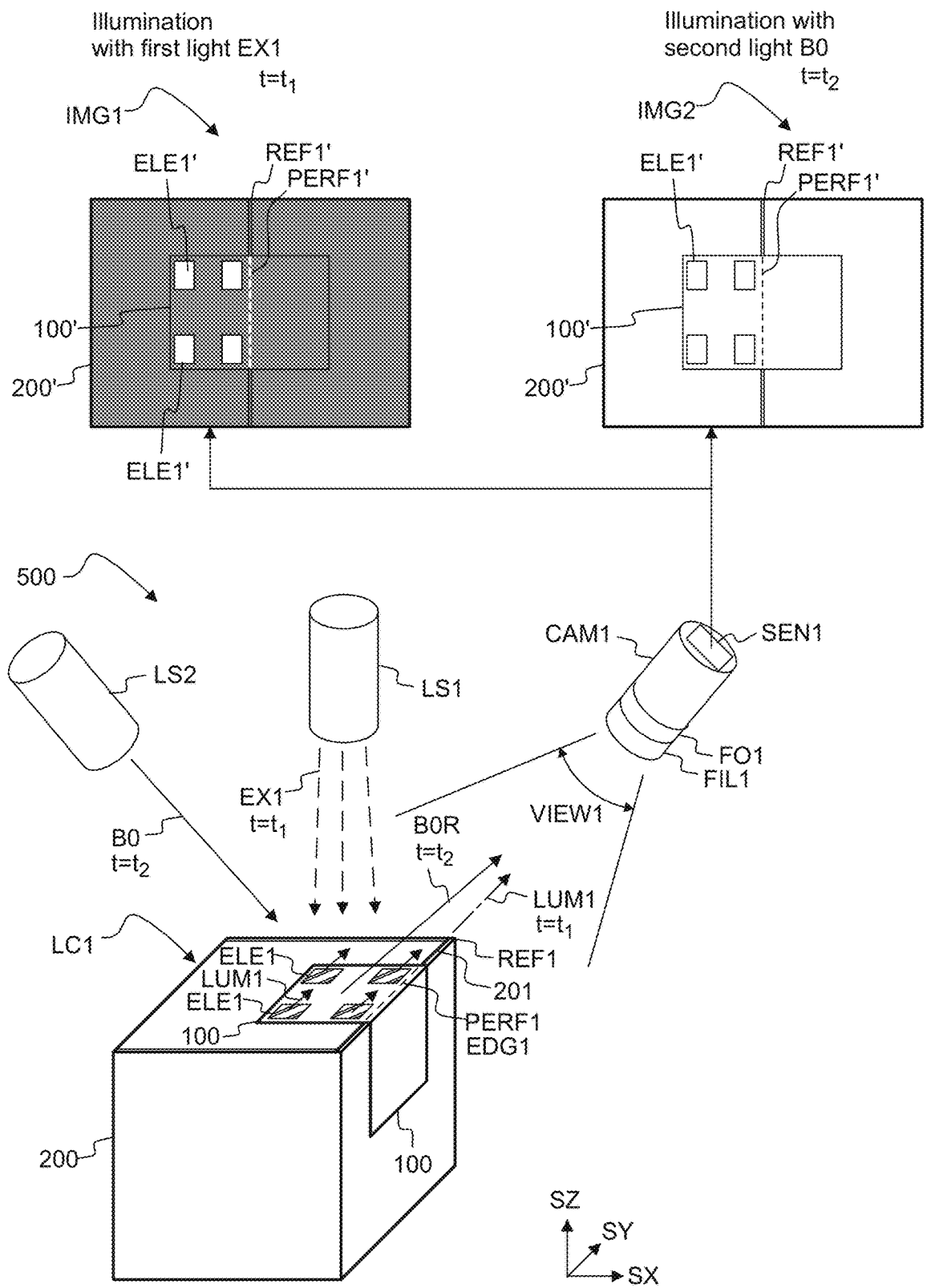
FIG. 15a shows, by way of example, monitoring the position of the label by using a monitoring apparatus.

The label 100 may further comprise one or more perforations PERF1 to facilitate opening of the sealed package LC1 (see e.g. FIG. 15a).

The label 100 may have a carrier layer 10, which comprises or consists of plastic. The label 100 may comprise an adhesive layer 20. The adhesive layer 20 may comprise pressure sensitive adhesive. The outer surface of the package 200 may e.g. comprise or consist of varnished cardboard.

SX, SY and SZ denote orthogonal directions.

Referring to FIG. 2, the sealing label 100 may be attached to both sides of an opening joint 201.

FIG. 3 shows, by way of example, an apparatus 500 for monitoring the position of the label 100. The apparatus 500 may comprise a light source LS1 to provide excitation light EX1. The apparatus 500 may comprise an imaging unit CAM1 to capture an image IMG1 of the label 100, when the label 100 is illuminated with the excitation light EX1.

The imaging unit CAM1 may be called e.g. as a camera. The camera CAM1 may comprise an image sensor SEN1 and focusing optics FO1 to form an image IMG1 of an object by focusing light to the image sensor SEN1. The focusing optics FO1 may comprise e.g. one or more lenses. The image sensor SEN1 may be e.g. a CMOS sensor or an CCD sensor. CMOS means complementary metal oxide semiconductor. CCD means charge coupled device. The camera CAM1 may comprise an optical filter FIL1 to increase contrast of the captured image IMG1.

At least a part of the label 100 may emit fluorescence light LUM1 when illuminated with the excitation light EX1. The captured image IMG1 may comprise partial images, which may be images of the regions of the label and the package. The image IMG1 may comprise a partial image 100' which may be an image of the label 100. The image IMG1 may comprise a partial image AR1 which may be an image of a fluorescing region the label 100. The image IMG1 may comprise a partial image AR2, which may be an image of the uncovered region of the package 200. The image may comprise a high contrast edge HE1 between the partial images AR1, AR2. The apparatus 500 may analyze the captured image IMG1, and the position of the edge HE1 may be detected by an image recognition algorithm. The image IMG1 may comprise a partial image REF1, which may be an image of a reference point REF1 of the package. The reference point REF1 may be e.g. at a corner of the package 200. The apparatus may be arranged to detect the position of the edge HE1 with respect to the reference point REF1.

The apparatus may comprise one or more optical filters FIL1 to provide a desired spectral response of the combination of the camera CAM1 and the one or more filters FIL1. The apparatus may comprise one or more optical filters FIL1 to modify spectral response of the combination of the camera CAM1 and the one or more filters FIL1. The method may comprise using one or more optical filters FIL1 to define spectral sensitivity range of the camera CAM1. The method may comprise using a filter FIL1 to increase modulation depth (contrast) of the image IMG1 formed by focusing the fluorescence light LUM1.

The filter FIL1 may be positioned e.g. between the label 100 and the camera CAM1. The camera CAM1 may comprise the filter FIL1. The filter FIL1 may be e.g. absorptive filter and/or an interference filter. The filter FIL1 may be a band pass filter, a band rejection filter, or a long pass filter. The spectral transmittance of the filter FIL1 may be selected to suppress the intensity of reflected and/or scattered excitation light, wherein the selected spectral transmittance of the filter FIL1 may allow a significant part of the fluorescence light LUM1 to propagate to the image sensor SEN1 of the camera CAM1. The filter FIL1 may increase the contrast (i.e. modulation depth) of the image IMG1 by reducing a ratio of first intensity to second intensity, wherein the first intensity is the intensity of reflected and/or scattered excitation light impinging on the image sensor SEN1, and the second intensity is the intensity of fluorescence light impinging on the image sensor SEN1.

FIG. 4 shows, by way of example, a captured image IMG1 where the label 100 is at a wrong position. The boundary REFBMD1 indicates a desired position of the label 100. The desired position of the label 100 may be specified e.g. by reference data stored in a memory of the monitoring apparatus 500.

The monitoring apparatus 500 may compare the detected position of the boundary HE1 with the reference data in order to determine whether the label 100 is at a correct position or at a wrong position.

The monitoring apparatus 500 may e.g. provide an alarm signal when the label 100 is at a wrong position. The monitoring apparatus 500 may e.g. control operation of a labeling unit based on the detected position of the label.

The method may comprise:
providing a combination (LC1) of a package (200) and a label (100) attached to the package (200), the label (100) comprising a waveguiding structure (WG1), which comprises a fluorescent substance (DYE1),
illuminating the label (100) with excitation light (EX1) so as to cause the label (100) to emit fluorescence light (LUM1),
capturing an image (IMG1) of the label (100) by using a spectrally selective imaging unit (CAM1), and
analyzing the captured image (IMG1).
Analyzing the captured image (IMG1) may comprise e.g.:
detecting a pattern,
recognizing a pattern,
recognizing a pattern, which represents a machine-readable code,
detecting the position of the label with respect to the package,
detecting the position of the label with respect to the package by comparing the captured image with reference data,
detecting the position of the label with respect to the package by comparing the captured image with one or more reference images,
checking whether the adhesive layer of the label is properly in contact with the package, by comparing the captured image with reference data,
checking whether the adhesive layer of the label is properly in contact with the package, by comparing the captured image one or more reference images.

Referring to FIG. 5, the excitation light EX1 may impinge on the label 100. A part of the excitation light EX1 may be absorbed to the fluorescent substance DYE1 such that the fluorescent substance DYE1 may emit fluorescence light LUM1.

The fluorescent substance DYE1 of the label 100 may absorb optical energy of the excitation light EX1. The optical energy of the excitation light EX1 may optically excite the fluorescent substance DYE1. The fluorescent substance DYE1 may release a part of the absorbed energy by emitting fluorescence light LUM1. A wavelength $\lambda_2$ of the fluorescence light LUM1 may be longer than a wavelength $\lambda_1$ of the excitation light EX1 also in a situation where the spectral intensity of the excitation light EX1 at the wavelength $\lambda_2$ is zero. Thus, the label 100 may operate as a wavelength conversion device.

In particular, the label 100 may emit fluorescence light LUM1 at a second different wavelength $\lambda_2$ in a situation where the label 100 is illuminated with excitation light EX1 at a first wavelength $\lambda_1$, and spectral intensity of the excitation light EX1 at the second wavelength $\lambda_2$ is equal to zero.

A part of the excitation light EX1 may be reflected from the label 100 as a reflected beam EX1R.

A part of the fluorescence light LUM1 may escape out of the label 100 through the upper major surface of the label 100.

The direction of an excitation light beam EX1 may be specified by an input angle $\theta_1$. The direction of the reflected beam EX1R may be specified by a reflection angle $\theta_{1R}$. The direction of a light ray of the fluorescence light LUM1 may be specified by an angle $\theta_k$. The angles $\theta_1$, $\theta_R$, $\theta_k$ may indicate direction with respect to a surface normal SN of the label 100. The reflection angle $\theta_{1R}$ may be substantially equal to the input angle $\theta_1$.

The direction ($\theta_k$) or directions of the fluorescence light LUM1 may be different from the direction ($\theta_{1R}$) of the reflected light EX1R. The label 100 may emit fluorescence light LUM1 to directions, which are different from the direction of the reflected beam EX1R. For example, the camera CAM1 of the monitoring system 500 may be positioned such that the camera CAM1 captures an image IMG1 by focusing the fluorescence light LUM1.

For example, the camera CAM1 of the monitoring system 500 may be positioned such that a major part of the reflected light EX1R is directed away from the camera CAM1. This may reduce reflections, which may disturb detecting the position of the label 100.

The label 100 may optionally comprise a waveguiding fluorescent layer. A part of fluorescence light LUM1 emitted inside the waveguiding layer may be confined to the waveguiding layer by total internal reflection (TIR). The trapped fluorescence light LUM1 may be coupled out of the waveguiding layer e.g. via an edge EDG1 of the label 100 and/or via an out-coupling element ELE1.

The fluorescent substance DYE1 may be mixed e.g. with the material of a polymer layer, with and adhesive and/or with printing ink. The carrier layer 10 may comprise fluorescent substance, the adhesive layer may comprise fluorescent substance and/or an additional material layer may comprise fluorescent substance.

An optimum fluorescence yield and/or optimum consumption of the fluorescent substance may be attained when the concentration of the fluorescent substance is in an optimum range in a fluorescent layer. In particular, the concentration of the fluorescent substance may be kept below a predetermined limit in order to provide an optimum ratio of the fluorescence yield to the concentration of the fluorescent substance. The fluorescence yield may increase in a nonlinear manner with increasing concentration of the fluorescent substance. The fluorescence yield may saturate at high concentrations such that an increase of the concentration causes a small or negligible increase of the fluorescence yield.

The fluorescent substance DYE1 may be mixed with one or more other materials such that the molecules of the fluorescent substance DYE1 are spatially distributed in the thickness direction of the wavelength conversion layer, in order to provide optimum fluorescence quantum yield and/or in order to provide optimum consumption of the fluorescent substance.

The thickness of the wavelength conversion layer may be e.g. greater than or equal to 1 µm. The thickness of the wavelength conversion layer may be e.g. in the range of 1 µm to 200 µm. The thickness of the wavelength conversion layer may be e.g. in the range of 5% to 80% of the total thickness of the label 100.

The fluorescent substance DYE1 may be e.g. an organic dye.

The fluorescent substance DYE1 may be e.g. a product called as DCM ([2-[2-[4-(dimethylamino)phenyl]ethenyl]-6-methyl-4H-pyran-4-ylidene] propanedinitrile).

The fluorescent substance DYE1 may be e.g. a perylene dye sold under a trade name "Lumogen F RED 305" by the company BASF. (N,N-Bis(2,6-diisopropylphenyl)-1,6,7,12-tetraphenoxyperylene-3,4:9,10-tetracarboxdiimide)

The fluorescent substance DYE1 may be e.g. selected from the group of coumarins. The fluorescent substance DYE1 may be e.g. coumarin.

The fluorescent substance DYE1 may be selected such that it is safe to handle, when contained within the label 100. The fluorescent substance DYE1 may be selected such that it is non-toxic when contained within the label 100.

Figure 6:
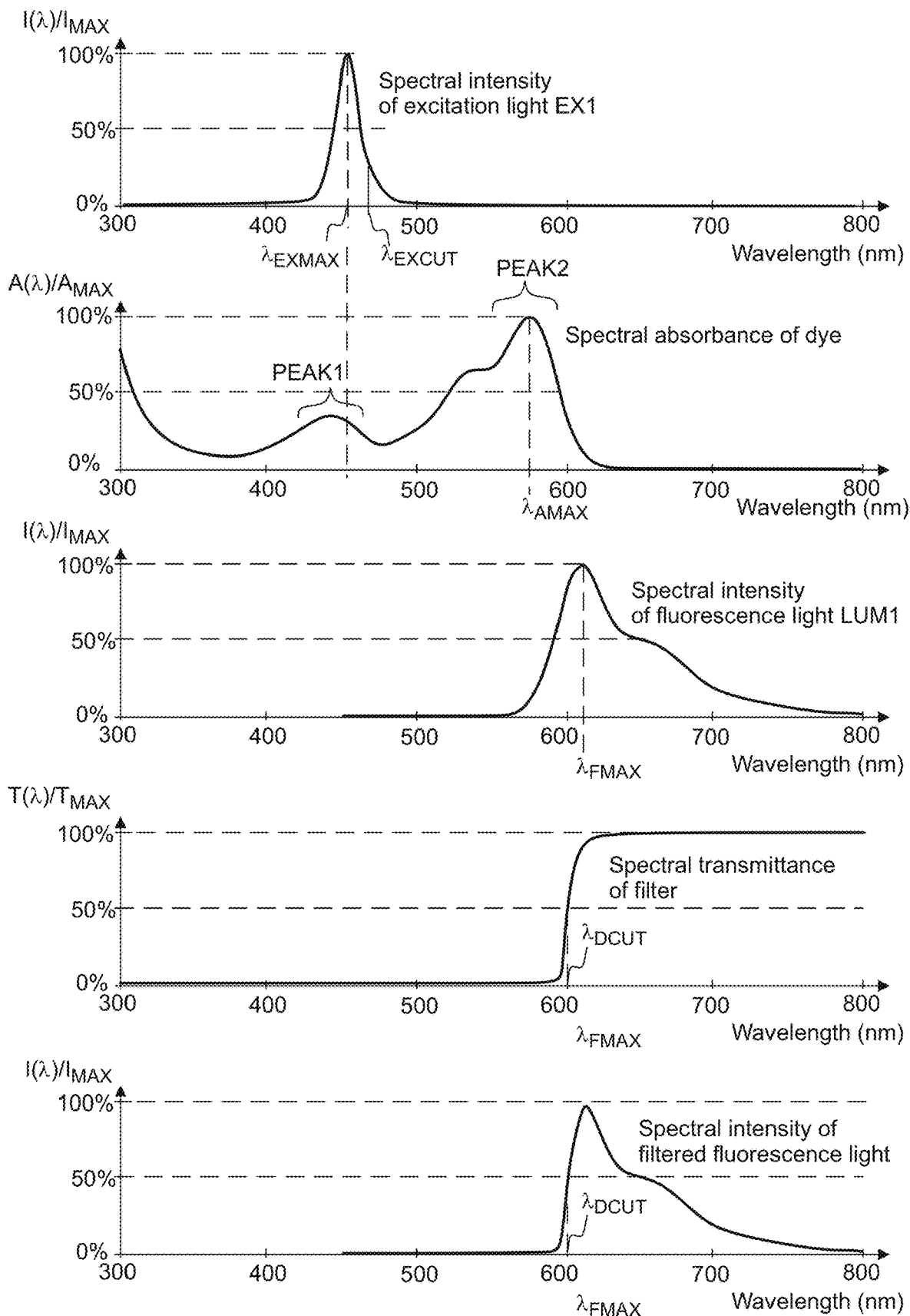
FIG. 6 shows, by way of example, wavelength conversion in the spectral domain.

FIG. 6 illustrates optical excitation of the fluorescent substance and spectrally selective detection of the fluorescence light.

The uppermost curve of FIG. 6 shows, by way of example, spectral intensity distribution of excitation light EX1. The excitation light EX1 may be provided such that at least 90% of optical energy of the excitation light EX1 may be at wavelengths shorter than a cutoff wavelength $\lambda_{EXCUT}$. The spectral intensity may have a maximum at a wavelength $\lambda_{EXMAX}$. The symbol I($\lambda$) denotes spectral intensity. The symbol $I_{MAX}$ denotes maximum value of the spectral intensity.

The second curve from the top shows spectral absorbance A($\lambda$) of the fluorescent substance DYE1. $A_{MAX}$ denotes maximum value of the spectral absorbance A($\lambda$). The spectral absorbance A($\lambda$) may have one or more peaks PEAK1, PEAK2. The spectral absorbance A($\lambda$) may have a maximum value $A_{MAX}$ at a wavelength $\lambda_{AMAX}$.

The fluorescent substance DYE1 and/or the spectrum of the excitation light EX1 may be selected such that the fluorescent substance DYE1 may absorb a sufficient fraction of the optical energy of the excitation light EX1. The fluorescent substance DYE1 and/or the spectrum of the excitation light EX1 may be selected such that the spectrum of the excitation light EX1 at least partly overlaps the absorbance spectrum of the fluorescent substance DYE1.

Referring to the third curve from the top of FIG. 6, the fluorescent substance DYE1 may emit the absorbed energy as fluorescence light LUM1. The fluorescent substance DYE1 may absorb excitation light EX1 at shorter wavelengths, and the fluorescent substance DYE1 may emit fluorescence light at longer wavelengths. Thus, the fluorescent substance DYE1 may operate as wavelength conversion medium.

The fluorescent substance DYE1 may emit fluorescence light LUM1 also at wavelengths where the spectral intensity of the excitation light EX1 is substantially equal to zero. The fluorescence light LUM1 may have a maximum at a wavelength $\lambda_{FMAX}$. The wavelength $\lambda_{FMAX}$ may be substantially longer than the wavelength $\lambda_{EXMAX}$. The wavelength $\lambda_{FMAX}$ may be substantially longer than the wavelength $\lambda_{EXCUT}$.

Referring to the fourth curve from the top of FIG. 6, the spectrum of fluorescence light LUM1 may be optionally modified by using an optical longpass filter FIL1. The optical longpass filter FIL1 may have a cutoff wavelength $\lambda_{DCUT}$ where the spectral transmittance T($\lambda$) is equal to 50% of maximum spectral transmittance $T_{MAX}$. The filter FIL1 may substantially prevent propagation of spectral components at wavelengths shorter than the cutoff wavelength $\lambda_{DCUT}$ to the camera CAM1. The filter FIL1 may allow propagation of spectral components at wavelengths longer than the cutoff wavelength $\lambda_{DCUT}$ to the camera CAM1.

The lowermost curve of FIG. 6 shows, by way of example, the spectrum of filtered fluorescence light LUM1. The filtered fluorescence light LUM1 may be obtained by filtering the fluorescence light LUM1 with the optical longpass filter FIL1.

The camera CAM1 may be arranged to capture an image by focusing the fluorescence light LUM1 to an image sensor. The camera CAM1 may be arranged to capture an image by focusing the filtered fluorescence light LUM1 to an image sensor.

The cutoff wavelength $\lambda_{DCUT}$ may be selected e.g. such that the cutoff wavelength $\lambda_{DCUT}$ is longer than or equal to the peak wavelength $\lambda_{EXMAX}$ of the excitation light EX1.

The cutoff wavelength XDCUT may be selected e.g. such that the cutoff wavelength $\lambda_{FCUT}$ is longer than or equal to the cutoff wavelength $\lambda_{EXCUT}$ of the excitation light EX1.

Using the fluorescent substance DYE1 for wavelength conversion may increase contrast of the image IMG1 captured by the camera CAM1. Using the optical filter FIL1 may further increase contrast of the image IMG1, by reducing the contribution of reflected light.

The fluorescent substance DYE1 and/or the light source LS1 may be selected such that the fluorescent substance DYE1 has sufficient absorbance at the peak wavelength $\lambda_{EXMAX}$ of the excitation light EX1. The fluorescent substance DYE1 and/or the excitation light EX1 may be selected such that an emission peak of the excitation light EX1 at least partly overlaps an absorbance peak of the fluorescent substance DYE1.

The excitation light source LS1 may comprise e.g. a light emitting diode (LED), a laser, or a gas discharge lamp (e.g. a xenon flashlamp).

The light source LS1 may be e.g. a blue LED, wherein the peak wavelength $\lambda_{EXMAX}$ may be e.g. substantially equal to 460 nm. The cutoff wavelength $\lambda_{EXCUT}$ may be e.g. substantially equal to 470 nm. The light source LS1 may be e.g. an ultraviolet LED, wherein the peak wavelength $\lambda_{EXMAX}$ may be e.g. substantially equal to 380 nm, and the cutoff wavelength $\lambda_{EXMAX}$ may be e.g. substantially equal to 390 nm.

Figure 7A:
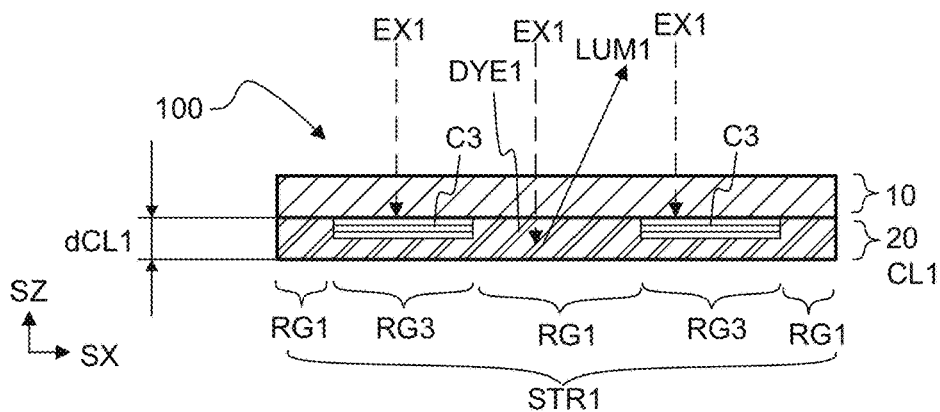
FIG. 7a shows, by way of example, in a cross-sectional view, a label which comprises filtering mask regions.
Figure 7B:
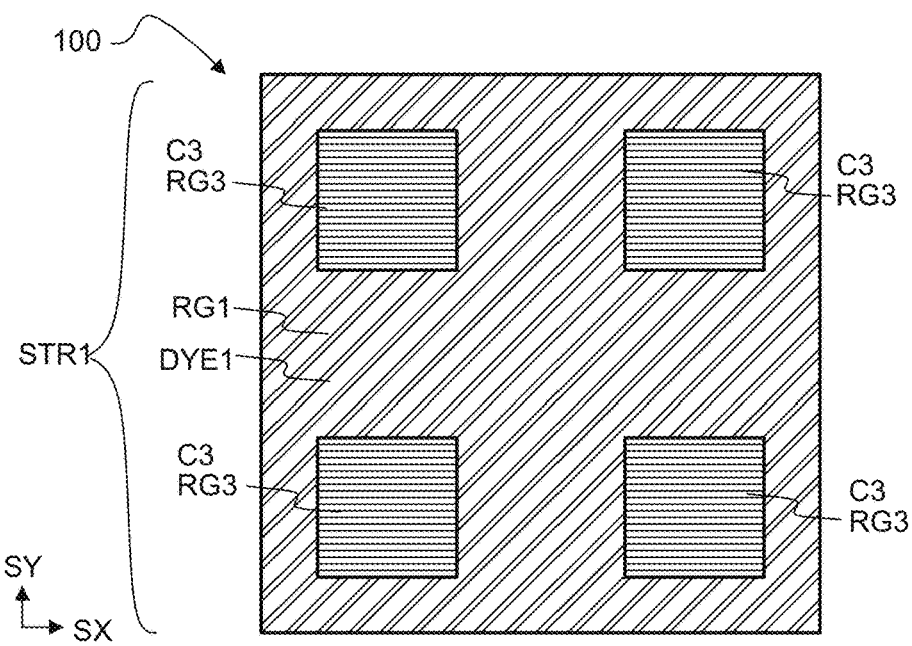
FIG. 7b shows, by way of example, in a top view, the label of FIG. 7a, FIG. 7c shows, by way of example, an image of the label of FIG. 7a, in a situation where the label is illuminated with excitation light.

Referring to FIGS. 7a and 7b, the label 100 may comprise a radiance modulating structure STR1. The radiance modulating structure STR1 may spatially modulate the radiance of the fluorescence light LUM1.

The modulating structure STR1 may comprise e.g. one or more filter regions C3. The filter regions C3 may attenuate or prevent propagation of the excitation light EX1 to the fluorescent layer CL1 of the label 100, wherein the filter regions C3 may allow transmission of the emitted fluorescence light LUM1. The filter regions C3 may be e.g. optical longpass filters or band rejection filters.

The modulating structure STR1 may comprise exposed regions RG1 and covered regions RG3. The excitation light EX1 may interact with the fluorescent substance DYE1 in the exposed regions RG1. The regions RG3 are covered with the mask filters C3, which attenuate or prevent propagation of the excitation light EX1 to the fluorescent substance DYE1.

The label 100 may comprise a carrier layer 10 and an adhesive layer 20. The filtering regions C3 may be located e.g. between the carrier layer 10 and the adhesive layer 20. The regions C3 may be applied e.g. by printing. The label 100 may comprise a layer of fluorescent medium DYE1 beneath the filtering regions C3. The adhesive layer 20 may comprise fluorescent medium DYE1. The filter regions C3 may be located above the fluorescent layer.

The fluorescent layer CL1 may have a thickness $d_{CL1}$. The thickness $d_{CL1}$ of the fluorescent layer CL1 may be e.g. in the range of 1 µm to 200 µm.

The filter regions C3 may be implemented e.g. by printing an optically filtering ink. The filter regions C3 may be implemented e.g. by applying optically filtering polymer regions to the structure STR1.

Figure 7C:
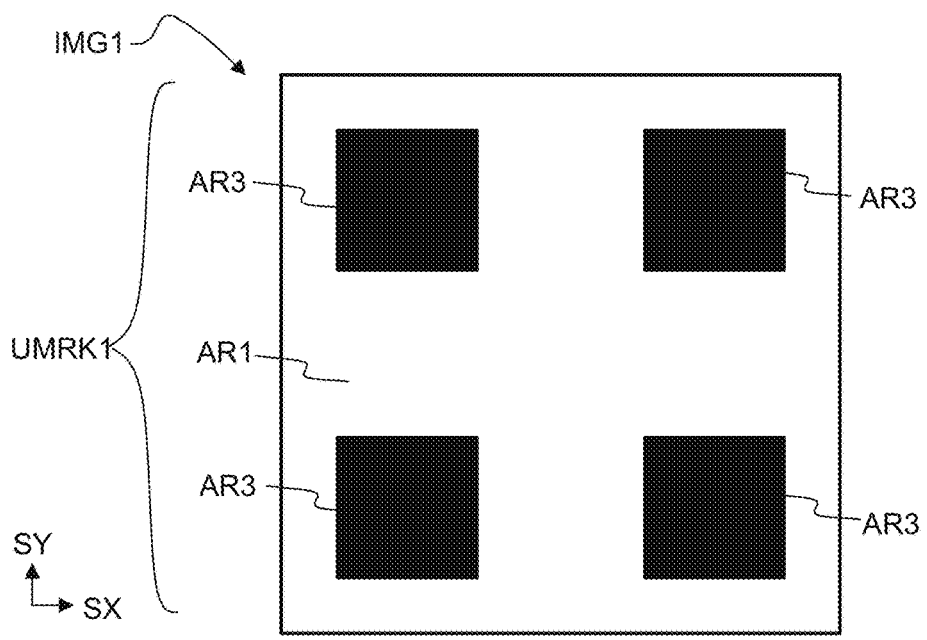
FIG. 7d shows, by way of example, spectral transmittance of a filtering mask region.

Referring to FIG. 7c, the modulating structure STR1 may provide a machine-detectable pattern UMRK1, when illuminated with the excitation light EX1, and when detected by the camera CAM1. The covered regions RG3 may appear as dark regions AR3 in the captured image IMG1. The exposed region RG1 may appear as a bright region AR1 in the captured image IMG1.

Figure 7D:
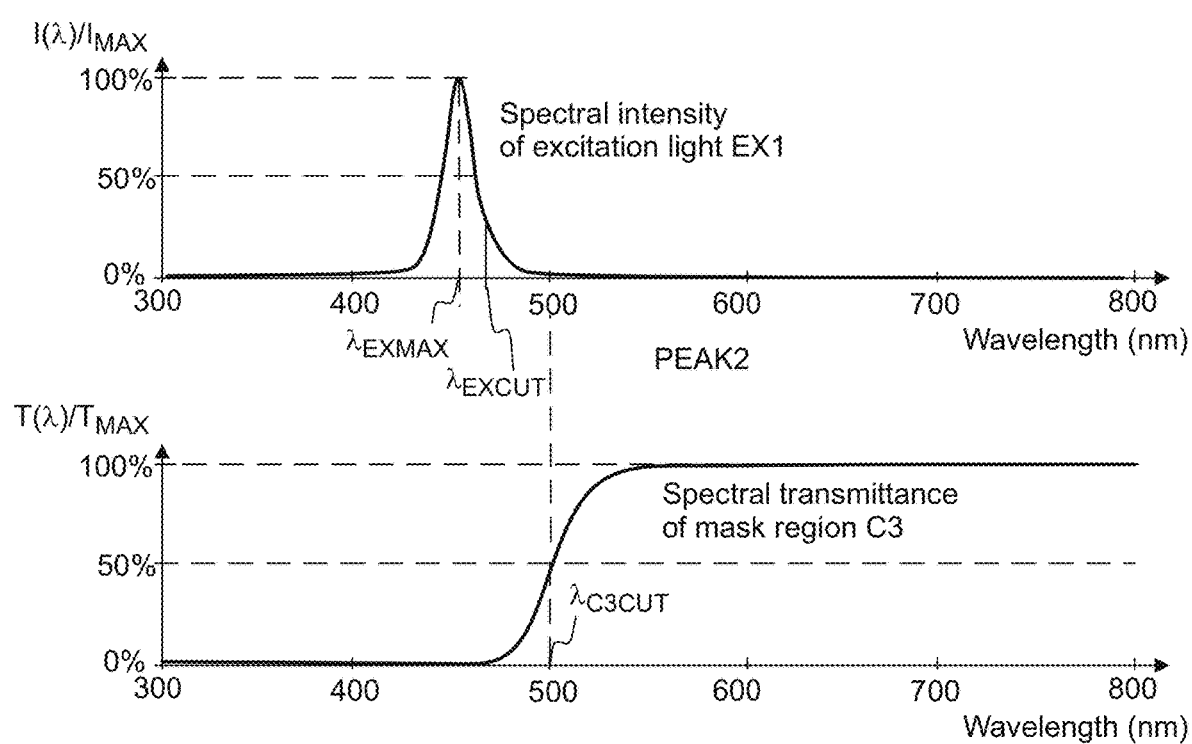
Figure 8A:
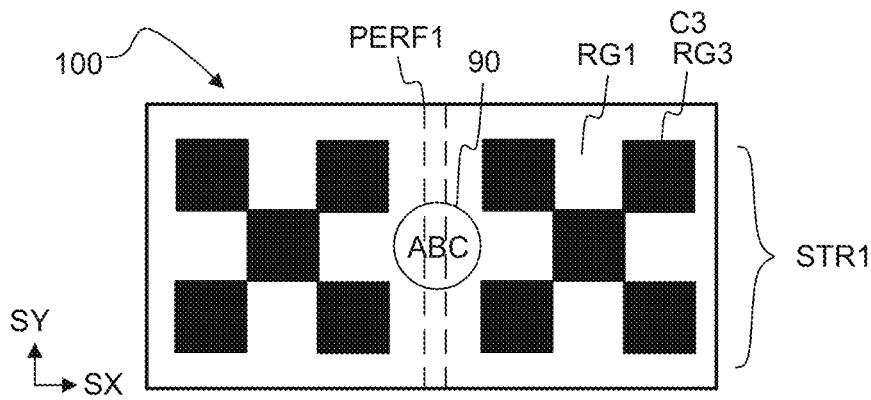
FIG. 8a shows, by way of example, in a top view, a label which comprises a modulating structure.
Figure 8B:
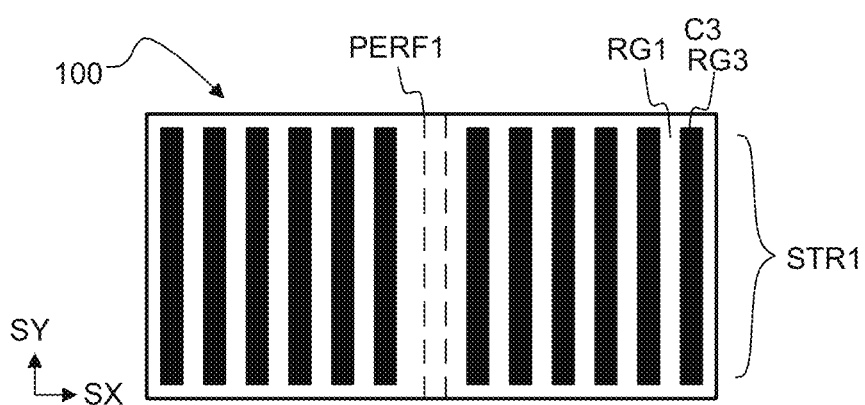
FIG. 8b shows, by way of example, in a top view, a label which comprises a modulating structure.
Figure 8C:
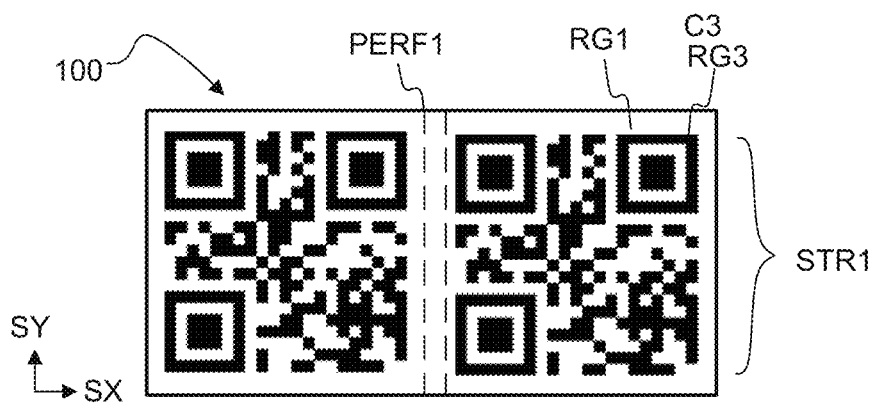
FIG. 8c shows, by way of example, in a top view, a label which comprises a modulating structure.
Figure 8D:
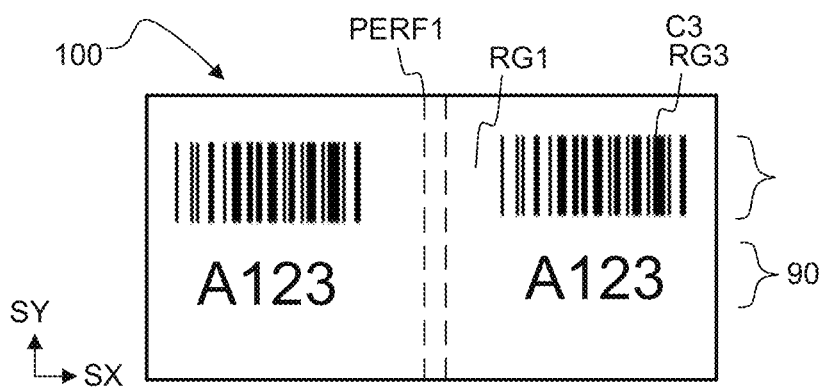
FIG. 8d shows, by way of example, in a top view, a label which comprises a modulating structure.

FIG. 7d shows, by way of example, spectral transmittance of a filter region C3. The filter region C3 may be e.g. a long pass filter, which attenuates or prevents transmission of the excitation light EX1, wherein the filter region C3 may allow transmission of the fluorescence light LUM1.

The filter regions C3 may also be ultraviolet-blocking filters, which may have spectral transmittance $T(\lambda)$ greater than 80% in the wavelength range 460 nm to 700 nm, and which may have spectral transmittance $T(\lambda)$ lower than 20% at wavelengths shorter than 400 nm.

Referring to FIGS. 8a to 8d, the modulating structure STR1 of the label 100 may be selected to provide a pattern. The pattern may be e.g. a target pattern and/or the pattern may represent a code.

The pattern may be provided e.g. by one or more of the following ways:
by spatial modulation of fluorescence yield (e.g. by spatial modulation of concentration of fluorescent substance and/or by spatial modulation of thickness of fluorescent layer).
by spatial modulation of transmittance of an optically filtering layer at a wavelength of the excitation light, wherein the optically filtering layer may be positioned above the fluorescent layer, and/or
by spatial modulation of out-coupling efficiency The pattern UMRK1 may be e.g. target pattern, which may be easily and reliably recognized by machine vision.

The target pattern may be easily distinguished from a background, which may comprise e.g. a printed substrate of the package. The target pattern may be e.g. a checkerboard pattern or a stripe pattern so as to facilitate machine recognition.

The pattern UMRK1 may also carry information. The pattern may be a code. The code may be e.g. a one-dimensional barcode, a two-dimensional barcode (e.g. QR code), an alphanumeric code and/or a character string.

The label 100 may comprise one or more perforated lines PERF1 to facilitate opening of the package when the package is opened by the final customer. The position of the perforated line or lines PERF1 may substantially coincide with the position of the opening joint 201 of the package.

The perforated line PERF1 may also operate as an edge EDG1, which may couple fluorescence light out of a waveguiding layer of the label 100 (see FIG. 15a).

The label 100 may further comprise a visually detectable indicator marking 90, which may be easily detected when viewed with the naked eye in normal white light, which does not contain ultraviolet light. The indicator marking 90 may be e.g. a conventional printed marking or a hologram. The indicator marking 90 may represent e.g. a trade mark associated with the product. An intact indicator marking 90 may visually indicate that the label 100 is a genuine label.

Figure 9A:
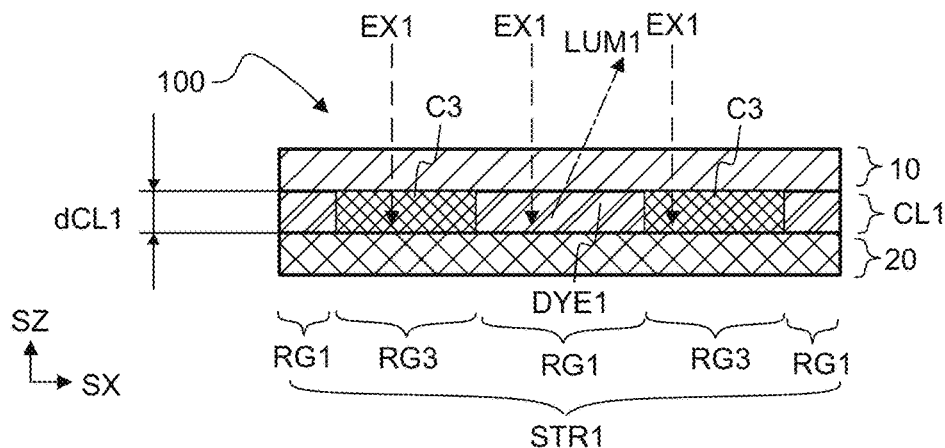
FIG. 9a shows, by way of example, in a cross-sectional view, a label which comprises non-fluorescent regions.
Figure 9B:
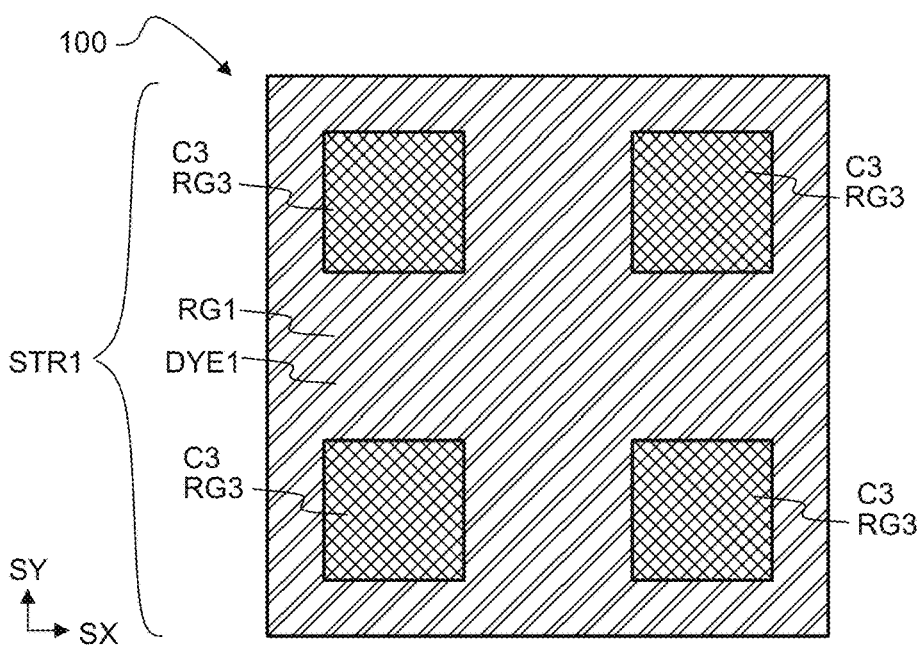
FIG. 9b shows, by way of example, in a top view, the label of FIG. 9a, FIG. 9c shows, by way of example, an image of the label of FIG. 9a, in a situation where the label is illuminated with excitation light.

Referring to FIGS. 9a and 9b, the modulating structure STR1 may comprise fluorescing regions RG1 and non-fluorescing regions RG3. The concentration of the fluorescent substance DYE1 in the non-fluorescing regions RG3 may be substantially lower than the concentration of the fluorescent substance DYE1 in the fluorescing regions RG1.

For example, the bottom side of the carrier layer 10 may be printed with fluorescent material, wherein the spaces remaining between the fluorescent regions may be filled with non-fluorescing material. Both regions RG1, RG3 may be substantially transparent when viewed with the naked eye in normal white light, which does not contain ultraviolet light.

Figure 9C:
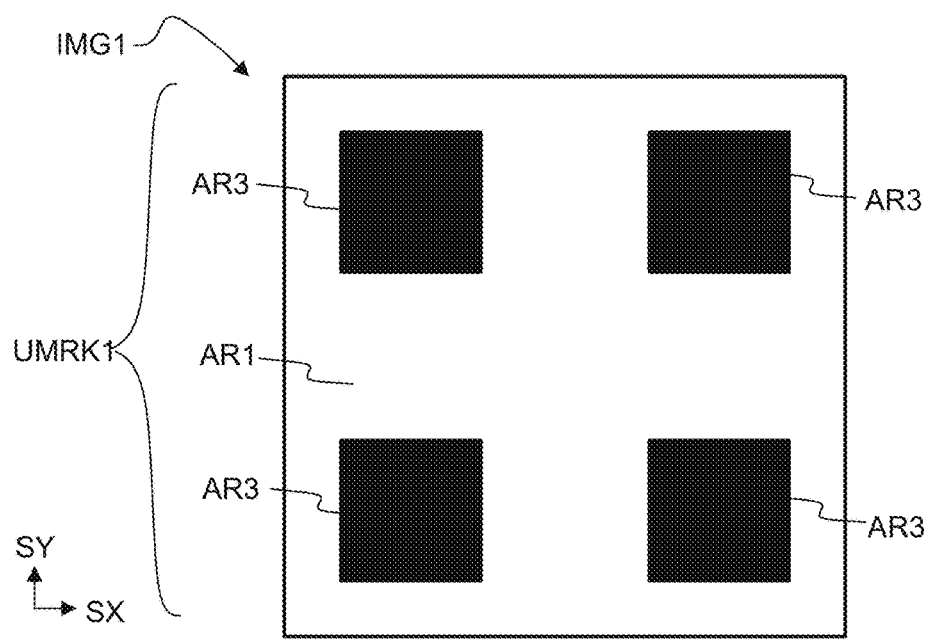

Referring to FIG. 9c, the modulating structure STR1 of FIG. 9a may provide a machine-detectable pattern UMRK1, when illuminated with the excitation light EX1, and when detected by the camera CAM1. The non-fluorescing regions RG3 may appear as dark regions AR3 in the captured image IMG1. The fluorescing region RG1 may appear as a bright region AR1 in the captured image IMG1.

Figure 10A:
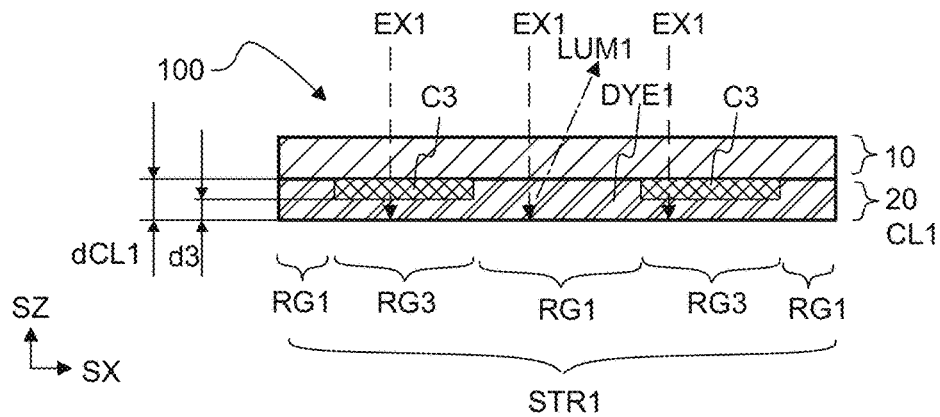
FIG. 10a shows, by way of example, in a cross-sectional view, a label where the fluorescent layer has a first thickness at a first transverse position and a second different thickness at a second transverse position.
Figure 10B:
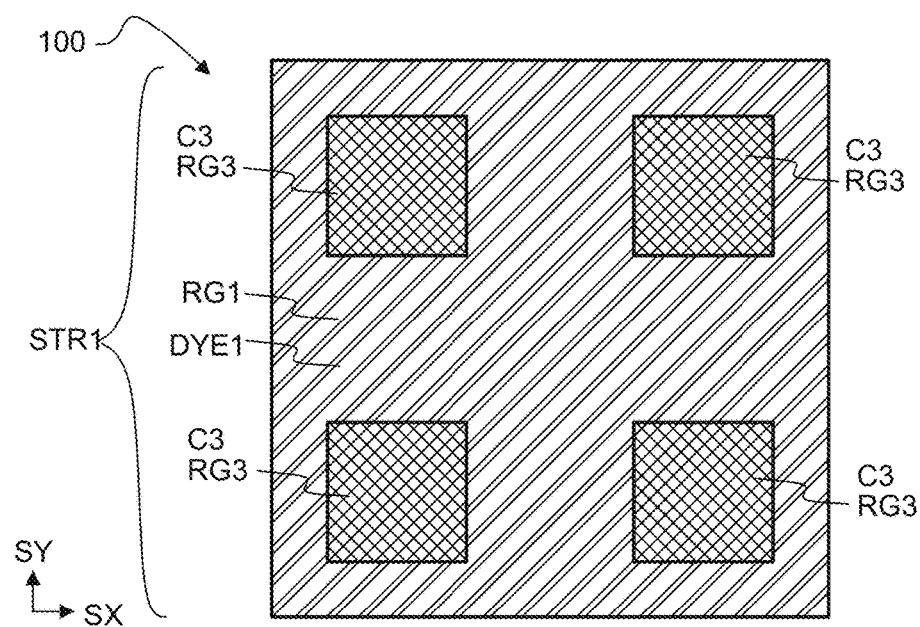
FIG. 10b shows, by way of example, in a top view, the label of FIG. 10a, FIG. 10c shows, by way of example, an image of the label of FIG. 10a, in a situation where the label is illuminated with excitation light.

Referring to FIGS. 10a and 10b, the modulating structure STR1 may comprise a fluorescent layer CL1, which has varying thickness. The fluorescent layer may have a first thickness ($d_{CL1}$) at a first transverse position and a second thickness (d3) at a second transverse position.

The transverse position may be specified e.g. by coordinates x,y, wherein the coordinate x may indicate position in the direction SX, and the coordinate y may indicate position in the direction SY.

The label 100 may comprise transparent filler regions C3 so as to provide constant total thickness for the modulating structure STR1. The varying thickness of the fluorescent layer may be provided e.g. by printing the filler regions C3 or by applying transparent plastic film to the regions RG3. For example, the bottom side of the carrier layer 10 may be printed with non-fluorescing material, wherein the spaces remaining between the non-fluorescing regions may be filled with fluorescing material.

Figure 10C:
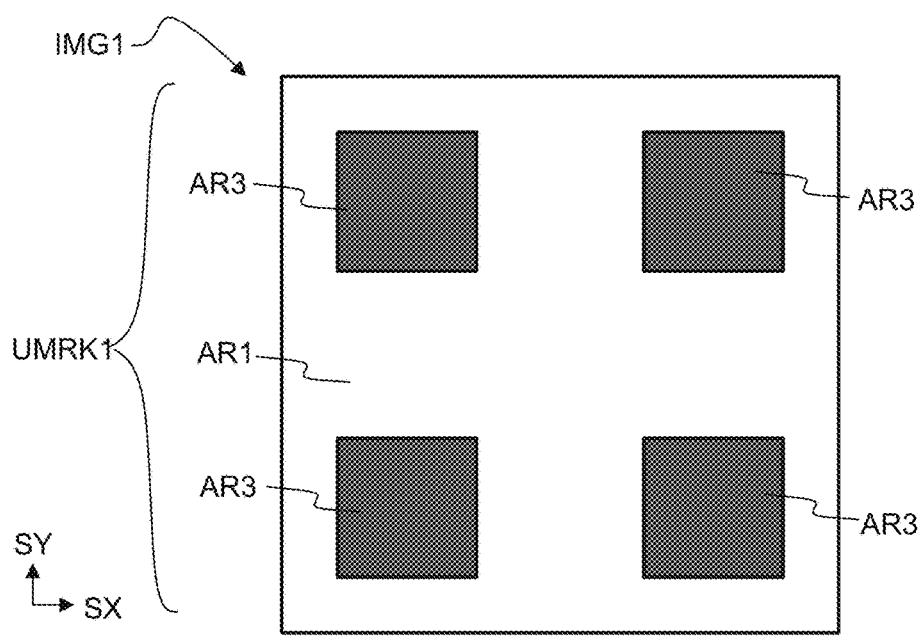

Referring to FIG. 10c, the modulating structure STR1 of FIG. 10a may provide a machine-detectable pattern UMRK1, when illuminated with the excitation light EX1, and when detected by the camera CAM1. The thinner regions RG3 may appear as darker regions AR3 in the captured image IMG1, wherein the thicker regions RG1 may appear as brighter regions AR1 in the image IMG1.

Figure 11A:
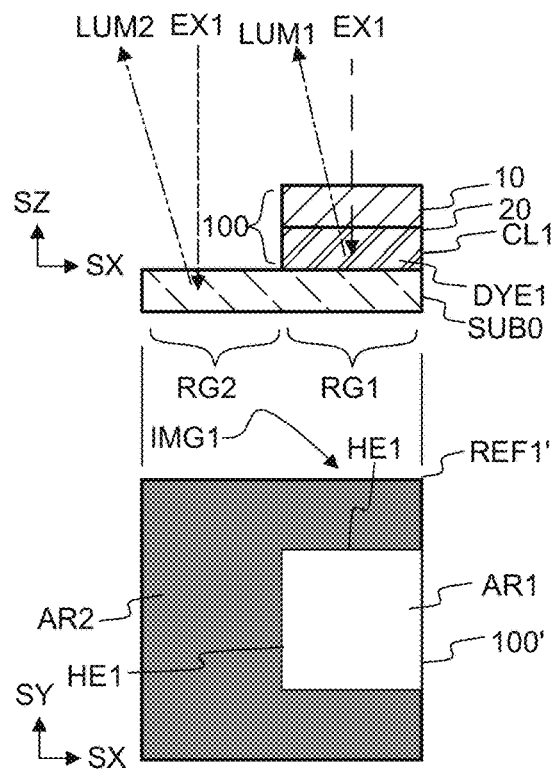
FIG. 11a shows, by way of example, operation of a label which comprises a homogeneous fluorescent layer.

Referring to FIG. 11a, the label 100 may comprise a carrier layer 10 and an adhesive layer 20. The adhesive layer 20 may comprise fluorescent substance DYE1. The adhesive layer 20 may emit fluorescence light LUM1 when illuminated with the excitation light EX1. Consequently, the image 100' of the label 100 may appear brighter than the image AR2 of the uncovered substrate SUB0 in the captured image IMG1. The common boundary of the partial images 100', AR2 may be easily detected as a high contrast edge HE1. The position of the edge HE1 may be detected by analyzing the image IMG1 with machine vision.

The substrate SUB0 of the package 200 may be fluorescent or non-fluorescent. The substrate SUB0 may comprise a fluorescent substance. The fluorescent substance of the substrate SUB0 may be different from the fluorescent substance DYE1 of the label 100. The substrate SUB0 may emit fluorescence light LUM2 when illuminated with the excitation light EX1. The spectrum of the fluorescence light LUM2 emitted from the substrate SUB0 may be different from the spectrum of the fluorescence light LUM1 emitted from the label 100. The fluorescent substance DYE1 of the label may be selected such that the spectrum of the fluorescence light LUM1 is different from the spectrum of the fluorescence light LUM2, so as to provide sufficient contrast between the label 100 and the substrate SUB0 in the captured image IMG1. The contrast between the label 100 and the substrate SUB0 in the captured image IMG1 may also be improved e.g. by using an optical filter FIL1, which suppresses the intensity of the fluorescence light LUM2, when compared with the intensity of the fluorescence light LUM1. The filter FIL1 may be positioned e.g. between the label 100 and the camera CAM1.

Figure 11B:
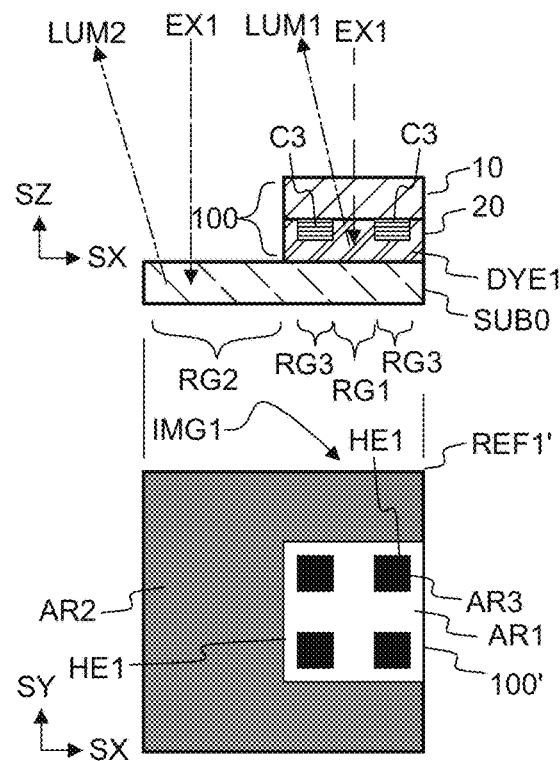
FIG. 11b shows, by way of example, operation of a label which comprises optically filtering mask elements.

Referring to FIG. 11b, the conversion efficiency of the label 100 may be spatially modulated e.g. by providing one or more modulating regions C3. The spatial modulation may provide a pattern UMRK1, which may be easily detected by analyzing the captured image IMG1 when the label is illuminated with the excitation light EX1, wherein the pattern may be substantially transparent when viewed with the naked eye in normal white light, which does not contain ultraviolet light. The filtering regions C3 may be e.g. optical longpass filters, which may e.g. allow propagation of red light and prevent propagation of blue light. The filtering regions C3 may be e.g. optical longpass filters, which may e.g. allow propagation of white light and prevent propagation of ultraviolet light.

The label 100 may comprise regions RG1, RG3. The region RG3 may denote a region which completely overlaps a filtering region C3. The region RG1 may denote a region which does not overlap a filtering region C3. RG2 may denote an uncovered region of the substrate SUB0 of the package.

The image IMG1 may comprise partial images AR1, AR2, AR3. The image AR1 may be an image of the region RG1. The image AR2 may be an image of the region RG2. The image AR3 may be an image of the region RG3.

The common boundary between the regions RG1, RG3 may be detected as an edge HE23 between the partial images AR1, AR3. The common boundary between the regions RG1, RG3 may be detected as a high contrast edge HE1 in the image IMG1.

The common boundary between the regions RG1, RG2 may be detected as an edge HE1 between the partial images AR1, AR2. The common boundary between the regions RG1, RG1 may be detected as a high contrast edge HE1 in the image IMG1.

Figure 11C:
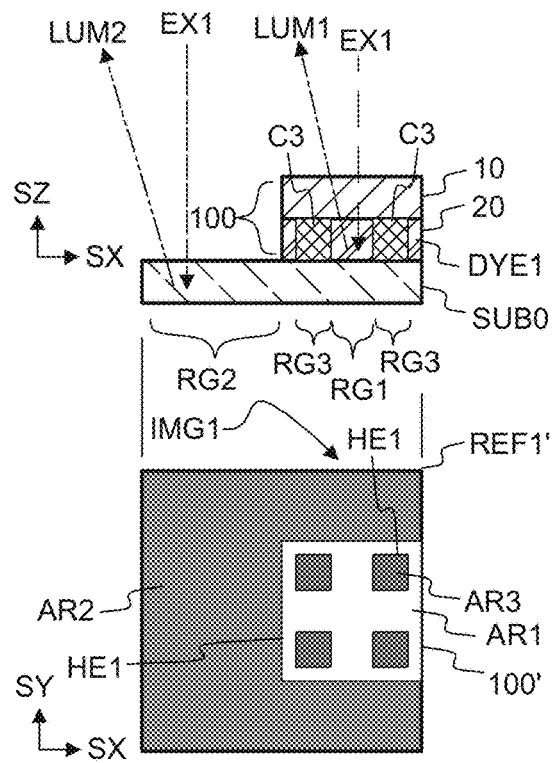
FIG. 11c shows, by way of example, operation of a label which comprises non-fluorescent regions.

Referring to FIG. 11c, the modulating regions C3 of the structure STR1 may also be implemented by varying the thickness of the fluorescent layer and/or by varying the concentration of the fluorescent substance DYE1 in a fluorescent layer.

Figure 11D:
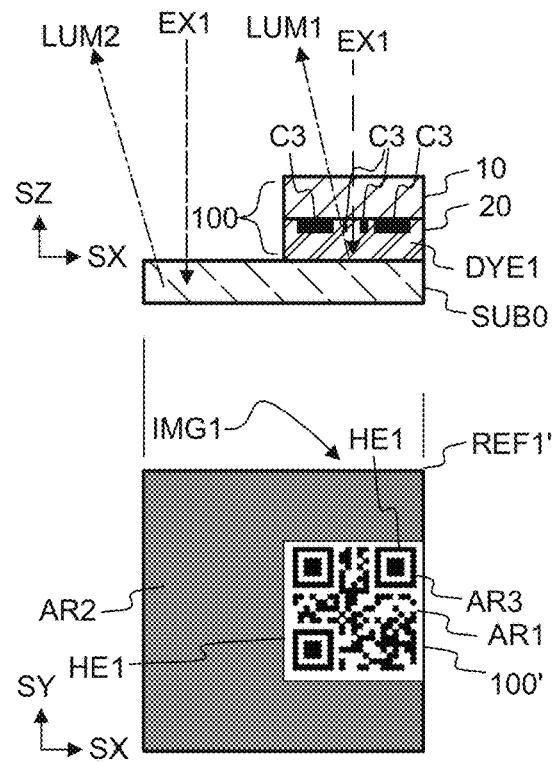
FIG. 11d shows, by way of example, operation of a label which is arranged to provide a machine-detectable pattern.

Referring to FIG. 11d, the modulating regions C3 of the label 100 may provide a pattern UMRK1. The pattern UMRK1 may be detected in the captured image IMG1 when the label is illuminated with the excitation light EX1, wherein the pattern UMRK1 may be substantially transparent when viewed with the naked eye in normal white light, which does not contain ultraviolet light.

Figure 12A:
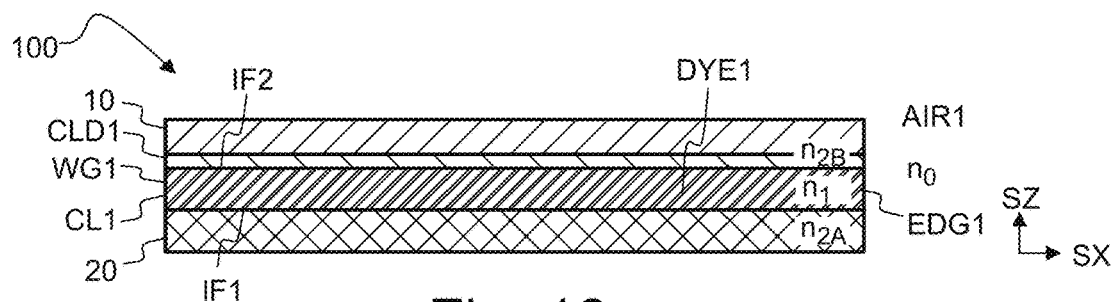
FIG. 12a shows, by way of example, in a cross-sectional view, a label, which comprises a waveguiding fluorescent layer.

Referring to FIG. 12a, the label 100 may comprise a waveguiding conversion layer WG1. The waveguiding layer may comprise a fluorescent substance DYE1. The label 100 may be arranged to operate such that at least a part of the fluorescence light LUM1 may be confined to the waveguiding layer by total internal reflection (TIR). The waveguiding layer may be defined by a first interface IF1 and by a second interface IF2. The refractive index $n_1$ of the waveguiding layer may be higher than the refractive index $n_{2A}$ of the material layer below the waveguiding layer so as to enable total internal reflection at the first interface IF1. The refractive index $n_1$ of the waveguiding layer may be higher than the refractive index $n_{2B}$ of the substance above the waveguiding layer so as to enable total internal reflection at the second interface IF2.

For example, the label 100 may comprise a carrier layer 10, a cladding layer CLD1, a waveguiding conversion layer WG1, and an adhesive layer 20. The waveguiding layer WG1 may be located between the cladding layer CLD1 and the adhesive layer 20. The cladding layer CLD1 may be located between the carrier layer 10 and the waveguiding layer WG1. The refractive index $n_{2A}$ of the adhesive layer 20 and the refractive index n2B of the cladding layer CLD1 may be lower than the refractive index $n_1$ of the waveguiding conversion layer WG1. The waveguiding conversion layer WG1 may comprise a fluorescent substance DYE1.

Figure 12B:
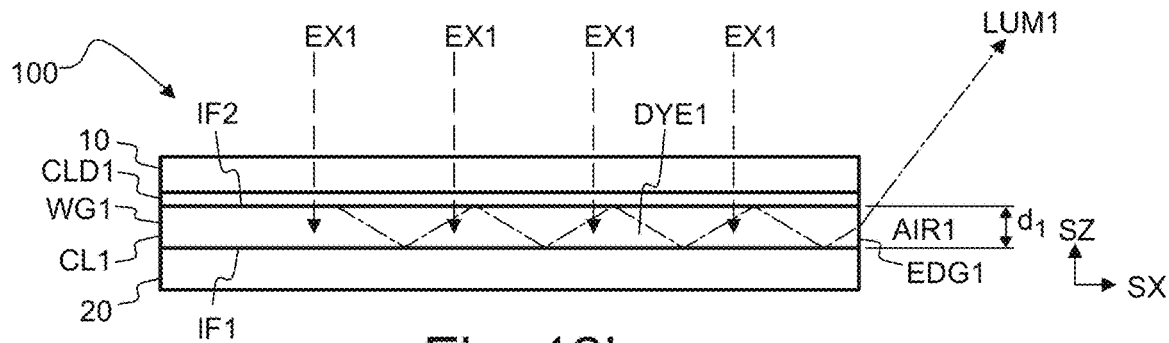
FIG. 12b shows, by way of example, in a cross-sectional view, coupling light out of the waveguiding fluorescent layer via an edge of the label.

Referring to FIG. 12b, at least a part of the fluorescence light LUM1 may propagate along the waveguiding conversion layer WG1. The waveguided fluorescence light LUM1 may be coupled out of the label 100 e.g. through an edge EDG1 of the waveguiding conversion layer WG1. A camera CAM1 may be arranged to form the image IMG1 by focusing light, which is coupled out of the edge EDG1. The image IMG1 may comprise a partial image of the edge EDG1 of the label 100. The partial image of the edge EDG1 may be brighter than the surrounding areas of the image IMG1, when the label 100 is illuminated with the excitation light EX1.

Figure 12C:
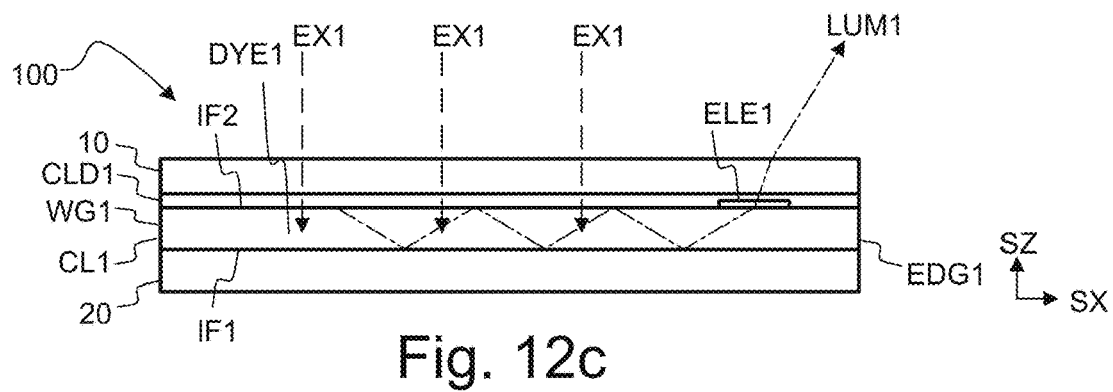
FIG. 12c shows, by way of example, in a cross-sectional view, coupling light out of the waveguiding fluorescent layer by using an out-coupling element.
Figure 12D:
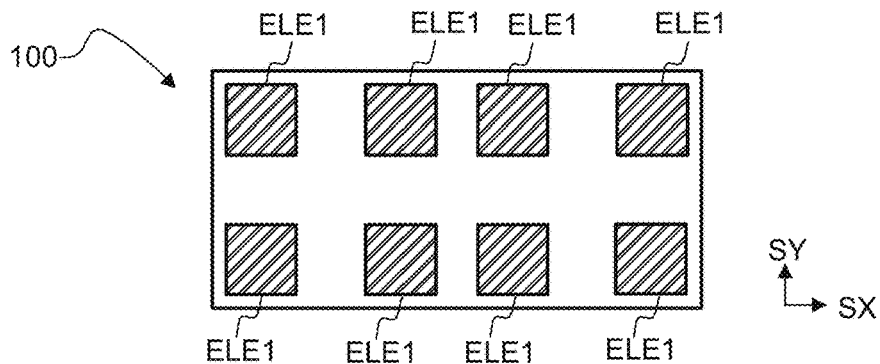
FIG. 12d shows, by way of example, in a top view, a label, which comprises out-coupling elements.

Referring to FIGS. 12c and 12d, the label 100 may comprise one or more out-coupling elements ELE1, which may be arranged to couple fluorescence light LUM1 out of the waveguiding conversion layer. The out-coupling element ELE1 may be e.g. a light-scattering element or a diffractive element. A light-scattering element ELE1 may be e.g. a rough portion of the interface IF1 or IF2. A light-scattering element ELE1 may formed e.g. by adding light-scattering particles to a selected region of the waveguiding conversion layer. A diffractive out-coupling element ELE1 may be e.g. a diffraction grating. The grating constant of the grating and/or the orientation of diffractive features of the grating may be selected so as to direct the out-coupled light LUM1 towards the camera CAM1.

The label 100 may comprise one or more out-coupling elements ELE1, which may be arranged to operate as marker features. The monitoring apparatus 500 may be arranged to determine the position of the label 100 by detecting the position of one or more marker features of the label 100. The out-coupling elements ELE1 may appear as bright areas in a captured image IMG1.

The out-coupling elements ELE1 of the label 100 may be arranged to provide a pattern UMRK1. The pattern may be target pattern for machine recognition and/or the pattern may carry information.

Figure 13:
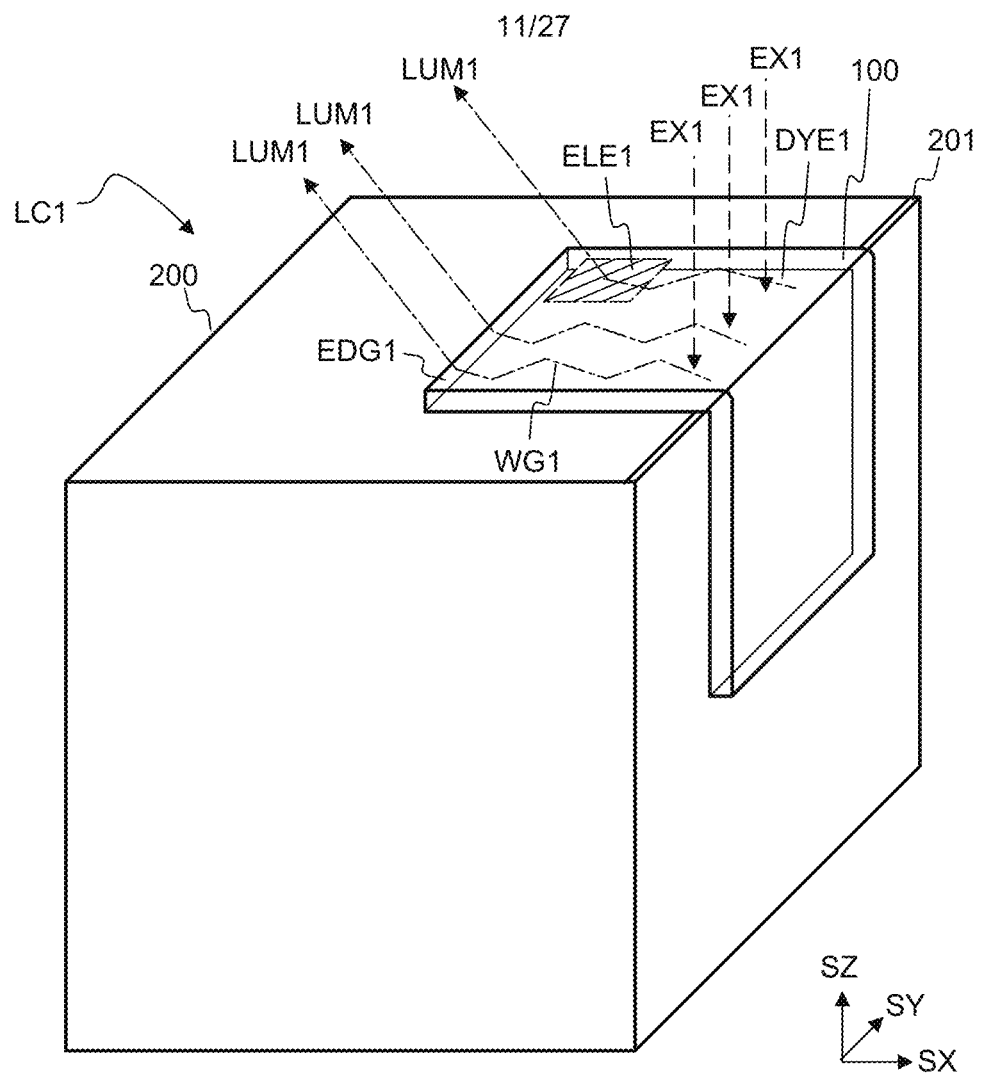
FIG. 13 shows, by way of example, in a three-dimensional view, generating fluorescence light within a waveguiding layer, and coupling waveguided fluorescence light out of the waveguiding layer.

Referring to FIG. 13, the fluorescent substance DYE1 may emit fluorescence light LUM1 when illuminated with the excitation light EX1. A part of light LUM1 emitted in a waveguiding conversion layer WG1 may propagate within the waveguiding conversion layer WG1. The propagating light LUM1 may be coupled out of the waveguiding conversion layer WG1 by an edge EDG1 of the label 100 and/or by an out-coupling element ELE1. The monitoring apparatus 500 may be arranged to detect the position of the EDG1 and/or the position of the out-coupling element ELE1 by analyzing an image IMG1 of the label 100. The monitoring apparatus 500 may be arranged to determine the position of the label 100 by detecting the position of the edge EDG1 and/or by detecting the position of the out-coupling element ELE1.

Figure 14A:
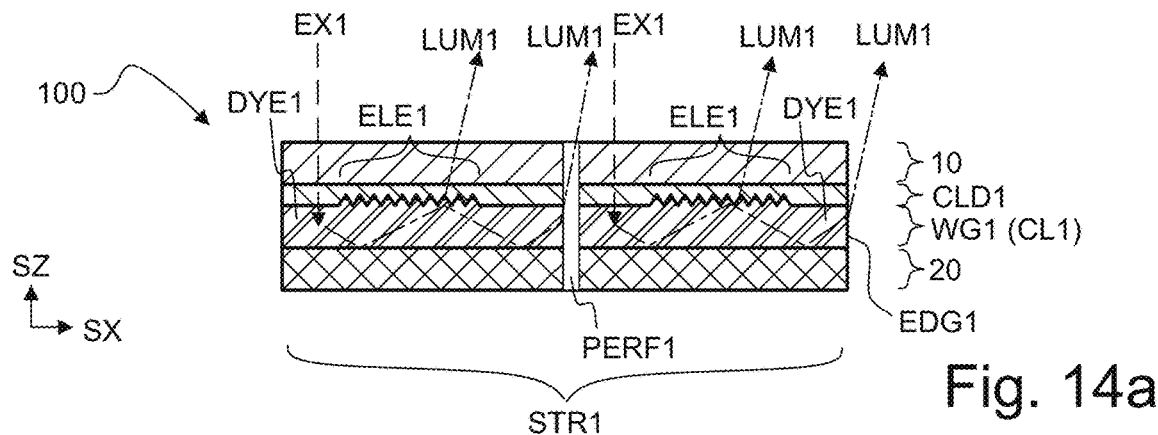
FIG. 14a shows, by way of example, in a cross-sectional view, a label which comprises a waveguiding fluorescent layer and out-coupling elements to couple light out of a waveguiding fluorescent layer.
Figure 14B:
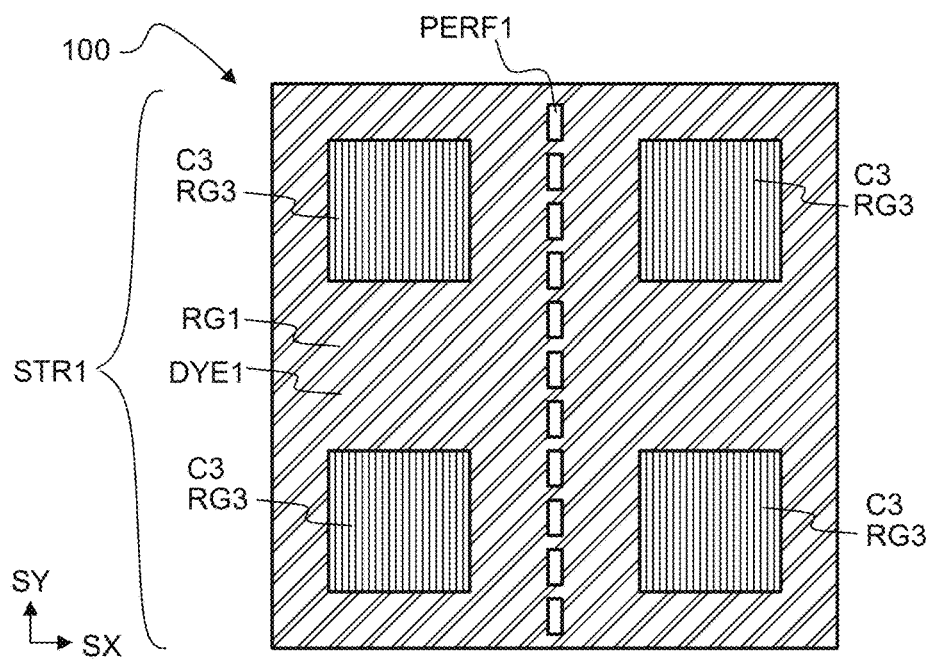
FIG. 14c shows, by way of example, an image of the label of FIG. 14a, in a situation where the label is illuminated with excitation light.

Referring to FIGS. 14 and 14b, the label 100 may comprise one or more out-coupling elements ELE1 to couple light out of the waveguiding fluorescent layer CL1. The modulating structure STR1 of the label 100 may comprise one or more out-coupling elements ELE1 to provide spatial modulation of radiance. The element ELE1 may be e.g. a diffractive or rough portion of the surface of the fluorescent layer CL1. The element ELE1 may be formed e.g. by embossing, by adding light-scattering particles to the fluorescent layer and/or by making one or more holes in the fluorescent layer CL1.

The label 100 may comprise one or more perforations PERF1. The perforation PERF1 may operate as a light-out-coupling edge EDG1.

Figure 14C:
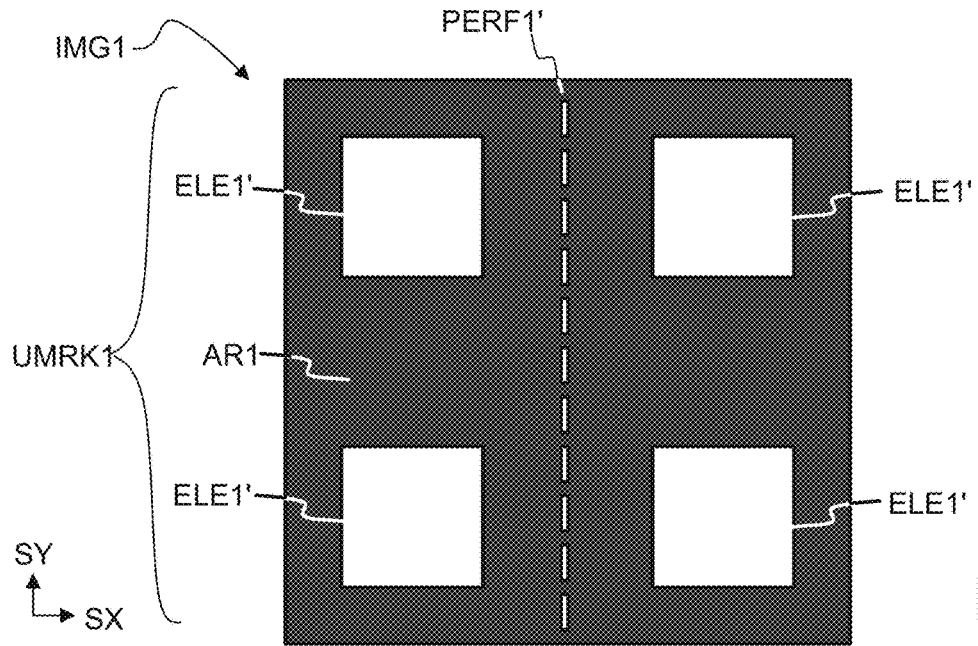

Referring to FIG. 14c, the out-coupling elements ELE1 and/or the perforation PERF1 may appear as bright partial images ELE1', PERF1' in the captured image IMG1.

Referring to FIG. 15a, the monitoring apparatus 500 may comprise a first light source LS1 to provide excitation light EX1 and a camera CAM1 to capture a first image IMG1 when the label 100 is illuminated with the excitation light EX1 at a time $t_1$. The light source LS1 may provide an excitation light pulse at a time $t_1$. The camera CAM1 may have a field of view VIEW1.

At least a part of the energy of the excitation light EX1 may converted into fluorescence light LUM1 in the waveguiding conversion layer WG1 of the label 100. The fluorescent substance DYE1 may emit fluorescence light LUM1 when illuminated with the excitation light EX1. At least a part of the luminescent light LUM1 may be confined to the waveguiding conversion layer WG1 by total internal reflection at the interfaces IF1, IF2. A part of the excitation light EX1 may be coupled out of the waveguiding conversion layer WG1 by an out-coupling element ELE1. The out-coupling element ELE1 may be e.g. a scattering element and/or a diffraction grating. A part of the excitation light EX1 may be coupled out of the waveguiding conversion layer WG1 through an edge EDG1 of the label 100. The camera CAM1 may be positioned such that the camera may form the image IMG1 by focusing the out-coupled light LUM1. The element ELE1, the perforation PERF1 and/or the edge EDG1 may appear as bright objects in the captured image IMG1.

The modulating structure STR1 of the label 100 may generate a pattern UMRK1. The generated pattern may appear in the captured image IMG1. The structure STR1 may comprise e.g. a waveguiding fluorescent layer, elements ELE1 and/or a perforation PERF1, and the generated pattern may comprise bright partial images ELE1' of the elements and a bright image PERF1' of the perforation PERF1.

The apparatus 500 may optionally comprise a second auxiliary light source LS2 to provide auxiliary illuminating light B0. The second light source LS2 may be arranged to provide auxiliary illuminating light B0. The spectrum of the auxiliary illuminating light B0 may be different from the spectrum of the excitation light EX1. The auxiliary illuminating light B0 may be e.g. white light for capturing a conventional photo IMG2 of the package 200. The light source LS2 may provide an auxiliary light pulse B0 at a time $t_2$. The camera CAM1 (or a second camera) may capture an image IMG2 when the package 200 is illuminated with the auxiliary light pulse B0 at a time $t_2$. The image IMG2 may comprise an image 200' of the package 200. The boundary of the package 200 may be easily detectable in the image IMG2.

The use of the second image IMG2 may facilitate detecting the position of the boundaries of the package 200. The apparatus 500 may be arranged to analyze both images IMG1, IMG2 in order to determine the position of the label 100 with respect to the package 200.

The images IMG1 and IMG2 may be captured by using the same camera CAM1, by illuminating the package 200 with a first light pulse (e.g. EX1) and by illuminating the package 200 with a second light pulse (e.g. B0).

The camera CAM1 may comprise one or more optical filters FIL1 to provide a desired spectral response.

The light source LS1 may comprise one or more optical filters FIL1 to provide a desired spectral intensity distribution for the excitation light EX1. The method may comprise using one or more optical filters to define spectral intensity distribution of the excitation light (EX1) impinging on the label.

The light sources LS1, LS2 may provide light in a pulsed or continuous manner. The use of pulsed light may e.g. allow time-multiplexed illumination of the label with different spectra, may allow short exposure time of the camera, may allow imaging of a moving package, may allow precise timing for capturing the image in case of the moving package, may reduce power consumption and/or may increase operating life of the light source.

Auxiliary imaging measurements may be performed by capturing an auxiliary image of the label 100 when the label 100 is illuminated with auxiliary light B0. The spectrum of the auxiliary light B0 may be selected such that the camera CAM1 may detect light (BOR) reflected from the label 100. The auxiliary light B0 may be e.g. white light or red light.

The position of the excitation light source LS1 may be selected such that light EX1 reflected from the label 100 is not directed towards the camera CAM1. The position of the excitation light source LS1 may be selected such that light EX1 reflected from the label 100 does not impinge on the camera CAM1. The auxiliary light source LS2 may be positioned such that the camera CAM1 may detect the light reflected from the label 100.

An air gap between the adhesive layer 20 and the substrate SUB0 may increase the reflection coefficient of the lowermost surface of the adhesive layer 20. The apparatus 500 may be arranged to monitor the reflection coefficient of the lowermost surface may measuring the intensity of light reflected from the lowermost surface of the label 100. The apparatus 500 may be arranged to check whether the adhesive layer 20 is properly attached to the substrate SUB0 of the package 200. The apparatus 500 may also be arranged to determine whether the label 100 attached to the package 200 is wrinkled or flat. Abnormal intensity of reflected light may indicate that label 100 is not flat.

In an embodiment, the same light source LS1 may be arranged to provide a first light pulse which has a first spectrum (of excitation light EX1) and a second light pulse which has a second spectrum (of auxiliary light B0). The spectrum of the light may be changed e.g. by using one or more optical filters.

Figure 15B:
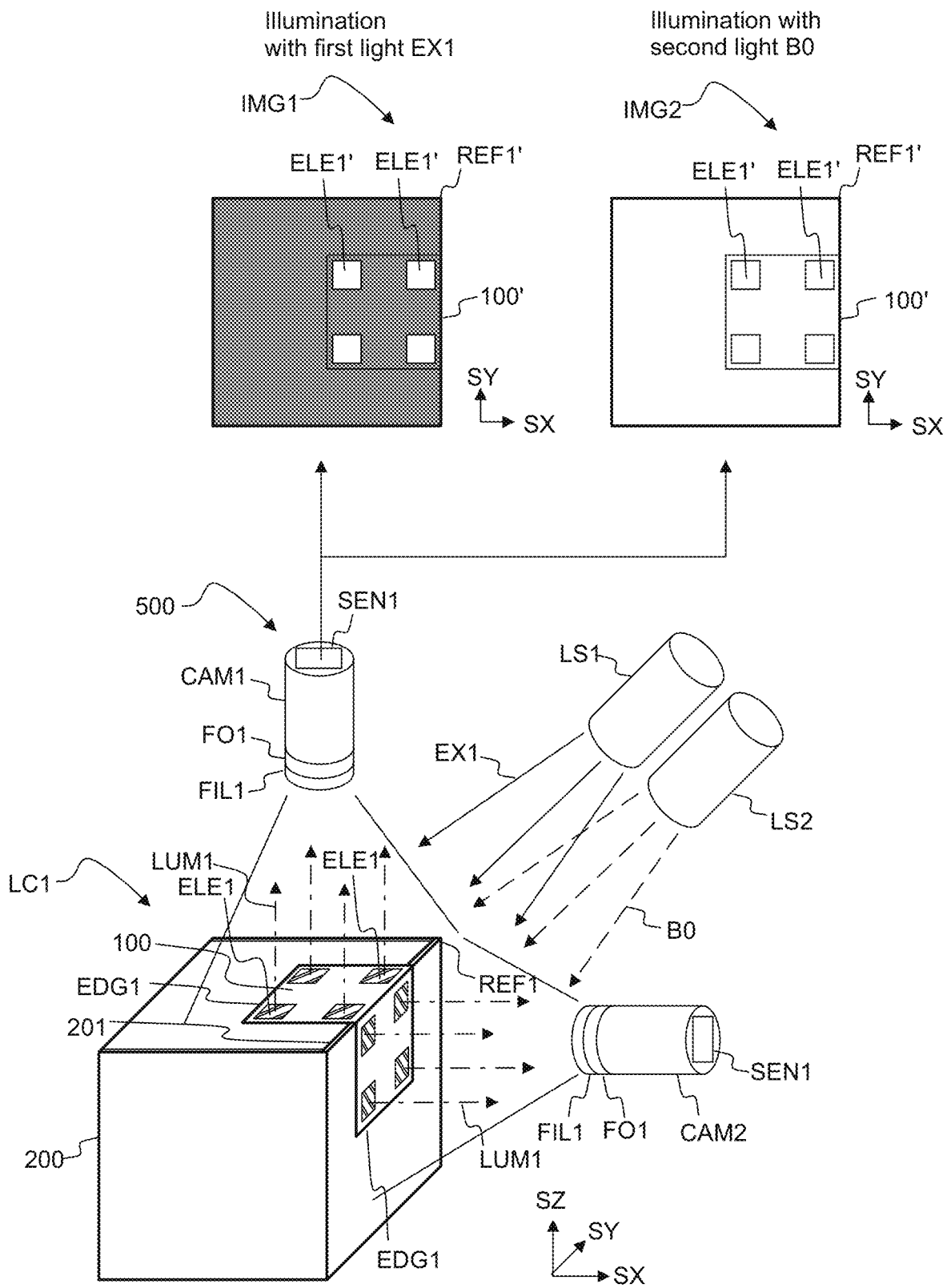
FIG. 15b shows, by way of example, monitoring the position of the label by using a monitoring apparatus.

Referring to FIG. 15b, the monitoring apparatus 500 may comprise one or more light sources LS1, LS2, and one or more cameras CAM1, CAM2. A first camera CAM1 may be arranged to capture a first image IMG1, which shows a first side of the package 200 when the label is illuminated with the excitation light EX1. The first camera CAM1 may be arranged to capture a second image IMG2, which shows a first side of the package 200 when the label is illuminated with the auxiliary light B0. A second camera CAM1 may be arranged to capture a second image, which shows a second side of the package 200.

Figure 16A:
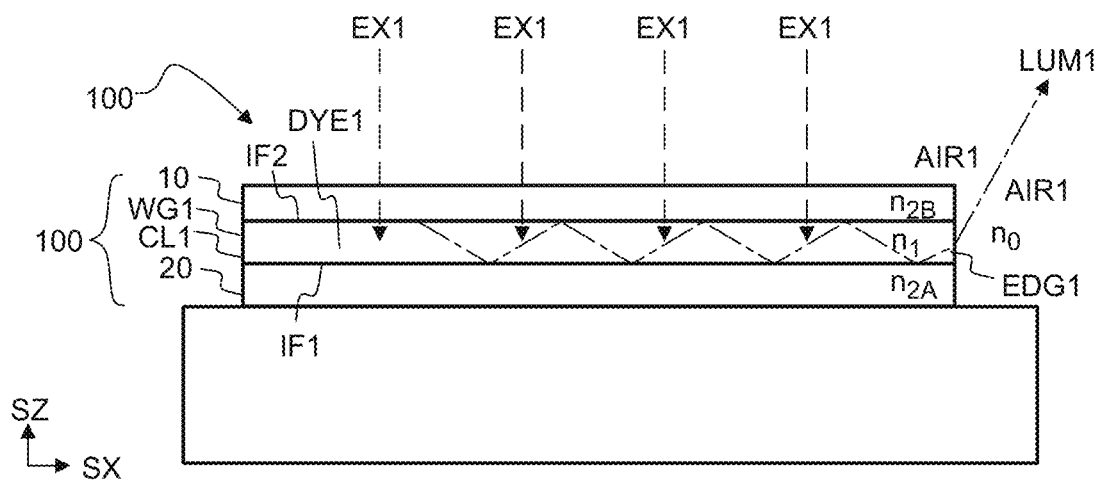
FIG. 16a shows, by way of example, in a cross-sectional view, a waveguiding fluorescent layer located between a carrier layer and an adhesive layer.

Referring to FIG. 16a, the label 100 may comprise a waveguiding layer WG1 defined by a first interface IF1 and by a second interface IF2. The first interface IF1 may be an interface between the waveguiding layer WG1 and a medium below the waveguiding layer WG1. The second interface IF2 may be an interface between the waveguiding layer WG1 and a medium above the waveguiding layer WG1. The first interface IF1 may be substantially planar and the second interface IF2 may be substantially planar. The waveguide WG1 may have a refractive index $n_1$. The medium below the waveguide WG1 may have a refractive index $n_{2A}$. The medium above the waveguide WG1 may have a refractive index $n_{2B}$. The refractive index difference $(n_1 - n_{2A})$ between the waveguide WG1 and the medium below the waveguide WG1 may be selected to provide total internal reflection (TIR1) at the first interface IF1 for fluorescence light LUM1 propagating in the waveguide WG1. The refractive index difference $(n_1 - n_{2B})$ between the waveguide WG1 and the medium above the waveguide WG1 may be selected to provide total internal reflection (TIR1) at the second interface IF2 for fluorescence light LUM1 propagating in the waveguide WG1.

The waveguide WG1 may be located between a first substantially planar interface IF1 and a second substantially planar interface IF2, wherein the first interface IF1 may provide total internal reflection for fluorescence light LUM1 propagating within the waveguide WG1, and the second interface IF2 provides total internal reflection for fluorescence light LUM1 propagating within the waveguide WG1.

The label 100 may comprise an intermediate waveguiding conversion layer WG1 (CL1), which may be located between the carrier layer 10 and the adhesive layer 20. The waveguiding conversion layer WG1 may be in contact with the carrier layer 10 and the adhesive layer 20. The refractive index of the intermediate layer WG1 may be higher than the refractive index of the carrier layer 10 and higher than the refractive index of the adhesive layer 20. The waveguided fluorescence light LUM1 may be coupled out by an edge EDG1 and/or by an out-coupling element ELE1.

The waveguiding layer or waveguide WG1 of the label 100 may be formed of one or more sub-layers. The fluorescent substance DYE1 may be distributed substantially evenly within the whole thickness of the waveguiding layer WG1. Alternatively, the fluorescent substance DYE1 does not need to be distributed over the whole thickness of the waveguiding layer WG1. The waveguiding layer WG1 may comprise e.g. a first sub-layer and a second sub-layer, wherein the composition of the first sub-layer may be different from the composition of the second sub-layers. In particular, the waveguiding layer WG1 may comprise a first fluorescent sub-layer, and a second non-fluorescent sub-layer.

Figure 16B:
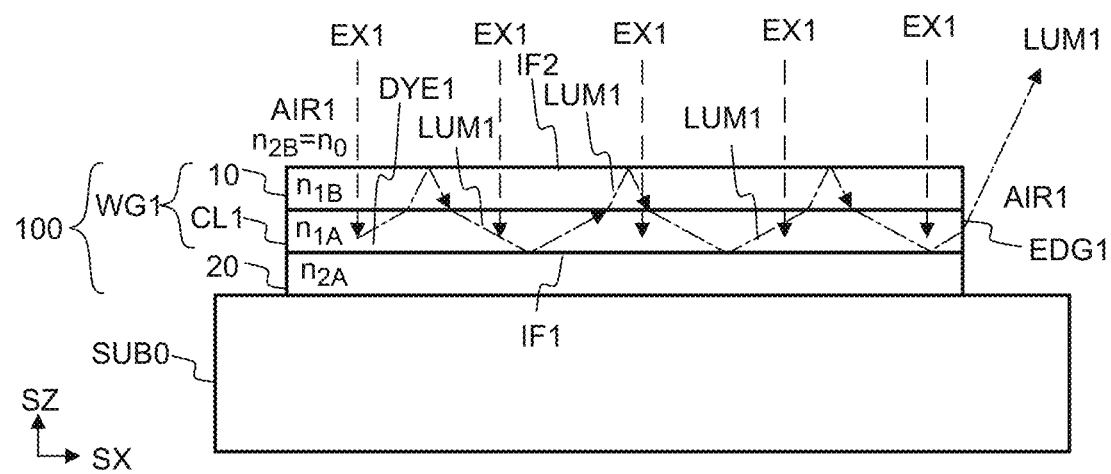
FIG. 16b shows, by way of example, in a cross-sectional view, a waveguide defined by ambient air and by an adhesive layer.

Referring to FIG. 16b, the label 100 may comprise a waveguide formed of one or more layers (e.g. 10, CL1). The waveguide WG1 may be a substantially planar waveguide. The label 100 may comprise a waveguiding layer WG1 formed of two or more sub-layers (e.g. 10, CL1). For example, the carrier layer 10 and a fluorescent intermediate layer CL1 may together form a waveguide WG1. The label 100 may comprise a fluorescent layer CL1 located between the carrier layer 10 and the adhesive layer 10. The fluorescent layer CL1 may comprise a fluorescent substance DYE1. The waveguide WG1 may be defined by a first interface IF1 and a second interface IF2. The first interface IF1 may be the interface between the fluorescent intermediate layer CL1 and the adhesive layer 20. The second interface IF2 may be the interface between the carrier layer 10 and the ambient air AIR1. A lower sub-layer of the waveguide WG1 may have a refractive index $n_{1A}$. An upper sub-layer of the waveguide WG1 may have a refractive index $n_{1B}$. The first interface IF1 may have a refractive index difference $n_{1A} - n_{2A}$. The second interface IF2 may have a refractive index difference $n_{1B} - n_{2B}$. $n_{2A}$ may denote the refractive index of the medium below the waveguide WG1. $n_{2B}$ may denote the refractive index of the medium above the waveguide WG1. The medium below the waveguide WG1 may be adhesive of the adhesive layer 20. The refractive index $n_{2A}$ may be equal to the refractive index of the adhesive layer 20. The medium above the waveguide WG1 may be ambient air AIR1. The refractive index $n_{2B}$ may be equal to the refractive index no of ambient air AIR1.

Figure 16C:
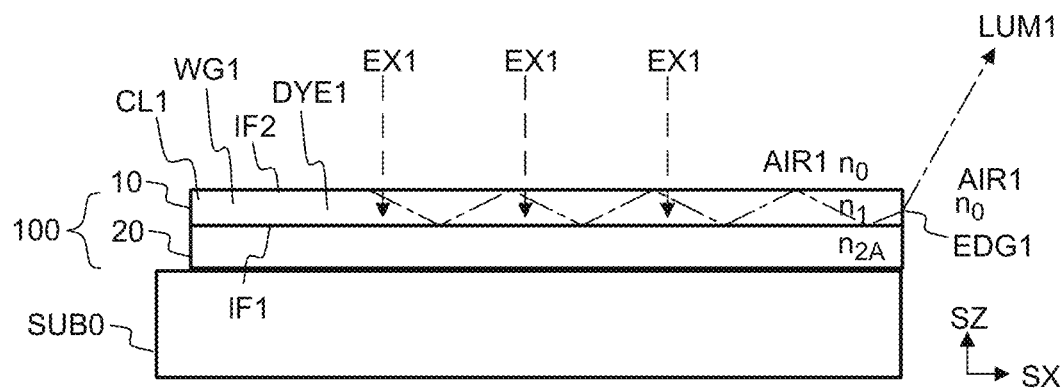
FIG. 16c shows, by way of example, in a cross-sectional view, a waveguiding layer defined by ambient air and by an adhesive layer.

Referring to FIG. 16c, the carrier layer 10 may operate as a waveguiding conversion layer WG1. The carrier layer 10 may comprise a fluorescent substance DYE1. The carrier layer 10 may be located between ambient air AIR1 and the adhesive layer 20. The refractive index of the carrier layer 10 may be higher than the refractive index of the adhesive layer 20 and higher than the refractive index of air AIR1. The waveguided fluorescence light LUM1 may be coupled out by an edge EDG1 and/or by an out-coupling element ELE1.

Figure 16D:
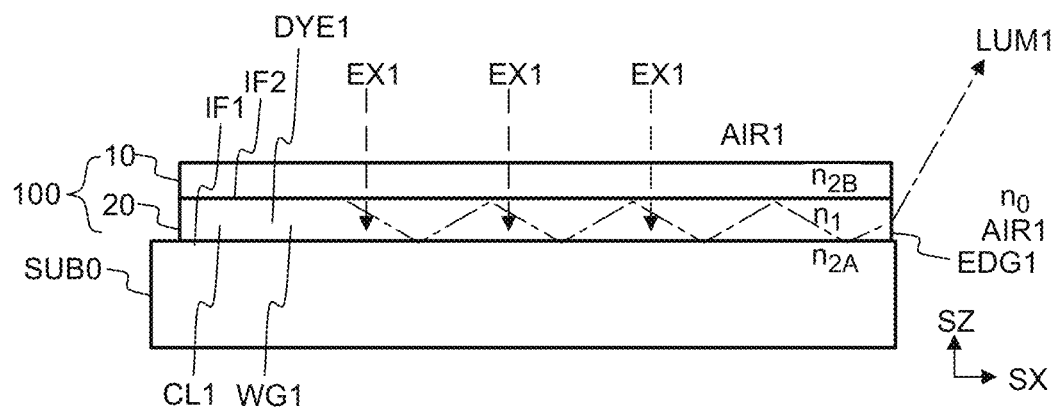
FIG. 16d shows, by way of example, in a cross-sectional view, a waveguiding fluorescent layer located between a carrier layer and the surface of the package.

Referring to FIG. 16d, the adhesive layer 20 may operate as a waveguiding conversion layer WG1. The adhesive layer 20 may comprise a fluorescent substance DYE1. The adhesive layer 20 may be located between the carrier layer 10 and the substrate SUB0 of the package 200. The refractive index of the adhesive layer 20 may be higher than the refractive index of the carrier layer 10 and higher than the refractive index of the substrate SUB0. The waveguided fluorescence light LUM1 may be coupled out by an edge EDG1 and/or by an out-coupling element ELE1.

The method may comprise detecting a degree of adhesion of the label 100 to the package 200, by analyzing the captured image IMG1. The method may comprise measuring the degree of adhesion of the label 100 to the package 200. The degree of adhesion of the label (100) may be measured by analyzing the captured image (IMG1). The degree of adhesion may be e.g. in the range of 0% to 100%. The value 0% may indicate that no part of the label is properly attached to the package. The value 100% may indicate that the adhesive layer of the label is fully in contact with the package. For example, a value 80% may indicate e.g. that the actual contact area is only 80% of the intended contact area.

Figure 16E:
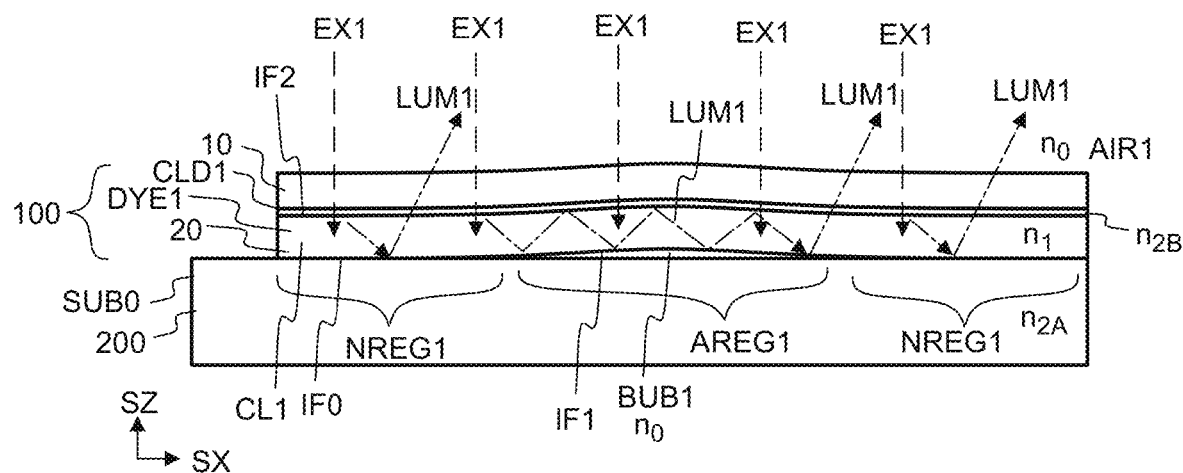
FIG. 16e shows, by way of example, in a cross-sectional view, a waveguiding region defined by an air bubble.

Referring to FIG. 16e, a waveguiding region may be used to indicate whether a label 100 is properly attached to a package 200. The label may also be arranged to operate such that it provides a waveguiding functionality only one or more regions which are not fully in contact with the package.

For example, the adhesive layer 20 of the label 100 may be arranged to operate as a waveguiding layer in a situation where a harmful air bubble BUB1 is trapped between the adhesive layer and the surface of the package 200.

A harmful air bubble BUB1 may sometimes remain trapped between the adhesive layer 20 of the label 100 and the surface of the package 200 after the label 100 has been attached to the package 200. The degree of adhesion of the label may be lower than 100% due to a trapped air bubble BUB1. The method may comprise measuring the degree of adhesion of the label by utilizing a waveguiding property of the label.

The materials of the label and/or the package may be selected such that refractive index of the adhesive layer may be lower than the refractive index of the surface of the package 200, at the wavelength of the fluorescence light. The adhesive layer 20 may have a normal region NREG1 where reflection coefficient of the lower surface of the adhesive layer 20 for fluorescence light LUM1 is low, due to an interface IF0 between the adhesive and the surface of the package 200. The same adhesive layer 20 may have an abnormal region AREG1 where the reflection coefficient of the lower surface of the adhesive layer 20 for fluorescence light LUM1 is high, due to an interface IF1 between the adhesive and the trapped air. The abnormal region AREG1 may provide total internal reflection (TIR) for fluorescence light LUM1 emitted from the label 100, whereas the normal region NREG1 does not provide total internal reflection for fluorescence light LUM1 emitted from the label 100. Consequently, the emitted fluorescence light LUM1 may be waveguided in the label 100 in the abnormal region, whereas the emitted fluorescence light LUM1 may effectively leak out of the label 100 at the abnormal region.

The label 100 may comprise a cladding layer CLD1 located between the carrier layer 10 and the adhesive layer 20. The refractive index $n_{2B}$ of the cladding layer CLD1 may be lower than the refractive index $n_1$ of the adhesive layer 20. Consequently, the abnormal region may operate as a waveguiding region also in a situation where the carrier layer is made of a material (e.g. plastic), which has a high refractive index.

Figure 16F:
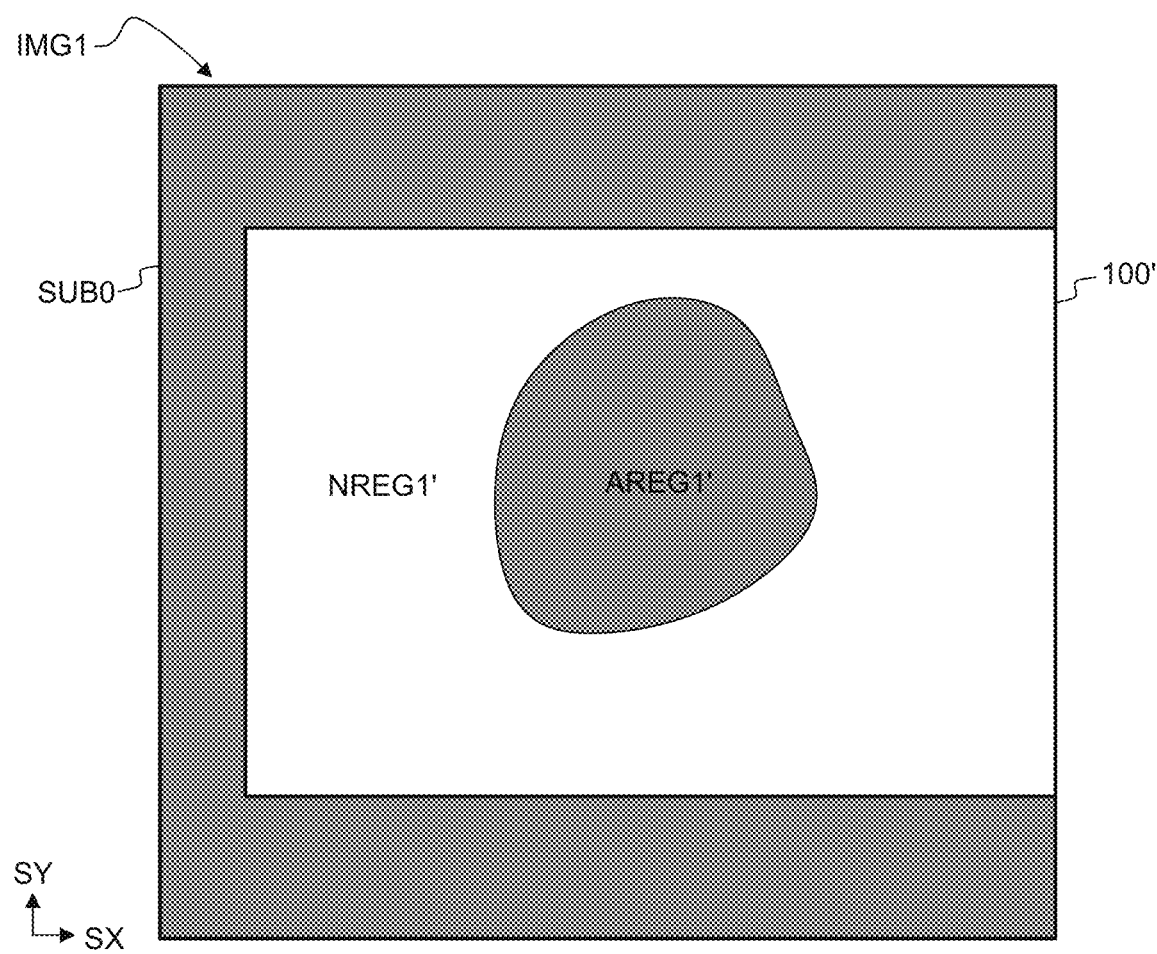
FIG. 16f shows, by way of example, an image of the label of FIG. 16e in a situation where the label is illuminated with excitation light.

Referring to FIG. 16f, the abnormal region may be detected e.g. as a darker spot AREG1' in a captured image IMG1. The fluorescence light LUM1 leaking at the normal region NREG1 may provide a brighter region in the image IMG1. The image AREG1' of the abnormal region AREG1 may be e.g. darker than the image NREG1' of the normal region NREG1.

The captured image (IMG1) may be compared with reference data (REFDATA1) e.g. in order to detect whether the adhesive layer of the label is properly in contact with the package.

Figure 17A:
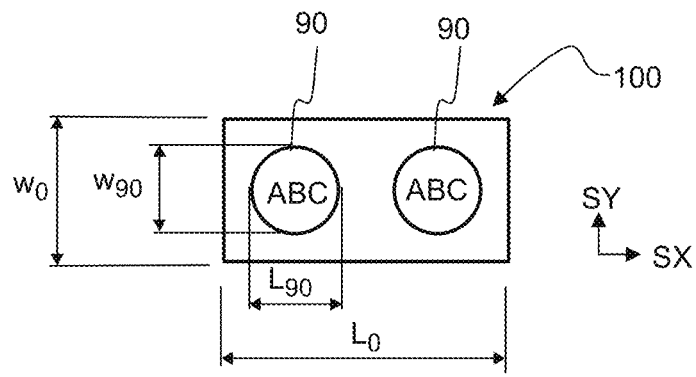
FIG. 17a shows, by way of example, in a top view, a label, which has a visually detectable indicator marking.
Figure 17B:
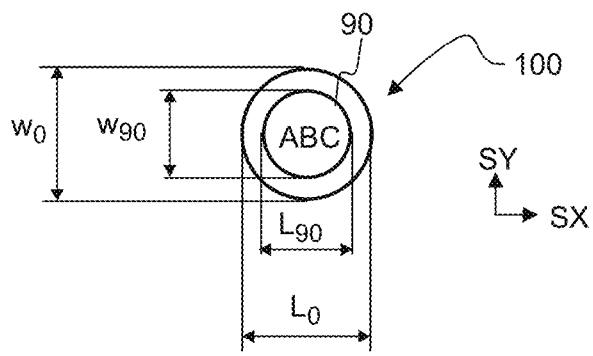
FIG. 17b shows, by way of example, in a top view, a label, which has a visually detectable indicator marking.

Referring to FIGS. 17a and 17b, the perimeter of the sealing label 100 may be e.g. rectangular or circular. In case of a rectangular label 100, the length of the label may be e.g. greater than or equal to 30 mm, and the width of the label may be e.g. greater than or equal to 15 mm. In case of a circular label, the diameter of the label may be e.g. greater than or equal to 25 mm.

The label 100 may have an initial length $L_0$ and an initial width $w_0$. In an embodiment, the perimeter of the label 100 may be used as a visual stretching indicator. A marking 90 of the label 100 may have an initial length $L_{90}$ and an initial width $w_{90}$. In an embodiment, the marking 90 may be used as a visual stretching indicator.

Figure 17C:
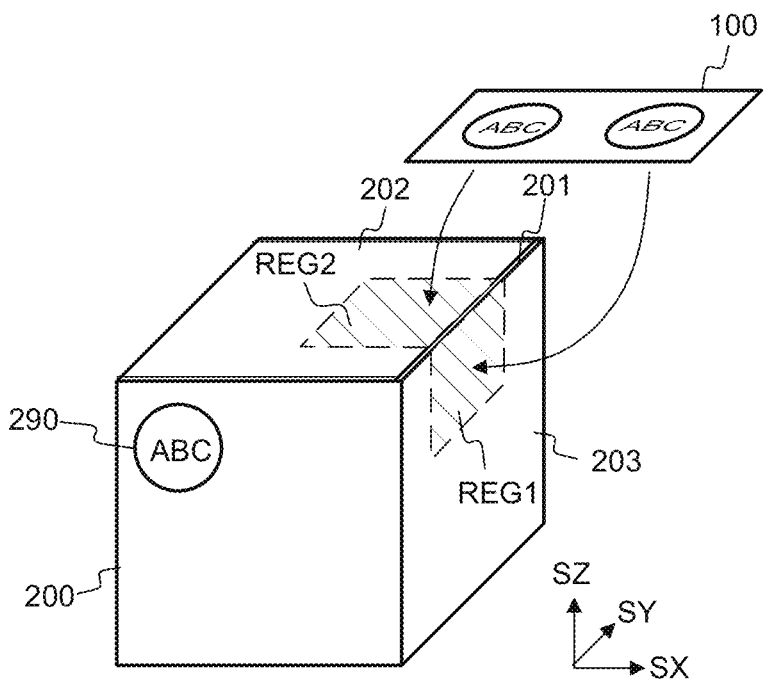
FIG. 17c shows, by way of example, attaching a label to a package.
Figure 17D:
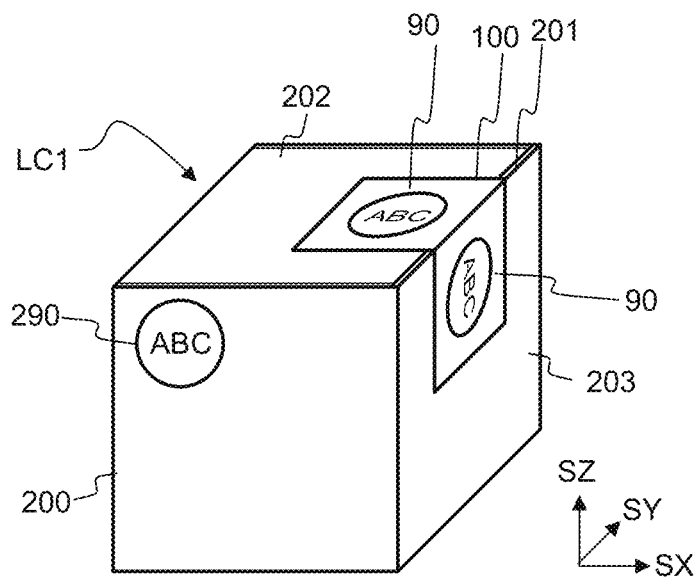
FIG. 17d shows, by way of example, in a three-dimensional view, a sealed package.

Referring to FIGS. 17c and 17d, the label 100 may be attached to a package 200 to form a combination LC1. The combination LC1 may be called e.g. as a sealed package. The package may be e.g. a cardboard box. The package may comprise one or more walls 203. The package may comprise one or more covers 202. The package may comprise a lid 202, which may be joined to a side of the package by a flexible hinge. The package 200 may comprise an opening joint 201. When the joint 201 is not sealed with the label, the joint 201 may be opened and closed several times without causing visual damage to the package. The label 100 may be attached to the package 200 such that the opening joint 201 is located between two attachment regions REG1, REG2.

The package 200 may comprise one or more markings MRK1, MRK2, MRK3, 290, which have been produced e.g. by printing or embossing. A surface of the varnished cardboard may comprise one or more holograms.

Figure 17E:
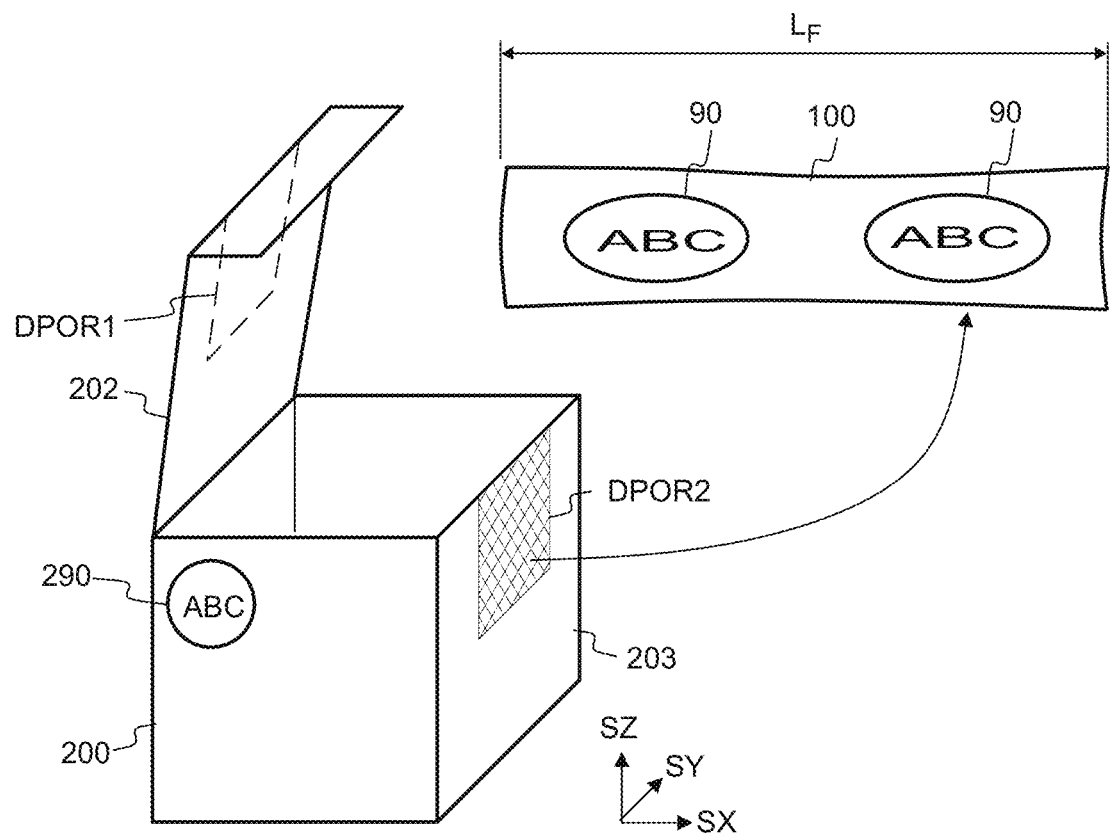
FIG. 17e shows, by way of example, a damaged label and a damaged package, after the label has been pulled with a pulling force.

Referring to FIG. 17e, the sealed package 300 may be opened e.g. by tearing the label 100 away from the package 200. The properties of the label 100 may be optionally selected such that the pulling the label 100 away from the package 200 causes permanent stretching of the label 100 and also visually alters the package 200. The attachment regions REG1, REG2 of the package may be converted into damaged portions DPOR1, DPOR2. The label 100 may have a final length $L_F$ after it has been separated from the package 200. The final length $L_F$ of the label 100 may be substantially greater than the initial length $L_0$ of said label 100. The stretching of the label 100 may be easily detected by comparing one or more dimensions of the label with a reference dimension. In an embodiment, one of the markings 290 of the package may define said reference dimension. A method of checking the authenticity of the sealed package 300 may comprise comparing a dimension of the label 100 with a reference dimension of a reference marking 290. In an embodiment, possible stretching of the label 100 may be detected by comparing a marking 90 of the label 100 with a marking 290 of the package.

In an embodiment, the label 100 may also be arranged to close an aperture (i.e. opening) of the package such that the aperture cannot be opened without causing permanent damage to the label 100 and to the package.

Figure 18A:
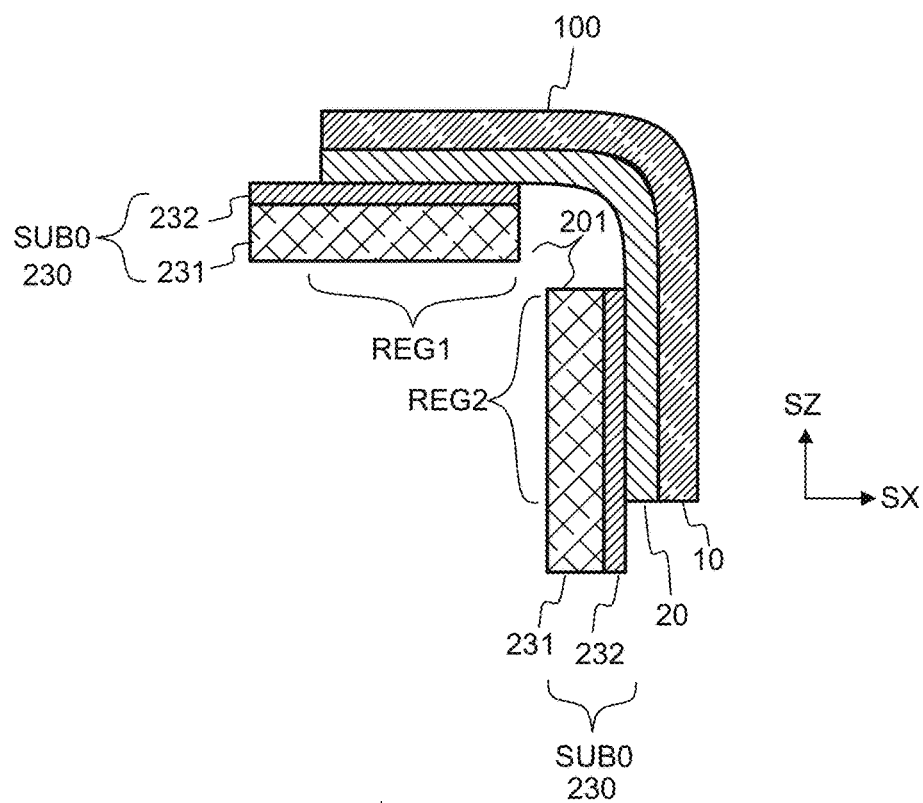
FIG. 18a shows, by way of example, in a cross-sectional view, a joint sealed by attaching a label to a substrate.

FIG. 18a shows a sealing label 100, which has been attached to a package 200, which comprises varnished cardboard 230. The varnished cardboard 230 may comprise cardboard material 231 covered with varnish 232. The varnished cardboard 230 may comprise a varnish layer 232 and cardboard material 231. The adhesive layer 20 of the label 100 may be in contact with the varnish 232.

The package 200 may comprise varnished cardboard 230, SUB0. The outermost surface of the varnished cardboard 230 may consist essentially of the water-based acrylate varnish. The varnished cardboard 230 may be e.g. fully coated folding boxboard approved for containing a medicament, wherein the varnish of the varnished layer 232 may be e.g. water-based acrylate varnish The label 100 may be attached to a first attachment region REG1 and to a second attachment region REG2 of the package 200. The label 100 may be attached to the package such that an opening joint 201 of the package is located between the first attachment region REG1 and the second attachment region REG2. For example, the first attachment region REG1 may be located on a side 203 of the package, and the second attachment region REG2 may be located on a lid or cover 202 of the package 200. The label 100 may be attached to the package such that the label 100 cannot be separated from the package without separating the label 100 from the first attachment region REG1 and from the second attachment region REG2. The label 100 may be attached to the package such that the opening joint 201 cannot be opened without breaking the label 100, without damaging the package, and/or without separating the label 100 from at least one of the first attachment region REG1 and the second attachment region REG2.

The varnished cardboard 230 may comprise a first layer 231 and a second layer 232. The first 231 layer may comprise cardboard material. The first 231 layer of the varnished cardboard 230 may comprise cellulose fibers. The second layer 232 may consist essentially of varnish, or the second layer 232 may comprise cellulose fibers impregnated with the varnish. The second layer 232 may be the outermost layer of the varnished cardboard 230. The varnish may be e.g. water-based acrylate varnish or UV-curable varnish. An UV-curable varnish may be applied to the cardboard material and cured by using ultraviolet light. The varnish may be approved for use in pharmaceutical packages. The varnished cardboard 230 may be e.g. fully coated folding boxboard.

Figure 18B:
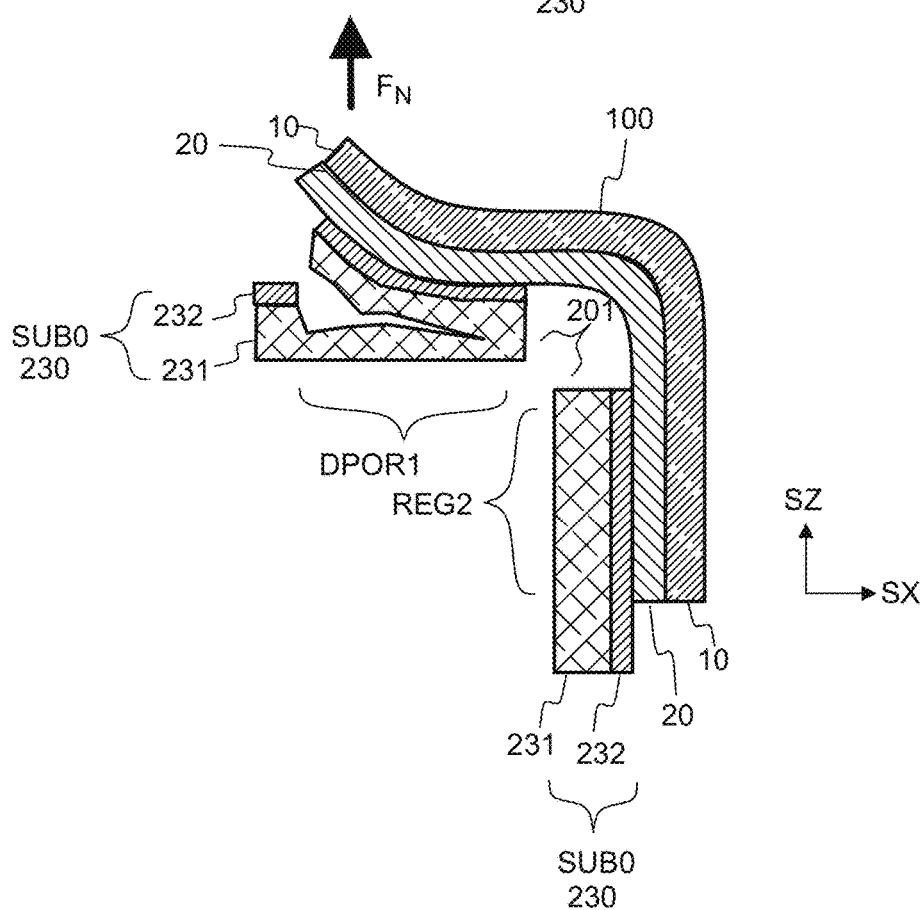
FIG. 18b shows, by way of example, in a cross-sectional view, a damaged label and a damaged substrate, after the label has been pulled with a pulling force.

Referring to FIG. 18b, the properties of the label 100 may be selected such that an attempt to separate the label 100 from the attachment region REG1 also causes visually detectable irreversible damage to the cardboard material 230. The label 100 may be pulled away from the attachment region REG1 by a pulling force $F_N$. Pulling the label 100 away from the first attachment region REG1 may convert the first attachment region REG1 into a first damaged region DPOR1. Pulling the label 100 away from the second attachment region REG2 may convert the second attachment region REG2 into a second damaged region DPOR2 (FIG. 17e).

The pulling force $F_N$ may be substantially perpendicular to the attachment region REG1. The pulling force may have a component $F_N$, which is perpendicular to the attachment region REG1. The tensile stress caused by the pulling force $F_N$ in the cardboard material 231 may exceed the breaking strength $\sigma_{TS}$ of the cardboard material 231.

The damaged portion DPOR1 may be a pit (i.e. a crater). The cardboard material 231 may be torn apart when the label 100 is pulled such that a piece of cardboard is separated from the package 200 and such that a pit DPOR1 is formed on the package 200.

Figure 19A:
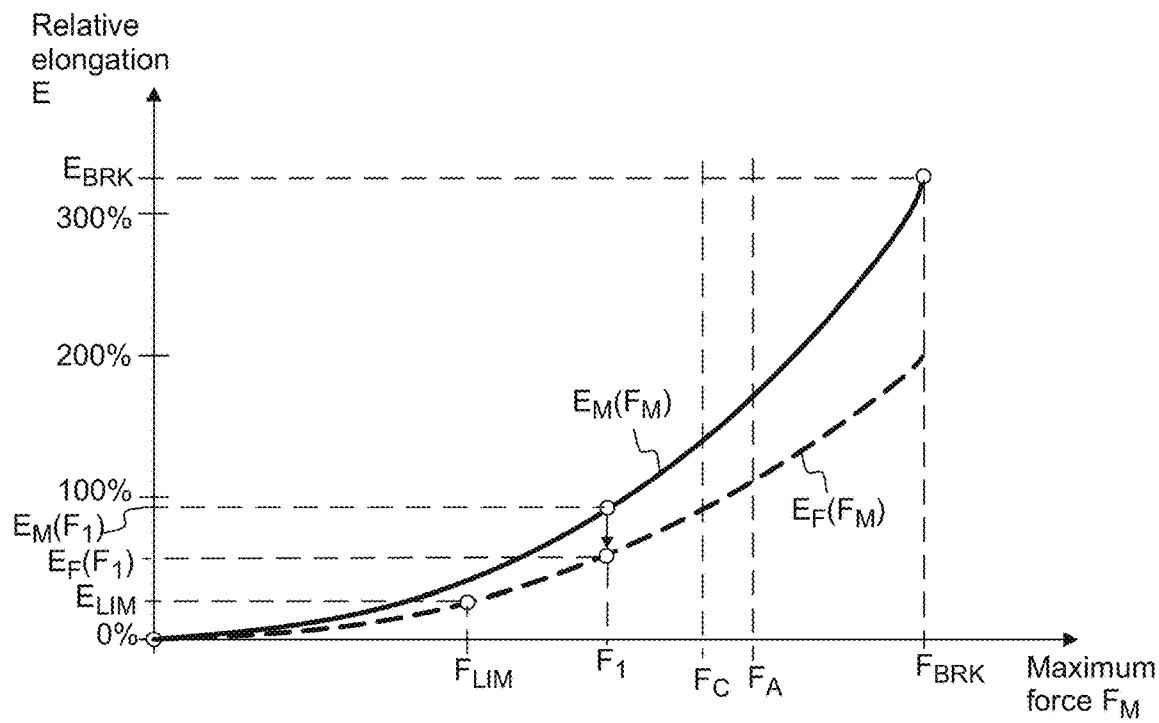
FIG. 19a shows, by way of example, elongation of a label as a function of pulling stress.

FIG. 19a shows, by way of example, maximum elongation $E_M(F_M)$ of the label 100 as the function of the maximum force $F_M$, and final elongation $E_F(F_M)$ of the label (100) as the function of the maximum force $F_M$.

The irreversible deformation of the label 100 may be easily visually detectable after the maximum pulling force $F_M$ has been greater than a limit value $F_{LIM}$. The elongation $E_F(F_{LIM})$ at the limit value $F_{LIM}$ may be e.g. equal to 30%. The limit value $F_{LIM}$ may be defined to be e.g. the value of the pulling force $F_M$, which causes an elongation $E_F$, which is equal to 30%.

$F_C$ may denote the breaking force $F_C$ of the cardboard material 231. The breaking force $F_C$ may mean the minimum value of the pulling force $F_M$, which causes visually detectable permanent damage to the cardboard material 231 when the label 100 is pulled away from the attachment region POR1 of the varnished cardboard. The breaking force $F_C$ may mean the minimum value of the pulling force $F_M$, which tears a piece away from the cardboard material 231. Pulling the label 100 away from the attachment region POR1 of the varnished cardboard with the breaking force $F_C$ may break the cardboard material 231.

$F_A$ may denote the detaching force of the adhesive of the adhesive layer 20. The detaching force $F_A$ may mean the minimum value of the pulling force $F_M$, which is sufficient to separate the label 100 from the varnished surface of the attachment region POR1. The detaching force $F_A$ may also be called e.g. as the de-bonding force.

The properties of the label 100 may be selected such that an attempt to separate the label 100 from the varnished cardboard causes irreversible damage both to the label 100 and to the varnished cardboard. The properties of the label 100 may be selected such that the label cannot be separated from the varnished cardboard without irreversibly visually detectable stretching the label, and the label cannot be separated from the varnished cardboard without causing irreversible visually detectable tearing of the cardboard material.

The label 100 may have a high breaking strength in order to ensure that the cardboard is permanently damaged before the label is broken into pieces.

In case of a perforated label 100, the label 100 may have a high breaking strength in order to ensure that the cardboard is permanently damaged before a non-perforated continuous portion of the label is broken into pieces.

The label may be arranged to tear the cardboard material apart at the lower force than what is required to break the label.

The adhesive layer 20 may be firmly adhered both to the carrier layer 10 and to the varnish 232 in order to ensure that the cardboard is permanently damaged before the adhesive layer 20 is detached.

The label (100) may be suitable for use on a varnished cardboard (230, SUB0), the label (100) may comprise:
a carrier layer (10),
an adhesive layer (20), and
a wavelength conversion layer (WG1,CL1),
wherein the thickness ($d_{10}$) of the carrier layer (10), the material of the carrier layer (10), and the composition of the adhesive layer (20) h selected such that:
a minimum deformation force ($F_{LIM}$) of the label is smaller than a first breaking force ($F_C$) needed to break the cardboard material (231) of the varnished cardboard (230),
a minimum detaching force ($F_A$) of the label (100) is greater than the first breaking force ($F_C$), and
a second breaking force ($F_{BRK}$) needed to break the label (100) is greater than the first breaking force ($F_C$),
wherein the first breaking force ($F_C$) is a first pulling force which causes breaking of the cardboard material (231) in a situation where the label (100) is separated from the varnished cardboard (230) by pulling the label (100) with said first pulling force, and the minimum detaching force ($F_A$) is a second pulling force which is needed to separate the adhesive layer (20) of the label (100) from the surface (SRF4) of the varnished cardboard (230) in a situation where the label (100) is pulled with said second pulling force.

The elongation ($E_{BRK}$) at break of the carrier layer (10) may be e.g. higher than or equal to 300%, advantageously higher than or equal to 450%, and preferably higher than or equal to 500%. The carrier layer (10) may comprise e.g. polypropylene.

Figure 19B:
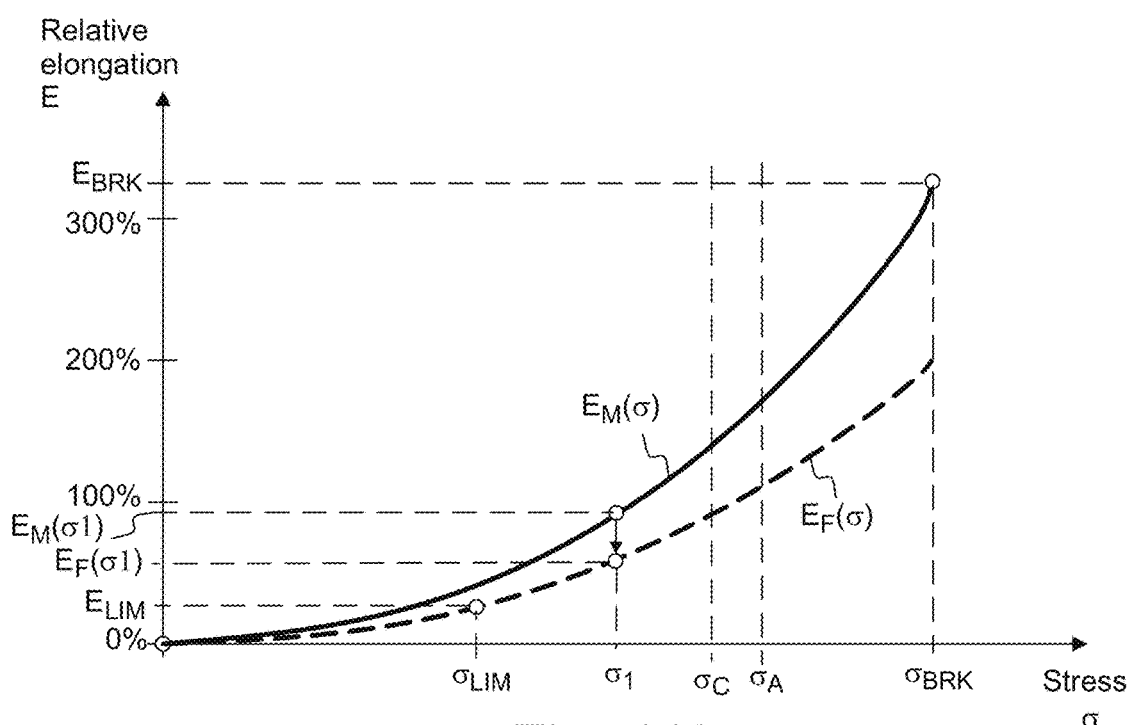
FIG. 19b shows, by way of example, elongation of adhesive laminate web as a function of pulling force.

FIG. 19b shows, by way of example, maximum elongation $E_M(\sigma)$ and final elongation $E_F(\sigma)$ of a label 100 as the function of stress σ of the carrier layer 10 of the label 100 of FIG. 19a.

$\sigma_{LIM}$ may denote a stress which causes 30% final elongation. $\sigma_C$ may denote a stress which causes breaking of cardboard of a package. $\sigma_A$ may denote a stress which is sufficient to detach the adhesive of the label from varnished cardboard. $\sigma_{BRK}$ may denote a stress, which breaks the carrier layer into two or more pieces. The materials and/or the thickness of the material layers of the label 100 may be selected e.g. such that $\sigma_A > \sigma_{LIM}$, such that $\sigma_C > \sigma_{LIM}$, such that $\sigma_A > \sigma_C$, and such that $\sigma_{BRK} > \sigma_C$, so as ensure the label and the package exhibit visually detectable deformation.

Figure 20A:
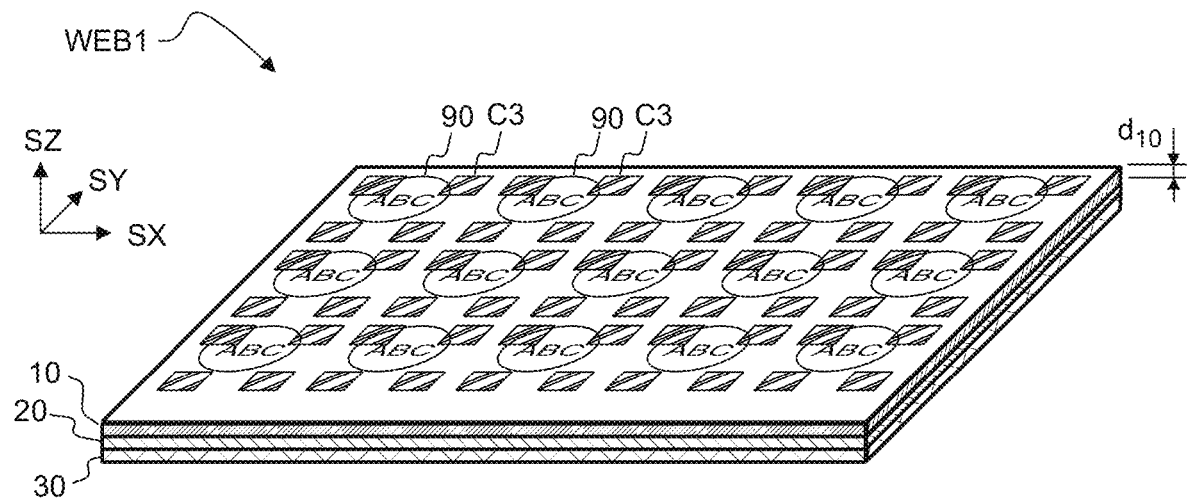
FIG. 20a shows, by way of example, in a three-dimensional view, an adhesive laminate web.

Referring to FIG. 20a, a label web WEB1 may be produced. The web WEB1 may be produced and/or transported e.g. as a sheet or as a roll. A plurality of the labels 100 may be subsequently cut and/or separated from the web WEB1. The materials of the layers 10, 20, and the thickness of the layers 10, 20 may be selected such that the labels 100 may be formed by cutting from the web WEB1. The web WEB1 may comprise a release liner 30 to protect the adhesive layer 20, and/or to facilitate handling of the web. The release liner 30 may have e.g. an anti-adhesion coating to facilitate removal from the adhesive layer 20. The anti-adhesion coating may be e.g. a silicone coating.

Producing a plurality of labels 100 may comprise:
producing a web WEB1, which comprises a carrier layer 10, an adhesive layer 20, and modulating structures (STR1), and
separating one or more labels 100 from the web WEB1.

Figure 20B:
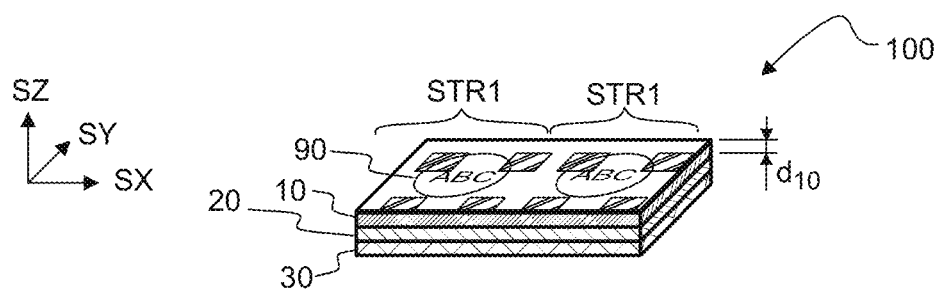
FIG. 20b shows, by way of example, in a three-dimensional view, a label obtained by cutting from the adhesive laminate.

Referring to FIG. 20b, labels 100 cut from the web WEB1 may comprise the carrier layer 10, the adhesive layer, 20, a modulating structure STR1 and a release liner 30. The release liner 30 may be removed before the adhesive layer 20 is brought into contact with the package 200.

In an embodiment, the carrier layer 10 of the label 100 may be pharmaceutical grade polypropylene film, the thickness $d_{10}$ of the film may be e.g. substantially equal to 65 μm, the elongation $E_{BRK}$ of the film 10 at break may be e.g. substantially equal to 600%, and the tensile strength $\sigma_{BRK}$ may be e.g. substantially equal to 36 N/mm² in the machine direction (MD). The adhesive layer 20 may comprise e.g. a water-based polymer composition. The adhesive may be selected such that the adhesive is approved for use in pharmaceutical applications.

Figure 21:
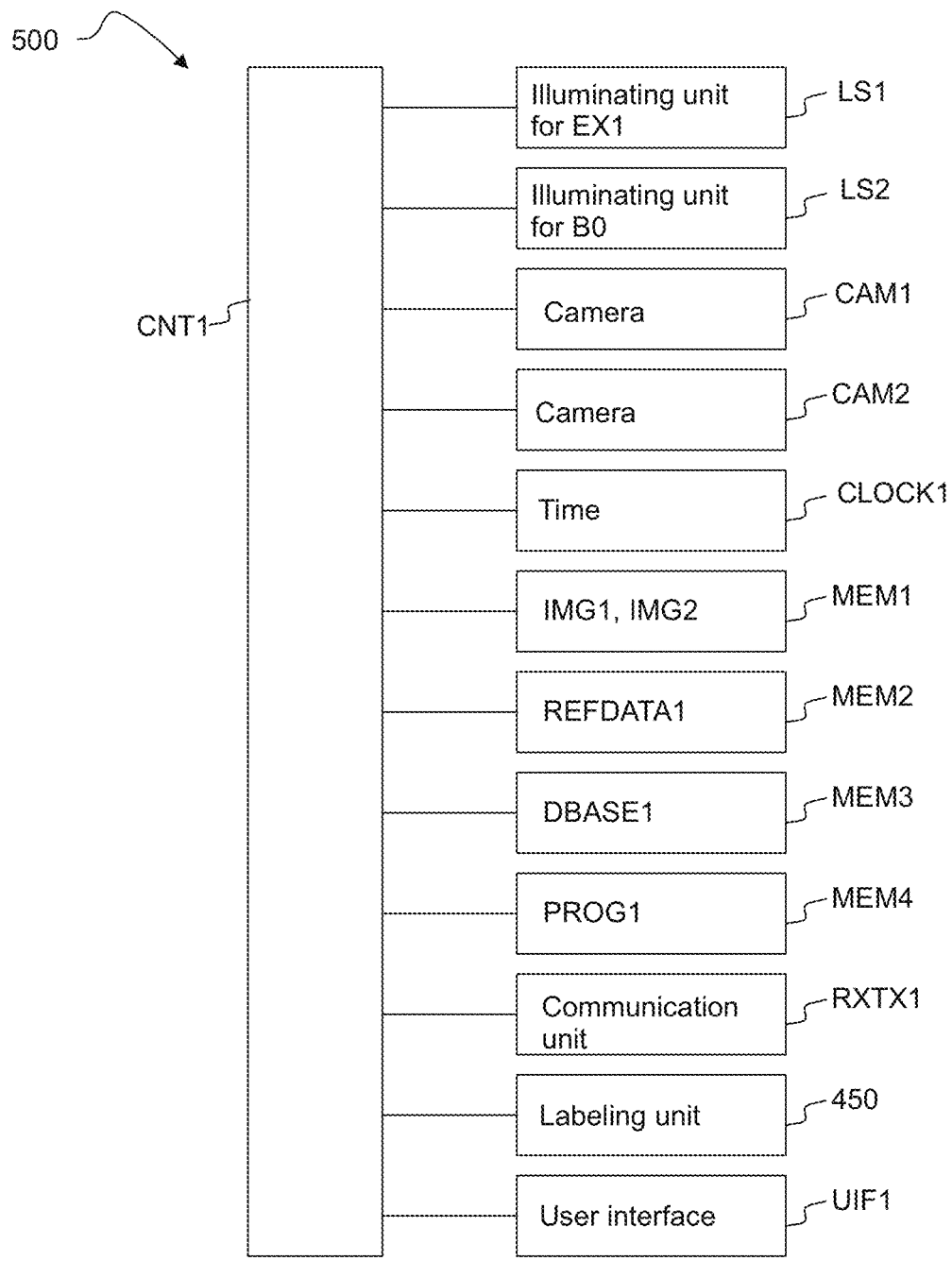
FIG. 21 shows, by way of example, units of a monitoring apparatus.

FIG. 21 shows, by way of example, units of a monitoring apparatus 500. The apparatus 500 may comprise one or more illuminating units LS1 to provide excitation light EX1. The apparatus 500 may comprise one or more illuminating units LS2 to provide auxiliary illuminating light B0. The apparatus 500 may comprise one or more cameras CAM1, CAM2 to capture images IMG1, IMG2. The apparatus 500 may comprise a clock to provide time information. The time information may be used e.g. for time-stamping verification data, which may be stored e.g. in the memory MEM3 and/or in a database. The apparatus 500 may comprise a memory MEM1 for storing captured images IMG1, IMG2. The apparatus 500 may comprise a memory MEM2 for storing reference data REFDATA1. The apparatus 500 may comprise a memory MEM3 for storing information, which indicates whether the label is at a correct position or not. This information may be stored in a database DBASE. The apparatus 500 may comprise a memory MEM4 for computer program PROG1. The apparatus 500 may comprise a control unit CNT1. The control unit CNT1 may comprise one or more data processors. The computer program PROG1 may be configured to cause performing one or more steps of the present method, when executed by the one or more data processors. The apparatus 500 may comprise a communication unit RXTX1 for communicating data. The communication unit RXTX1 may be arranged to communicate e.g. with the Internet and/or with an process control system. The apparatus 500 may comprise a user interface for providing information to a user and/or for receiving comments from the user.

The reference data REFDATA1 may e.g. specify an acceptable range for the position of a label 100. The captured image IMG1 may be compared with the reference data REFDATA1 e.g. in order to determine whether the label is at a correct position and/or whether the label is properly attached to the package. The reference data REFDATA1 may e.g. specify an acceptable range for the brightness at one or more locations of a captured image. The reference data REFDATA 1 may specify e.g. an acceptable range of brightness values for an edge, which appears in a captured image of a label.

The reference data REFDATA1 may comprise e.g. one or more images of a label which is properly attached to a package. The reference data REFDATA 1 may comprise e.g. one or more reference images. A reference image may comprise e.g. an image of a label which is properly attached to a package.

Figure 22A:
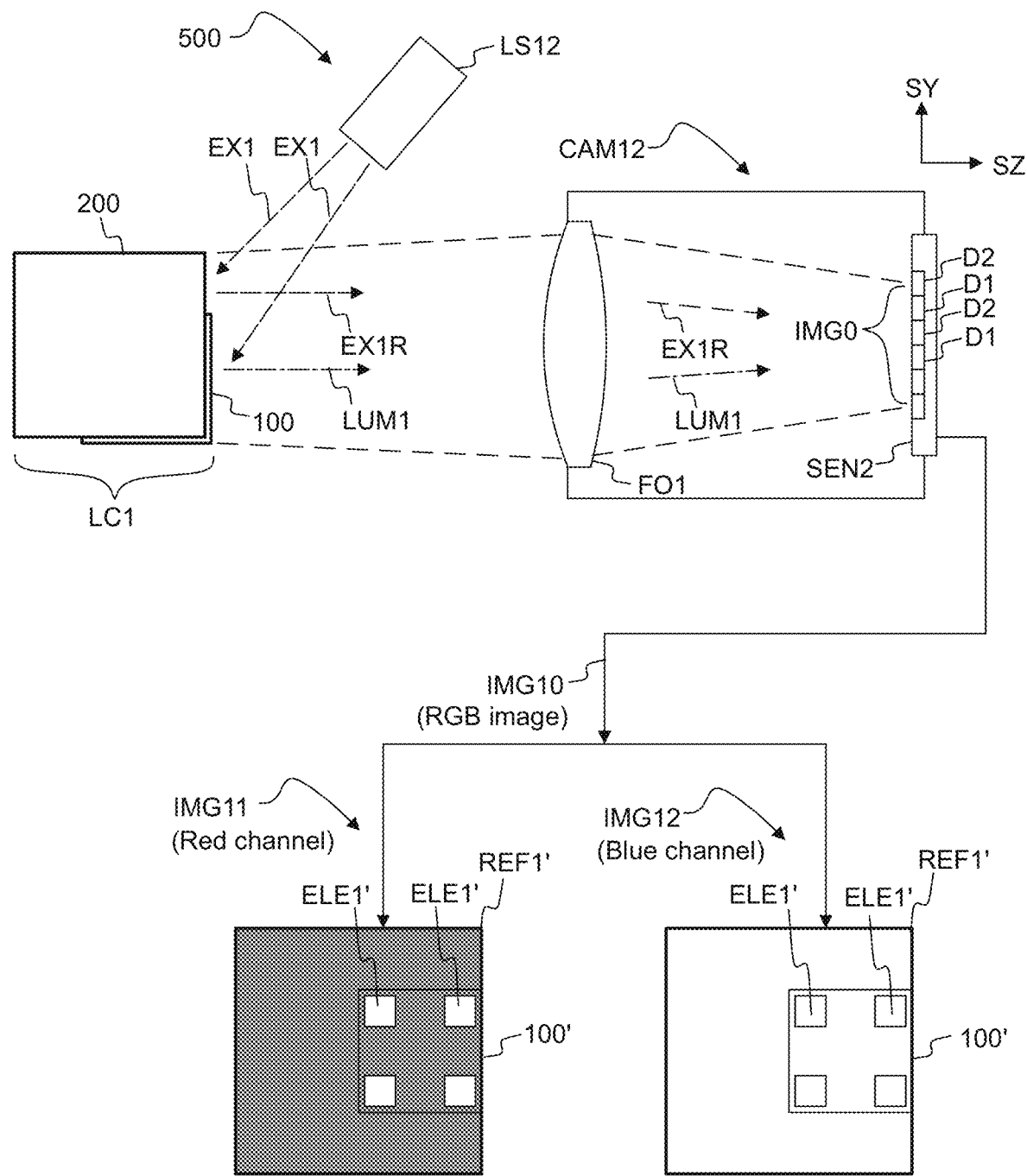
FIG. 22a shows, by way of example, monitoring the position of the label by using a monitoring apparatus.

Referring to FIG. 22a, the monitoring apparatus 500 may comprise a light source LS12 to provide excitation light EX1, and the apparatus 500 may comprise an imaging unit CAM12 to capture an image IMG10 of the label 100, when the label 100 is illuminated with the excitation light EX1.

The imaging unit CAM12 may comprise an array of first detector pixels D1 which have a first spectral response, and an array of second detector pixels D2 which have a second different spectral response. The imaging unit CAM12 may comprise an image sensor SEN2. The image sensor SEN2 may comprise an array of first detector pixels D1 and an array of second detector pixels D2. The imaging unit CAM12 may comprise focusing optics F01 to form an optical image IMG0 of the label 100 on the image sensor SEN12 by focusing light. The image sensor SEN12 may convert the optical image IMG0 into a captured digital image IMG10. The captured image IMG10 may comprise a first component image IMG11 and a second component image IMG12. The first component image IMG11 and the second component image IMG12 may be digital images.

The focusing optics FO1 may be arranged to focus reflected excitation light EX1R and fluorescence light LUM1 to the image sensor SEN2. The spectral response of the first detector pixels may be selected such that the first detector pixels may spectrally selectively detect fluorescence light LUM1 and such that the first detector pixels may be substantially insensitive to the reflected excitation light EX1R. The imaging unit CAM12 may be implemented also without using a common spectral filter for the detector pixels D1, D2 of the imaging unit CAM12.

Figure 22B:
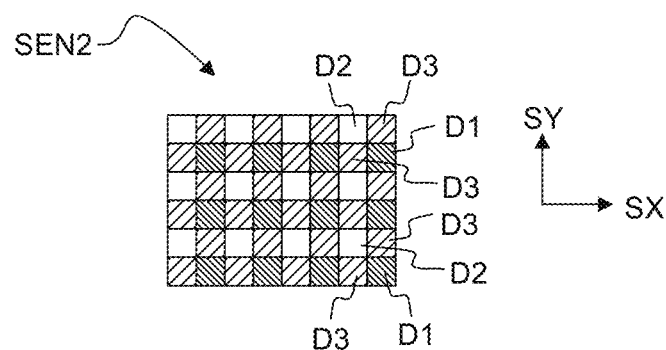
FIG. 22b shows, by way of example, first detector pixels and second detector pixels of the monitoring apparatus of FIG. 22a, FIG. 22c shows, by way of example, spectral response of the first detector pixels and spectral response of the second detector pixels.

The captured digital image IMG10 may be e.g. a multi-color image, which comprises a first component image of a first color, and a second component image of a second color. The captured digital image IMG10 may be e.g. an RGB image formed of a first component image representing the red color (R), a second component image representing blue color (B), and a third component image representing green color (G). The first component image IMG11 may be formed of detector signals provided by the first detector pixels D1. The second component image IMG12 may be formed of detector signals provided by the second detector pixels D2. A third component image may be formed of detector signals provided by third detector pixels D3 (FIG. 22b).

The imaging unit CAM12 may comprise a focusing unit FO1 and one or more image sensors SEN2. The label 100 and the package 200 may reflect and/or scatter a part of the excitation light EX1 to the imaging unit CAM12. The focusing unit FO1 may focus gathered light to the image sensor SEN2. The focusing unit FO1 may focus reflected light, scattered light, and/or fluorescence light to the image sensor SEN2.

The first detector pixels D1 may provide the first component image IMG11 by detecting fluorescence light LUM1 emitted from the label 100 and/or from the substrate of the package 200. The first detector pixels D1 may in a spectrally selective manner detect light LUM1 formed by the wavelength conversion.

The second detector pixels D2 may provide the second component image IMG12 by detecting light (EX1, B0), which is reflected and/or scattered from the label 100, and by detecting light (EX1, B0) reflected and/or scattered from the package 200. The second detector pixels D2 may detect reflected and/or scattered excitation light EX1. The second detector pixels D2 may detect reflected and/or scattered auxiliary light B0. The second component image IMG12 may represent a grayscale image of the combination of the label and the package, wherein the contribution of fluorescence light LUM1 to the second component image IMG12 may be suppressed.

The first component image IMG11 may be used together with the second component image IMG12, e.g. in order to reliably detect the relative position of the label 100 with respect to the package 200. For example a position of the label may be determined from the first component image IMG11, a position of the package may be determined from the second component image IMG12, wherein the position of the label may be compared with the position of the package in order to determine whether the label is at a correct relative position or not.

The second component image IMG12 may be analyzed by using an image analysis algorithm e.g. in order to detect whether the shape of the package 200 matches with a predetermined shape or not. The second component image IMG12 may be analyzed e.g. in order to detect whether the dimensions of the package 200 match with predetermined dimensions or not.

The package 200 may comprise a detectable pattern. The pattern may be formed e.g. by printing on the surface of the package. The pattern may be e.g. an alphanumerical code. The pattern may be e.g. a one-dimensional barcode or a two-dimensional barcode. The pattern may be machine-readable. The pattern may also be visually detectable. The pattern of the package 200 may be detected and/or read from the second component image IMG12. The pattern of the package 200 may be detected and/or read by image analysis of the second component image IMG12.

When using the first detector pixels and the second detector pixels, the position of the label and the shape of the package may be determined from the digital image IMG10 captured by the imaging unit CAM12. When using the first detector pixels and the second detector pixels, the position of the label and the shape of the package may be determined even from a single digital image IMG10 captured when illuminating the combination LC1 with one illuminating light pulse (e.g. a single flash of light EX1).

The apparatus 500 may comprise a control unit CNT1. The control unit CNT1 may comprise one or more data processors. The computer program PROG1 may be configured to cause performing one or more steps of the present method, when executed by the one or more data processors of the control unit CNT1.

Referring to FIG. 22b, the imaging unit CAM12 may comprise one or more image sensors SEN2. The image sensor SEN2 may comprise an array of first detector pixels D1, an array of second detector pixels D2, and an array of third detector pixels D3. The first detector pixels D1 may be arranged to spectrally selectively detect light which has a first color (e.g. red). The second detector pixels D2 may be arranged to spectrally selectively detect light which has a second color (e.g. blue). The third detector pixels D3 may be arranged to spectrally selectively detect light which has a third color (e.g. green). The image sensor SEN12 may be e.g. an RGB image sensor.

The image sensor SEN12 may comprise a first array of first detector pixels D1, and a second array of second detector pixels D2, wherein the first detector pixels D1 may be interlaced with the second detector pixels D2. The first array of detector pixels D1 may be interlaced with the second array of detector pixels.

The image sensor SEN12 may comprise a first array of first detector pixels D1, a second array of second detector pixels D2, and a third array of third detector pixels D3, wherein the first detector pixels D1 may be interlaced with the second detector pixels D2 and with the third detector pixels D3.

The imaging unit CAM12 may comprise a plurality of first detector pixels D1 to provide a first component image IMG11 by detecting fluorescence light LUM1, wherein the imaging unit CAM12 may further comprises a plurality of second detector pixels D2 to provide a second component image IMG12 by detecting light EX1R reflected and/or scattered from the package 200, wherein the first detector pixels D1 have a first spectral response $S_{D1}(\lambda)$, and the second detector pixels D2 have a second different spectral response $S_{D2}(\lambda)$.

The imaging unit CAM12 may further comprise a plurality of third detector pixels D3, wherein the spectral response $SD3(\lambda)$ may be different from the spectral response $S_{D1}(\lambda)$ of the first detector pixels D1 and different from the spectral response $S_{D2}(\lambda)$ of the first detector pixels D2.

The image sensor SEN12 may comprise e.g. a Bayer color filter array to provide first spectral response $S_{D1}(\lambda)$ for the first detector pixels D1, to provide second spectral response $S_{D2}(\lambda)$ for the second detector pixels D2, and to provide third spectral response $S_{D3}(\lambda)$ for the second detector pixels D3.

The image sensor SEN12 may be e.g. a CMOS sensor or an CCD sensor. CMOS means complementary metal oxide semiconductor. CCD means charge coupled device.

Figure 22C:
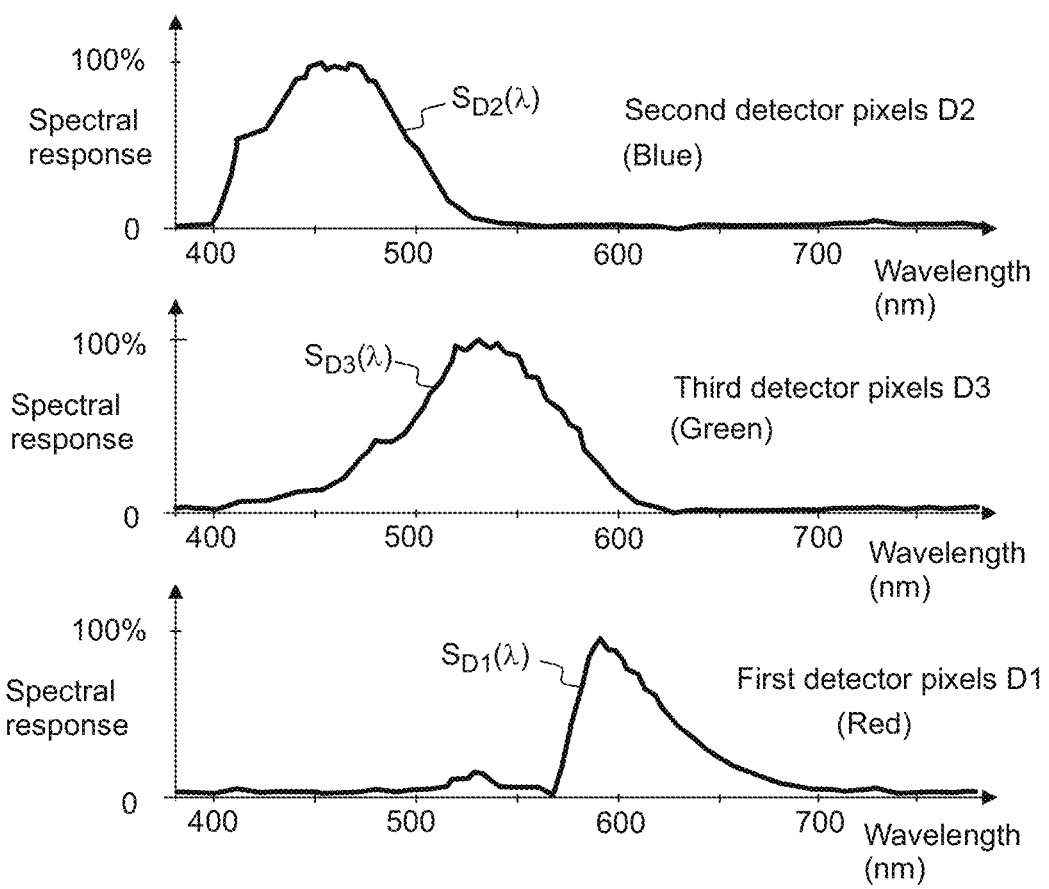

Referring to FIG. 22c, the spectral response of the second detector pixels D2 may be different from the response of the first detector pixels D1. The spectral response of the third detector pixels D3 may be different from the spectral response of the first detector pixels D1 and different from the spectral response of the second detector pixels D2.

In an embodiment, the imaging unit CAM12 may comprise a first image sensor and a second image sensor. The first image sensor may comprise first detector pixels D1 which have a first spectral response $S_{D1}(\lambda)$, and the second image sensor may comprise second detector pixels D2 which have a second spectral response $S_{D2}(\lambda)$. Gathered light may be coupled from the focusing optics FO1 to the first image sensor and to the second image sensor e.g. via one or more beam splitters. Gathered light may be coupled from the focusing optics to the first image sensor and to the second image sensor e.g. via one or more spectrally selective beam splitters.

Figure 23A:
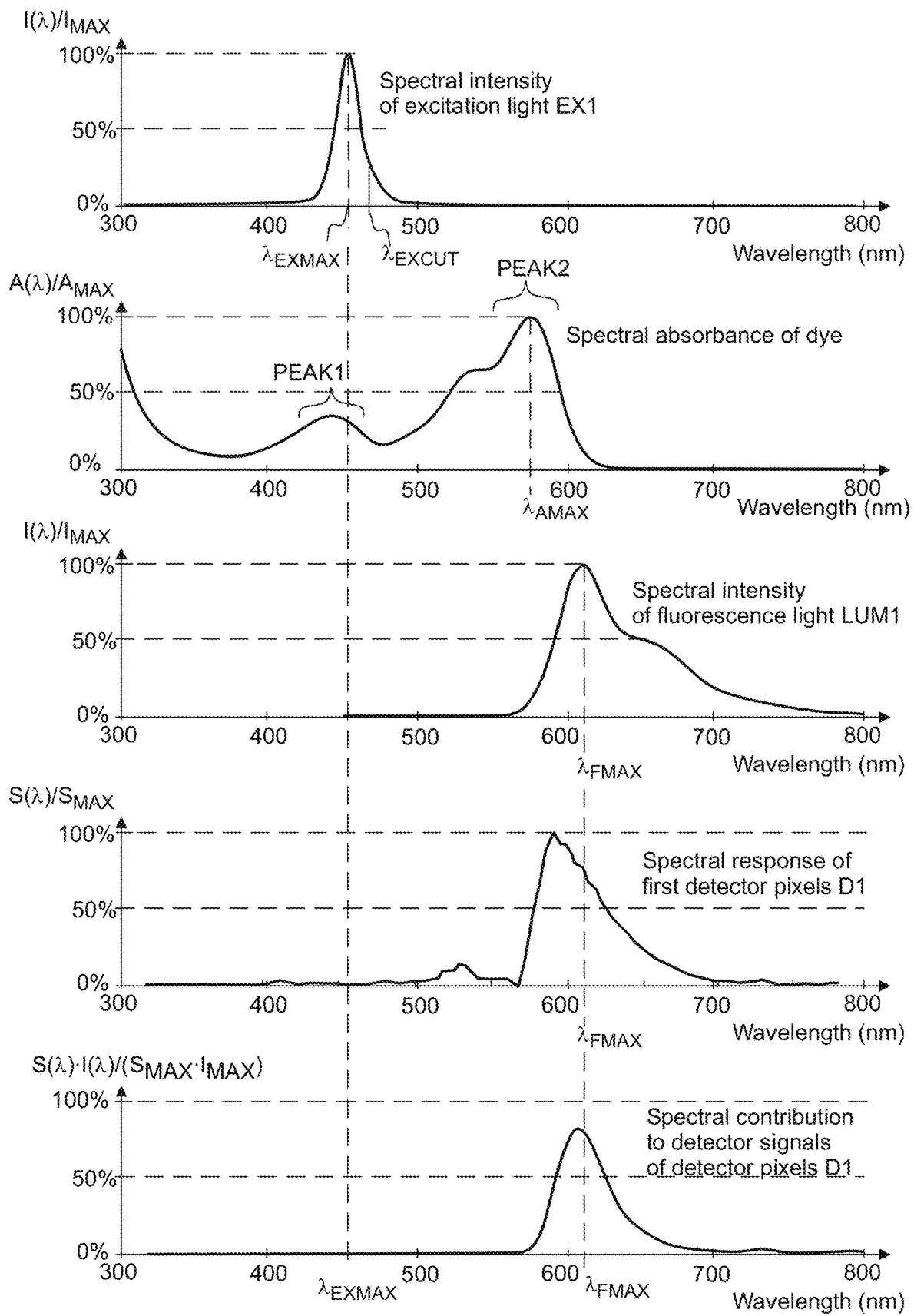
FIG. 23a shows, by way of example, formation of detector signals of the first detector pixels.

Referring to FIG. 23a, the spectral response $S_{D1}(\lambda)$ of the first detector pixels D1 may be selected such that the first detector pixels D1 are insensitive to one or more spectral components of the excitation light EX1. The first detector pixels D1 may have low response to the excitation light EX1.

A signal provided by a single detector pixel D1 may be proportional to an integral of a function $I(\lambda)S_{D1}(\lambda)$. The symbol $I(\lambda)$ may denote spectral intensity of light impinging on the detector pixel D1, and the symbol $S_{D1}(\lambda)$ may denote the spectral response of the detector pixel D1. The integral may be calculated e.g. over a spectral range which includes spectral components of the light impinging on the detector pixel D1.

The second curve from the bottom of FIG. 23a shows relative spectral response $S_{D1}(\lambda)$ of the first detector pixels D1. $S_{MAX}$ denotes maximum value of the spectral response.

The imaging unit may gather fluorescence light, reflected light and scattered light from the combination of the label and the package. The focusing optics may focus gathered light to the image sensor. Some spectral components of the gathered light may contribute to the signal provided by a detector pixel D1, and some spectral components of the gathered light do not contribute to the signal provided by the detector pixel D1. The lowermost curve of FIG. 23a shows relative spectral contribution $I(\lambda)S_{D1}(\lambda)$ of the gathered light to a detector signal of a first detector pixel D1. The lowermost curve of FIG. 23a may be obtained by multiplying the spectral intensity $I(\lambda)$ of the gathered light with the spectral response function $S(\lambda)$ of the first detector pixels D1.

The first detector pixels D1 may be arranged to form a first component image IMG11 by detecting the fluorescence light LUM1.

The first detector pixels D1 may be insensitive to one or more spectral components of the excitation light EX1. The first detector pixels D1 may have low response to the excitation light EX1.

Spectral components of the fluorescence light LUM1 may significantly contribute to the detector signal obtained from the first detector pixels D1.

The spectral response of the first detector pixels D1 may be selected such that spectral components of the excitation light EX1 do not significantly contribute to the detector signal obtained from the first detector pixels D1.

Figure 23B:
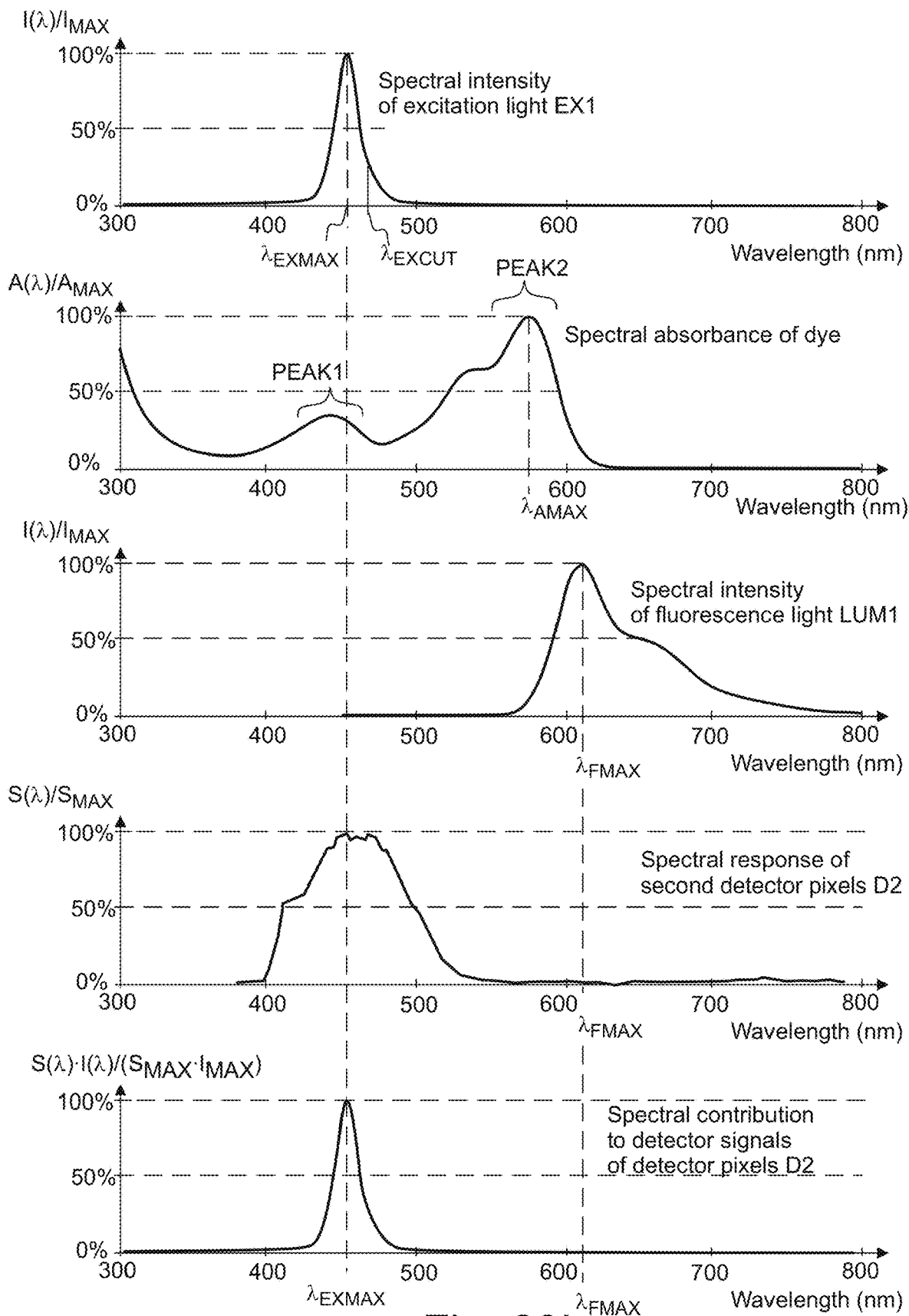
FIG. 23b shows, by way of example, formation of detector signals of the second detector pixels.

Referring to FIG. 23b, the spectral response $S_{D2}(\lambda)$ of the second detector pixels D2 may be selected such that the detector pixels D2 may detect at least a part of the light (EX1R) which is reflected and/or scattered from the combination LC1. The second detector pixels D2 may be arranged to form a second component image IMG12 by detecting light reflected and/or scattered from the combination LC1 of the label and the package.

The second detector pixels D2 may be insensitive to the fluorescence light LUM1. The second detector pixels D2 may have low response to fluorescence light LUM1.

In an embodiment, the light source LS12 may be arranged to provide additional illuminating light B0 together with excitation light EX1. The additional illuminating light B0 may be e.g. visible light. The light source LS12 may be arranged to provide an illuminating light pulse, which comprises excitation light EX1 and additional illuminating light B0. For example, the illuminating light pulse (EX1+B0) may simultaneously comprise ultraviolet excitation light (EX1) and visible auxiliary light (B0).

The focusing optics FO1 may receive fluorescence light LUM1, reflected auxiliary light B0 and/or scattered auxiliary light B0 from the combination of the label and the package. The focusing optics FO1 may focus fluorescence light LUM1, reflected auxiliary light B0 and/or scattered auxiliary light B0 to the image sensor SEN2. In particular, the focusing optics FO1 may focus fluorescence light together with the reflected and/or scattered auxiliary light B0 to the image sensor SEN2.

The imaging unit CAM12 may be arranged to capture an image IMG10 when the combination LC1 of the label 100 and the package 200 is illuminated with said light pulse. The captured digital image IMG10 may comprise a first component image IMG11 and a second component image IMG12. The first detector pixels D1 may provide the first component image IMG11 by detecting the fluorescence light LUM1. The second detector pixels D2 may provide the second component image IMG12 by detecting reflected and/or scattered auxiliary light B0. The first detector pixels D1 may have a higher response to the fluorescence light LUM1, and a lower response to the excitation light EX1. The second detector pixels D2 may have a higher response to reflected and/or scattered auxiliary light B0, and the second detector pixels D2 may have a lower response to the fluorescence light LUM1.

The first detector pixels D1 may spectrally selectively detect fluorescence light LUM1. The first detector pixels D1 may be insensitive to the reflected and/or scattered excitation light EX1. The second detector pixels D2 may spectrally selectively detect reflected and/or scattered auxiliary light B0. The first detector pixels D1 may be sensitive to the fluorescence light LUM1, wherein the second detector pixels D2 may be insensitive to the fluorescence light LUM1. The second detector pixels D2 may be sensitive to the reflected and/or scattered auxiliary light B0, wherein the first detector pixels D1 may be insensitive to the reflected and/or scattered auxiliary light B0.

Various aspects are illustrated by the following examples.

Example 1. A label (100) comprising:
a carrier layer (10) and
an adhesive layer (20),
wherein the label (100) comprises a wavelength conversion layer (CL1), which comprises a fluorescent substance (DYE1).

Example 2. A label (100) comprising:
a carrier layer (10) and
an adhesive layer (20),
wherein the label (100) comprises a waveguide (WG1), which comprises a fluorescent substance (DYE1).

Example 3. The label (100) according to example 1 or 2 wherein the thickness of the wavelength conversion layer (CL1) is in the range of 5% to 80% of the total thickness of the label (100).

Example 4. The label (100) according to any of the examples 1 to 3 wherein the thickness of the wavelength conversion layer (CL1) is in the range of 1 µm to 200 µm.

Example 5. The label (100) according to any of the examples 1 to 4 wherein the fluorescent substance (DYE1) is an organic dye.

Example 6. The label (100) according to any of the examples 1 to 5 comprising a substantially transparent modulating structure (STR1) to provide a machine-detectable pattern (UMRK1) when the label (100) is illuminated with excitation light (EX1).

Example 7. The label (100) according to any of the examples 1 to 6 wherein fluorescence quantum yield of the label (100) depends on transverse position (x,y).

Example 8. The label (100) according to any of the examples 1 to 7 wherein optical transmittance of the label (100) at the wavelength of 650 nm is higher than 80% in at least 90% of the area of the label (100).

Example 9. The label (100) according to any of the examples 1 to 8 wherein optical transmittance of the label (100) at the wavelength of 550 nm is higher than 80% over a region, which represents 80% of the area of the label (100).

Example 10. The label (100) according to any of the examples 1 to 9 wherein optical transmittance of the label (100) in a wavelength range of 500 nm to 700 nm is higher than 80% over a region, which represents 90% of the area of the label (100).

Example 11. The label (100) according to any of the examples 1 to 10, wherein the modulating structure (STR1) provides a target pattern for image recognition.

Example 12. The label (100) according to any of the examples 1 to 11, wherein the modulating structure (STR1) comprises encoded data.

Example 13. The label (100) according to any of the examples 1 to 12, wherein the modulating structure (STR1) provides a one-dimensional barcode, a two-dimensional barcode, an alphanumerical code, and/or a character string.

Example 14. The label (100) according to any of the examples 1 to 13, wherein the modulating structure (STR1) has a first concentration of the fluorescent substance at a first transverse position and a second concentration of the fluorescent substance at a second transverse position.

Example 15. The label (100) according to any of the examples 1 to 14, wherein a fluorescent layer of the modulating structure (STR1) has a first thickness ($d_{CL1}$) at a first transverse position and a second thickness (d3) at a second transverse position.

Example 16. The label (100) according to any of the examples 1 to 15 comprising a visually detectable marking (90), which is located between the fluorescent layer (CL1) and the adhesive layer.

Example 17. The label (100) according to any of the examples 1 to 16, wherein the modulating structure (STR1) comprises one or more spectrally filtering regions (C3) positioned above the fluorescent layer (CL1), wherein the filter regions (C3) locally prevent propagation of excitation light (EX1) to the fluorescent layer (CL1).

Example 18. The label (100) according to any of the examples 1 to 17, wherein the modulating structure (STR1) comprises one or more optical long pass filter regions (C3) positioned above the fluorescent layer (CL1), wherein the filter regions (C3) locally prevent propagation of excitation light (EX1) to the fluorescent layer (CL1).

Example 19. The label (100) according to any of the examples 1 to 18, wherein the modulating structure (STR1) comprises one or more UV-blocking filter regions (C3) positioned above the fluorescent layer (CL1), wherein the UV-blocking filter regions (C3) locally prevent propagation of UV light (EX1) to the fluorescent layer (CL1).

Example 20. The label (100) according to any of the examples 1 to 19, wherein the adhesive layer (20) comprises fluorescent substance (DYE1).

Example 21. The label (100) according to any of the examples 1 to 20, wherein the carrier layer (10) comprises fluorescent substance (DYE1).

Example 22. The label (100) according to any of the examples 1 to 21, wherein the label (100) is arranged to couple waveguided fluorescence light (LUM1) out of an edge (EDG1) of the label (100).

Example 23. The label (100) according to any of the examples 1 to 22, comprising one or more out-coupling elements (ELE1) to couple waveguided light out of the waveguiding conversion layer (WG1).

Example 24. The label (100) according to any of the examples 1 to 23, wherein at least one of the out-coupling elements (ELE1) is rough (frosted) region or a diffraction grating.

Example 25. The label (100) according to any of the examples 1 to 24, comprising one or more perforations (PERF1).

Example 26. The label (100) according to any of the examples 1 to 25, wherein the adhesive layer (20) comprises a pressure sensitive adhesive (PSA).

Example 27. A sealed package (LC1), which comprises a label (100) according to any of the examples 1 to 27.

Example 28. A method for producing a label (100) according to any of the examples 1 to 26.

Example 29. An adhesive laminate web (WEB1), which comprises a plurality of labels (100), the labels being labels according to any of the examples 1 to 26.

Example 30. A method, comprising:
providing a combination (LC1) of a package (200) and a label (100) attached to the package (200), the label (100) being a label according to any of the examples 1 to 29,
illuminating the label (100) with excitation light (EX1) so as to cause the label (100) to emit fluorescence light (LUM1),
capturing an image (IMG1) of the label (100) by using an imaging unit (CAM1), and
analyzing the captured image (IMG1).

Example 31. The method of example 30, wherein the label (100) comprises a waveguide (WG1), which in turn comprises a fluorescent substance (DYE1).

Example 32. The method of example 30 or 31, wherein said analyzing comprises one or more of the following:
detecting a pattern,
recognizing a pattern,
recognizing a pattern, which represents a machine-readable code,
detecting the position of the label with respect to the package,
detecting the position of the label with respect to the package by comparing the captured image with reference data,
detecting the position of the label with respect to the package by comparing the captured image with one or more reference images,
checking whether the adhesive layer of the label is properly in contact with the package, by comparing the captured image with reference data, and/or
checking whether the adhesive layer of the label is properly in contact with the package, by comparing the captured image one or more reference images.

Example 33. The method according to any of the examples 30 to 32, comprising determining the position of the label (100) by analyzing the captured image (IMG1).

Example 34. The method according to any of the examples 30 to 33, comprising capturing the image (IMG1) in a spectrally selective manner, by rejecting one or more spectral components of light (EX1R) reflected and/or scattered from the label (100).

Example 35. The method according to any of the examples 30 to 34, comprising capturing the image (IMG1)

in a spectrally selective manner, by using an optical filter (FIL1) to prevent propagation of one or more spectral components of light (EX1R) from the label (100) to the image sensor (SEN1) of the camera (CAM1).

Example 36. The method according to any of the examples 30 to 35, comprising detecting fluorescence light (LUM1), which is coupled of a waveguiding layer (CL1) of the label (100) by an out-coupling element (ELE1) and/or by a perforation (PERF1).

Example 37. An apparatus (500) for detecting position of a label with respect to package (200),
the apparatus (500) comprising:
a light source (LS1) to provide excitation light (EX1),
a camera (CAM1) for capturing an image (IMG1) of a labeled package,
one or more data processors (CNT1) to determine the position of the label (100) by analyzing the captured image (IMG1).

For the person skilled in the art, it will be clear that modifications and variations of the devices and the methods according to the present invention are perceivable. The figures are schematic. The particular embodiments described above with reference to the accompanying drawings are illustrative only and not meant to limit the scope of the invention, which is defined by the appended claims.

The invention claimed is:

1. A combination of a package and substantially transparent sealing label attached to the package, the label comprising:
a carrier layer and
an adhesive layer,
wherein the label comprises a wavelength conversion layer, which comprises a fluorescent substance,
wherein the label comprises a substantially transparent modulating structure to provide a machine-detectable pattern when the label is illuminated with excitation light,
wherein the modulating structure comprises one or more spectrally filtering regions positioned above the fluorescent wavelength conversion layer, wherein the filter regions locally prevent propagation of excitation light to the fluorescent wavelength conversion layer.

2. The combination of claim 1, wherein the label comprises a waveguide, which comprises a fluorescent substance.

3. The combination of claim 2, wherein the label comprises one or more out-coupling elements to couple waveguided light out of the waveguiding conversion layer.

4. The combination of claim 1 wherein the thickness of the wavelength conversion layer is in the range of 5% to 80% of the total thickness of the label.

5. The combination of claim 1, wherein the modulating structure provides a target pattern for image recognition.

6. The combination of claim 1 wherein fluorescence quantum yield of the label depends on transverse position.

7. The combination of claim 1, wherein optical transmittance of the label at the wavelength of 650 nm is higher than 80% in at least 90% of the area of the label.

8. The combination of claim 1 wherein optical transmittance of the label in a wavelength range of 500 nm to 700 nm is higher than 80% over a region, which represents 90% of the area of the label.

9. The combination of claim 1, wherein the label comprises one or more perforations.

10. A method, comprising providing a combination of a package and a substantially transparent sealing label attached to the package, wherein the label comprises a carrier layer and an adhesive layer, wherein the label comprises a wavelength conversion layer, which comprises a fluorescent substance, wherein the label comprises a substantially transparent modulating structure to provide a machine-detectable pattern when the label is illuminated with excitation light, wherein the modulating structure comprises one or more spectrally filtering regions positioned above the fluorescent wavelength conversion layer, wherein the filter regions locally prevent propagation of excitation light to the fluorescent wavelength conversion layer,
the method further comprising:
illuminating the label with excitation light so as to cause the label to emit fluorescence light,
capturing an image of the label by using an imaging unit, and
analyzing the captured image.

11. The method of claim 10, wherein the label comprises a waveguide, which in turn comprises a fluorescent substance, the method comprising detecting fluorescence light, which is coupled of the waveguiding layer by an out-coupling element.

12. The method of claim 10, comprising determining the position of the label by analyzing the captured image.

13. The method of claim 10, comprising capturing the image in a spectrally selective manner, by using an optical filter to prevent propagation of one or more spectral components of light from the label to the image sensor of the camera.

14. The method of claim 10, wherein the imaging unit comprises a plurality of first detector pixels to provide a first component image by detecting fluorescence light, wherein the imaging unit further comprises a plurality of second detector pixels to provide a second component image by detecting light reflected and/or scattered from the package, wherein the first detector pixels have a first spectral response, and the second detector pixels have a second different spectral response.

15. The method of claim 10, comprising checking whether the adhesive layer of the label is properly in contact with the package, by comparing the captured image with reference data.

16. A combination of a package and substantially transparent sealing label attached to the package, the label comprising:
a carrier layer and
an adhesive layer,
wherein the label comprises a wavelength conversion layer, which comprises a fluorescent substance, wherein the label comprises a substantially transparent modulating structure to provide a machine-detectable pattern when the label is illuminated with excitation light, wherein the modulating structure has a first concentration of the fluorescent substance at a first transverse position and a second concentration of the fluorescent substance at a second transverse position.

17. A combination of a package and substantially transparent sealing label attached to the package, the label comprising:
a carrier layer and
an adhesive layer,
wherein the label comprises a wavelength conversion layer, which comprises a fluorescent substance, wherein the label comprises a substantially transparent modulating structure to provide a machine-detectable pattern when the label is illuminated with excitation light, wherein a fluorescent layer of the modulating structure has a first thickness at a rust transverse position and a second thickness at a second transverse position.

18. A method, comprising providing a combination of a package and a substantially transparent sealing label attached to the package, wherein the label comprises a carrier layer and an adhesive layer, wherein the label comprises a wavelength conversion layer, which comprises a fluorescent substance, wherein the label comprises a substantially transparent modulating structure to provide a machine-detectable pattern when the label is illuminated with excitation light, wherein the modulating structure has a rust concentration of the fluorescent substance at a first transverse position and a second concentration of the fluorescent substance at a second transverse position, the method further comprising:
- illuminating the label with excitation light so as to cause the label to emit fluorescenee light,
- capturing an image of the label by using an imaging unit, and
- analyzing the captured image.

19. A method, comprising providing a combination of a package and a substantially transparent sealing label attached to the package, wherein the label comprises a carrier layer and an adhesive layer, wherein the label comprises a wavelength conversion layer, which comprises a fluorescent substance, wherein the label comprises a substantially transparent modulating structure to provide a machine-detectable pattern when the label is illuminated with excitation light, wherein a fluorescent layer of the modulating structure has a first thickness at a first transverse position and a second thickness at a second transverse position, the method further comprising:
- illuminating the label with excitation light so as to cause the label to emit fluorescence light,
- capturing an image of the label by using an imaging unit, and
- analyzing the captured image.

* * * * *